United States Patent
Blomgren et al.

(10) Patent No.: US 10,092,583 B2
(45) Date of Patent: Oct. 9, 2018

(54) IMIDAZOPYRIDINES SYK INHIBITORS

(71) Applicant: Gilead Connecticut, Inc., Foster City, CA (US)

(72) Inventors: Peter A. Blomgren, Issaquah, WA (US); Kevin S. Currie, North Bend, WA (US); Jeffrey E. Kropf, Issaquah, WA (US); Seung H. Lee, Sammamish, WA (US); Scott A. Mitchell, Kenmore, WA (US); Aaron C. Schmitt, Hamden, CT (US); Jianjun Xu, Seattle, WA (US); Zhongdong Zhao, Bellevue, WA (US)

(73) Assignee: Gilead Connecticut, Inc., Foster City, CA (US)

( * ) Notice: Subject to any disclaimer, the term of this patent is extended or adjusted under 35 U.S.C. 154(b) by 0 days.

(21) Appl. No.: 15/387,557

(22) Filed: Dec. 21, 2016

(65) Prior Publication Data
US 2017/0095490 A1 Apr. 6, 2017

Related U.S. Application Data

(62) Division of application No. 13/806,094, filed as application No. PCT/US2011/028194 on Mar. 11, 2011, now Pat. No. 9,562,056.

(60) Provisional application No. 61/313,223, filed on Mar. 12, 2010, provisional application No. 61/312,771, filed on Mar. 11, 2010.

(51) Int. Cl.
| | |
|---|---|
| *A61K 31/69* | (2006.01) |
| *A61K 31/437* | (2006.01) |
| *A61K 31/444* | (2006.01) |
| *A61K 31/4545* | (2006.01) |
| *A61K 31/496* | (2006.01) |
| *A61K 31/498* | (2006.01) |
| *A61K 31/506* | (2006.01) |
| *A61K 31/517* | (2006.01) |
| *A61K 31/5377* | (2006.01) |
| *A61K 31/538* | (2006.01) |
| *A61K 31/5383* | (2006.01) |
| *A61K 31/4985* | (2006.01) |

(52) U.S. Cl.
CPC .......... *A61K 31/69* (2013.01); *A61K 31/437* (2013.01); *A61K 31/444* (2013.01); *A61K 31/4545* (2013.01); *A61K 31/496* (2013.01); *A61K 31/498* (2013.01); *A61K 31/4985* (2013.01); *A61K 31/506* (2013.01); *A61K 31/517* (2013.01); *A61K 31/538* (2013.01); *A61K 31/5377* (2013.01); *A61K 31/5383* (2013.01)

(58) Field of Classification Search
CPC .. C07D 471/04; C07D 519/00; C07D 498/04; C07D 487/04; A61K 31/69; A61K 31/437; A61K 31/444; A61K 31/4545; A61K 31/496; A61K 31/498; A61K 31/506; A61K 31/517; A61K 31/5377; A61K 31/538; A61K 31/5383
See application file for complete search history.

(56) References Cited

U.S. PATENT DOCUMENTS

| | | | |
|---|---|---|---|
| 5,593,997 | A | 1/1997 | Dow et al. |
| 5,658,857 | A | 8/1997 | Dow et al. |
| 5,783,576 | A | 7/1998 | Roos et al. |
| 5,846,514 | A | 12/1998 | Foster et al. |
| 6,334,997 | B1 | 1/2002 | Foster et al. |
| 6,919,340 | B2 | 7/2005 | Currie et al. |
| 6,919,341 | B2 | 7/2005 | Paruch et al. |
| 7,160,885 | B2 | 1/2007 | Currie et al. |
| 7,189,723 | B2 | 3/2007 | Mitchell et al. |
| 7,259,164 | B2 | 8/2007 | Mitchell et al. |
| 7,312,341 | B2 | 12/2007 | DeSimone et al. |
| 7,405,295 | B2 | 7/2008 | Currie et al. |
| 8,440,667 | B2 | 5/2013 | Mitchell et al. |
| 8,450,321 | B2 | 5/2013 | Mitchell et al. |
| 8,455,493 | B2 | 6/2013 | Mitchell et al. |
| 8,697,699 | B2 | 4/2014 | Mitchell et al. |
| 8,748,607 | B2 | 6/2014 | Mitchell et al. |
| 8,765,761 | B2 | 7/2014 | Mitchell et al. |
| 9,120,811 | B2 | 9/2015 | Mitchell et al. |
| 9,212,191 | B2 | 12/2015 | Mitchell et al. |
| 9,290,505 | B2 | 3/2016 | Blomgren et al. |
| 9,376,441 | B2 | 6/2016 | Currie et al. |
| 9,382,256 | B2 | 7/2016 | Casteel et al. |
| 9,504,684 | B2 | 11/2016 | Blomgren et al. |

(Continued)

FOREIGN PATENT DOCUMENTS

| | | |
|---|---|---|
| CA | 2175837 | 5/1995 |
| DE | 4337609 | 5/1995 |

(Continued)

OTHER PUBLICATIONS

U.S. Appl. No. 61/240,983, filed Sep. 9, 2009, Gilead Connecticut, Inc.

(Continued)

*Primary Examiner* — Sahar Javanmard
(74) *Attorney, Agent, or Firm* — Sheppard Mullin Richter & Hampton LLP

(57) ABSTRACT

Certain imidazopyridines and pharmaceutical compositions thereof are provided herein. Methods of treating patients suffering from certain diseases and disorders responsive to the inhibition of Syk activity, which comprises administering to such patients an amount of at least one chemical entity effective to reduce signs or symptoms of the disease or disorder are provided. Also provided are methods for determining the presence or absence of Syk kinase in a sample.

19 Claims, No Drawings

(56) References Cited

U.S. PATENT DOCUMENTS

| | | |
|---|---|---|
| 9,567,348 B2 | 2/2017 | Mitchell et al. |
| 9,687,492 B2 | 6/2017 | Di Paolo et al. |
| 9,707,236 B2 | 7/2017 | Di Paolo et al. |
| 9,796,718 B2 | 10/2017 | Mitchell et al. |
| 2003/0212073 A1 | 11/2003 | Currie et al. |
| 2004/0063715 A1 | 4/2004 | Paruch et al. |
| 2004/0067951 A1 | 4/2004 | DeSimone et al. |
| 2004/0072835 A1 | 4/2004 | Paruch et al. |
| 2004/0102455 A1 | 5/2004 | Burns et al. |
| 2004/0220189 A1 | 11/2004 | Sun et al. |
| 2005/0009832 A1 | 1/2005 | Sun et al. |
| 2005/0054648 A1 | 3/2005 | Mitchell et al. |
| 2005/0054649 A1 | 3/2005 | Currie et al. |
| 2005/0085484 A1 | 4/2005 | Mitchell et al. |
| 2005/0090499 A1 | 4/2005 | Currie et al. |
| 2005/0101604 A1 | 5/2005 | Currie et al. |
| 2005/0288295 A1 | 12/2005 | Currie et al. |
| 2006/0069084 A1 | 3/2006 | Burns et al. |
| 2006/0084650 A1 | 4/2006 | Dong et al. |
| 2006/0148796 A1 | 7/2006 | Zimmermann et al. |
| 2006/0183746 A1 | 8/2006 | Currie et al. |
| 2007/0105864 A1 | 5/2007 | Guzi et al. |
| 2007/0117804 A1 | 5/2007 | Zhao et al. |
| 2009/0221612 A1 | 9/2009 | Zhao et al. |
| 2012/0220582 A1 | 8/2012 | Mitchell et al. |
| 2013/0231330 A1 | 9/2013 | Mitchell et al. |
| 2013/0237520 A1 | 9/2013 | Mitchell et al. |
| 2013/0267496 A1 | 10/2013 | Mitchell et al. |
| 2013/0310363 A1 | 10/2013 | Mitchell et al. |
| 2014/0148430 A1 | 5/2014 | Blomgren et al. |
| 2016/0031894 A1 | 2/2016 | Mitchell et al. |
| 2016/0166580 A1 | 6/2016 | Casteel et al. |
| 2016/0168155 A1 | 6/2016 | Fung et al. |
| 2016/0220573 A1 | 8/2016 | Di Paolo et al. |
| 2016/0310490 A1 | 10/2016 | Blomgren et al. |
| 2016/0368918 A1 | 12/2016 | Blomgren et al. |
| 2016/0375019 A1 | 12/2016 | Di Paolo et al. |
| 2017/0020821 A1 | 1/2017 | Casteel et al. |
| 2017/0035755 A1 | 2/2017 | Blomgren et al. |
| 2017/0121350 A1 | 5/2017 | Blomgren et al. |
| 2017/0217967 A1 | 8/2017 | Elford et al. |
| 2017/0258804 A1 | 9/2017 | Di Paolo et al. |

FOREIGN PATENT DOCUMENTS

| | | |
|---|---|---|
| EP | 480713 | 4/1992 |
| JP | 2001-302667 | 10/2001 |
| JP | 2004-528295 | 9/2004 |
| JP | 2005-530739 | 10/2005 |
| JP | 2011-511835 | 10/2005 |
| JP | 2008-519843 | 6/2008 |
| WO | WO-1988/004298 | 6/1988 |
| WO | WO-1995/012594 | 5/1995 |
| WO | WO-1996/004298 | 2/1996 |
| WO | WO-1996/034866 | 11/1996 |
| WO | WO-1999/028322 | 6/1999 |
| WO | WO-2001/027119 | 4/2001 |
| WO | WO-2001/083485 | 11/2001 |
| WO | WO-2002/010170 | 2/2002 |
| WO | WO-2002/030428 | 4/2002 |
| WO | WO-2002/060492 | 8/2002 |
| WO | WO-2002/066481 | 8/2002 |
| WO | WO-2002/076985 | 10/2002 |
| WO | WO-2003/070732 | 8/2003 |
| WO | WO-2003/089434 | 10/2003 |
| WO | WO-2004/022562 | 3/2004 |
| WO | WO-2004/026310 | 4/2004 |
| WO | WO-2004/026867 | 4/2004 |
| WO | WO-2004/026877 | 4/2004 |
| WO | WO-2004/072080 | 4/2004 |
| WO | WO-2004/072081 | 4/2004 |
| WO | WO-2005/005429 | 1/2005 |
| WO | WO-2005/014599 | 2/2005 |
| WO | WO-2005/019220 | 3/2005 |
| WO | WO-2005/023759 | 3/2005 |
| WO | WO-2005/047290 | 5/2005 |
| WO | WO-2005/085252 | 9/2005 |
| WO | WO-2006/044687 | 4/2006 |
| WO | WO-2006/053121 | 5/2006 |
| WO | WO-2007/008541 | 1/2007 |
| WO | WO-2008/025821 | 3/2008 |
| WO | WO-2008/065199 | 6/2008 |
| WO | WO-2009/077334 | 6/2009 |
| WO | WO-2009/102468 | 8/2009 |
| WO | WO-2009/155388 | 12/2009 |
| WO | WO-2010/006947 | 1/2010 |
| WO | WO-2010/027500 | 3/2010 |
| WO | WO-2010/038257 | 6/2010 |
| WO | WO-2010/068257 | 6/2010 |
| WO | WO-2010/068258 | 6/2010 |
| WO | WO-2011/112995 | 9/2011 |
| WO | WO-2015/017460 | 2/2015 |

OTHER PUBLICATIONS

U.S. Appl. No. 15/719,399, filed Sep. 28, 2017, Gilead Connecticut, Inc.
U.S. Appl. No. 15/788,583, filed Oct. 19, 2017, Gilead Connecticut, Inc.
U.S. Appl. No. 15/622,737, filed Jun. 14, 2017, Gilead Sciences, Inc.
U.S. Appl. No. 15/705,159, filed Sep. 14, 2017, Gilead Sciences, Inc.
U.S. Appl. No. 15/705,139, filed Sep. 14, 2017, Gilead Sciences, Inc.
Al-Dabbagh, et al. (1984). "Species Differences in Oxidative Drug Metabolism: Some Basic Considerations." Archives of Toxicology. Supplement. Archivefur Toxikologie. Supplement, 7:219-231.
Bundgaard, (1985). Design of Prodrugs, Elsevier Science Publishers, B.V., The Netherlands, p. 1.
Dean, (2000). "Recent Advances in the Synthesis and Applications of Radiolabeled Compounds for Drug Discovery and Development," Curr. Pharm Des. 6(10): Preface, 1 page.
Ding, et al. (2002) "A Combinatorial Scaffold Approach Toward Kinase-Directed Heterocycle Libraries," J. Am Chem Soc., 124(8):1594-1596.
Evans, (1981). "Synthesis of Radiolabeled Compounds," J. Radioanal. Chem. 64(1-2):9-32.
European Communication dated Oct. 24, 2012, for European Patent Application No. 09710901.1, filed on Feb. 12, 2009, five pages.
European Communication dated Jun. 6, 2013, for EP Patent Application No. 09 832 228.2 filed on Jun. 21, 2011, 5 pages.
European Communication dated Jun. 18, 2013, for EP Patent Application No. 11 709 600.8 filed on Mar. 11, 2011, 6 pages.
Extended European Search Report dated Jul. 27, 2012, for EP 09 83 2228.2, filed on Jun. 21, 2011, 12 pages.
Extended European Search Report dated Apr. 26, 2012, for EP 09 83 2229, filed on Jun. 21, 2011, 6 pages.
Extended European Search Report dated Mar. 12, 2014, for EP 13005979.3, filed on Dec. 20, 2013, 5 pages.
Final Office Action dated Oct. 30, 2012, for U.S. Appl. No. 12/632,140, filed Dec. 7, 2009, 9 pages.
Final Office Action dated Sep. 5, 2012, for U.S. Appl. No. 12/632,151, filed Dec. 7, 2009, 11 pages.
Final Office Action dated May 25, 2012, for U.S. Appl. No. 12/632,140, filed Dec. 7, 2009, 9 pages.
Final Office Action dated Jan. 27, 2012, for U.S. Appl. No. 12/632,151, filed Dec. 7, 2009, 15 pages.
Final Office Action dated Sep. 15, 2011, for U.S. Appl. No. 12/632,140, filed Dec. 7, 2009, 15 pages.
Final Office Action dated May 2, 2013 for U.S. Appl. No. 13/343,624, filed Jan. 4, 2012, 9 pages.
GenBank Accession No. AY050647.1, created on Oct. 7, 2001, located at <http://www.ncbi.nlm.nih.gov/nuccore/AY050647.1>, last visited on Dec. 28, 2011, 1 page.
Hackam, et al. (2006). "Translation of Research Evidence From Animals to Humans," JAMA 296(14):1731-1732.

(56) References Cited

OTHER PUBLICATIONS

International Preliminary Examination Report dated Aug. 5, 2004, for PCT Application No. PCT/US2003/12222, filed Apr. 21, 2003, 11 pages.
International Preliminary Examination Report dated Oct. 27, 2004, for PCT Application No. PCT/US2003/28329, filed on Sep. 9, 2003, 5 pages.
International Preliminary Report on Patentability dated May 12, 2009, for PCT Application No. PCT/US2009/000919, filed on Feb. 12, 2009, 8 pages.
International Preliminary Report on Patentability dated Jan. 5, 2011, for PCT Application No. PCT/US2009/006445, filed on Dec. 7, 2009, 6 pages.
International Preliminary Report on Patentability dated Jun. 8, 2011, for PCT Application No. PCT/US/2009/006446, filed on Dec. 7, 2009, 6 pages.
International Search Report dated Oct. 22, 2003, for PCT Application No. PCT/US2003/12222, filed on Apr. 21, 2003, 6 pages.
International Search Report dated Feb. 9, 2004, for PCT Application No. PCT/US2003/28329, filed on Sep. 9, 2003, 4 pages.
International Search Report and Written Opinion dated Jul. 7, 2004, for PCT Application No. PCT/US2004/003922, filed on Feb. 10, 2004, 12 pages.
International Search Report and Written Opinion dated Jul. 7, 2004, for PCT Application No. PCT/US2004/003923, filed on Feb. 10, 2004, 12 pages.
International Search Report and Written Opinion dated Dec. 8, 2004, for PCT Application No. PCT/US2004/021150, filed on Jun. 30, 2004, 10 pages.
International Search Report and Written Opinion dated Dec. 30, 2004, for PCT Application No. PCT/US2004/018227, filed on Jun. 4, 2004, 10 pages.
International Search Report and Written Opinion dated Feb. 1, 2005 for PCT Application No. PCT/US2004/025884, filed on Aug. 11, 2004, 8 pages.
International Search Report and Written Opinion dated Jun. 23, 2005, for PCT Application No. PCT/US2004/037433, filed on Nov. 10, 2004, 15 pages.
International Search Report dated May 12, 2009, for PCT Application No. PCT/US2009/000919, filed on Feb. 12, 2009, 5 pages.
International Search Report dated Feb. 12, 2010, for PCT Application No. PCT/US2009/006445, filed on Dec. 7, 2009, 3 pages.
International Search Report dated Feb. 12, 2010, for PCT Application No. PCT/US/2009/006446, filed on Dec. 7, 2009, 3 pages.
Invitation to Pay Additional Fees with Partial International Search Report dated May 3, 2005, for PCT Application No. PCT/US2004/037433, filed on Nov. 10, 2004, 9 pages.
International Search Report dated Apr. 26, 2011, for Application No. PCT/US2011/028194, filed on Mar. 11, 2011, 5 pages.
Jeffrey, et al. (1998). "Phosphodiesterase III and V Inhibitors on Pulmonary Artery from Pulmonary Hypertensive Rats: Differences Between Early and established Pulmonary Hypertension", J. Cardiovascular Pharmacology, 32(2): 213-219.
Jordan, (Mar. 2003). "Tamoxifen: A Most Unlikely Pioneering Medicine" Nature Reviews: Drug Discovery 2:205-213.
Kabalka, et al. (1989). "The Synthesis of Radiolabeled Compounds via Organometallic Intermediates," Tetrahedron 45(21):6601-21.
Kuhnz, et al. (Jun. 11, 1998). "Predicting the Oral Bioavailability of 19-Nortestosterone Progestins in Vivo from their Metabolic Stability in Human Liver Microsomal Preparation in Vitro," The American Society for Pharmacology and ExperimentalTherapeutics 26(11)1120-1127.
Lumma, Jr., et al. (1983) "Piperazinylimidazo [1,2-a]pyrazines with Selective affinity for in Vitro a-Adrenergic Receptor Subtypes," J. Med. Chem. 26(3):357-363.
Non-Final Office Action dated Apr. 3, 2006, for U.S. Appl. No. 10/776,002, filed Feb. 10, 2004, 13 pages.
Non-Final Office Action dated May 24, 2006, for U.S. Appl. No. 10/776,631, filed Feb. 10, 2004, 10 pages.
Non-Final Office Action dated Sep. 26, 2006, for U.S. Appl. No. 10/658,121, filed Sep. 9, 2003, 7 pages.
Non-Final Office Action dated Jan. 8, 2007, for U.S. Appl. No. 10/915,696, filed Aug. 11, 2004, 8 pages.
Non-Final Office Action dated Apr. 13, 2011 for U.S. Appl. No. 12/370,103, filed Feb. 12, 2009, 11 pages.
Non-Final Office Action dated May 10, 2011 for U.S. Appl. No. 12/632,140, filed Dec. 7, 2009, 18 pages.
Non-Final Office Action dated Jun. 29, 2011, for U.S. Appl. No. 12/632,151, filed Dec. 7, 2009, 17 pages.
Non-Final Office Action dated Feb. 17, 2012 for U.S. Appl. No. 12/632,140, filed Dec. 7, 2009, 11 pages.
Non-Final Office Action dated May 17, 2012, for U.S. Appl. No. 12/632,151, filed Dec. 7, 2009, 15 pages.
Non-Final Office Action dated Oct. 11, 2012, for U.S. Appl. No. 13/441,441, filed Apr. 6, 2012, 8 pages.
Non-Final Office Action dated Jan. 25, 2013, for U.S. Appl. No. 13/343,624, filed Jan. 4, 2012, 18 pages.
Non-Final Office Action dated Oct. 11, 2013, for U.S. Appl. No. 13/868,967, filed Apr. 23, 2013, 17 pages.
Non-Final Office Action dated Oct. 16, 2013, for U.S. Appl. No. 13/868,971, filed Apr. 23, 2013, 16 pages.
Non-Final Office Action dated Nov. 4, 2013, for U.S. Appl. No. 13/862,147, filed Apr. 12, 2013, 18 pages.
Non-Final Office Action dated Dec. 31, 2013, for U.S. Appl. No. 13/901,523, filed May 23, 2013, 22 pages.
Notice of Allowance dated Aug. 11, 2006, for U.S. Appl. No. 10/776,002, filed Feb. 10, 2004, 10 pages.
Notice of Allowance dated Sep. 7, 2006, for U.S. Appl. No. 10/776,631, filed Feb. 10, 2004, 7 pages.
Notice of Allowance dated Mar. 6, 2007, for U.S. Appl. No. 10/658,121, filed Sep. 9, 2003, 6 pages.
Notice of Allowance dated Apr. 20, 2007, for U.S. Appl. No. 10/915,696, filed Aug. 11, 2004, 7 pages.
Notice of Allowance dated Aug. 8, 2007, for U.S. Appl. No. 10/658,121, filed Sep. 9, 2003, 4 pages.
Notice of Allowance dated Jan. 14, 2013, for U.S. Appl. No, 12/632,151, filed Dec. 7, 2009, 8 pages.
Notice of Allowance dated Jan. 25, 2013, for U.S. Appl. No. 12/632,140, filed Dec. 7, 2009, 8 pages.
Notice of Allowance dated Jan. 28, 2013, for U.S. Appl. No. 13/441,441, filed Apr. 6, 2012 , 8 pages.
Notice of Allowance dated Aug. 12, 2013, for U.S. Appl. No. 13/343,624, filed Jan. 4, 2012, 9 pages.
Notice of Allowance dated Dec. 26, 2013, for U.S. Appl. No. 13/343,624, filed Jan. 4, 2012, 10 pages.
Notice of Allowance dated Jan. 30, 2014, for U.S. Appl. No. 13/868,971, filed Apr. 23, 2013, 10 pages.
Notice of Allowance dated Feb. 5, 2014, for U.S. Appl. No. 13/868,967, filed Apr. 23, 2013, 8 pages.
Notice of Allowance dated Feb. 12, 2014, for U.S. Appl. No. 13/862,147, filed Apr. 12, 2013, 9 pages.
Oravcova, J. et al. (1996). "Drug-Protein Binding Studies New Trends in Analytical and Experimental Methodology," J Chromatogr B 677:1-28.
Restriction Requirement dated Oct. 20, 2004, for U.S. Appl. No. 10/419,682, filed Apr. 21, 2003, 9 pages.
Restriction Requirement dated Jan. 4, 2006, for U.S. Appl. No. 10/776,002, filed Feb. 10, 2004, 7 pages.
Restriction Requirement dated Jan. 27, 2006, for U.S. Appl. No. 10/776,631, filed Feb. 10, 2004, 6 pages.
Restriction Requirement dated Jan. 30, 2006, for U.S. Appl. No. 10/658,121, filed Sep. 9, 2003, 5 pages.
Restriction Requirement dated May 18, 2006, for U.S. Appl. No. 10/658,121, filed Sep. 9, 2003, 5 pages.
Restriction Requirement dated Oct. 13, 2006, for U.S. Appl. No. 10/915,696, filed Aug. 11, 2004, 5 pages.
Restriction Requirement dated Dec. 8, 2010, for U.S. Appl. No. 12/632,140, filed Dec. 7, 2009, 10 pages.
Restriction Requirement dated on Dec. 8, 2010, for U.S. Appl. No. 12/632,151, filed Dec. 7, 2009, 10 pages.
Restriction Requirement dated Feb. 17, 2011, for U.S. Appl. No. 12/370,103, filed Feb. 12, 2009, 10 pages.

(56) References Cited

OTHER PUBLICATIONS

Restriction Requirement dated Jul. 26, 2012, for U.S. Appl. No. 13/441,441, filed Apr. 6, 2012, 9 pages.
Restriction Requirement dated Nov. 27, 2012, for U.S. Appl. No. 13/343,624, filed Jan. 4, 2012, 10 pages.
Restriction Requirement dated Jun. 14, 2013, for U.S. Appl. No. 13/862,147, filed Apr. 12, 2013, 10 pages.
Restriction Requirement dated Jun. 24, 2013, for U.S. Appl. No. 13/868,967, filed Apr. 23, 2013, 10 pages.
Restriction Requirement dated Jul. 3, 2013, for U.S. Appl. No. 13/868,971, filed Apr. 23, 2013, 5 pages.
Restriction Requirement dated Oct. 15, 2013, for U.S. Appl. No. 13/901,523, filed May 23, 2013, 5 pages.
Restriction Requirement dated Jan. 27, 2014, for U.S. Appl. No. 13/609,068, filed Nov. 26, 2012, 8 pages.
Restriction Requirement dated Apr. 14, 2014, for U.S. Appl. No. 13/862,194, filed Apr. 12, 2013, 5 pages.
Second Written Opinion dated Apr. 13, 2004, for PCT Application No. PCT/US2003/12222, filed Apr. 21, 2003, 7 pages.
Silverman, (1992), The Organic Chemistry of Drug Design and Drug Action, Academic Press, Inc., San Diego, CA, pp. 352-400.
Stenberg, et al., (2000). "KinMutBase, a Database of Human Disease-Causing Protein Kinase Mutations," Nucleic Acids Research 28(1):369-371.
Taylor, et al., (1984). "Hydrogen-Bond Geometry in Organic Crystals", Acc. Chem Res. 17:320-326.
Vitse, et al. (1999). "New Imidazo [1,2-.alpha.]pyrazine Derivatives with Bronchodilatory and Cyclic Nucleotide Phosphodiesterase Inhibitory Activities," Bioorganic and Medicinal Chemistry 7:1059-1065.
Written Opinion dated Dec. 5, 2003, for PCT Application No. PCT/US2003/12222, filed Apr. 21, 2003, 6 pages.
Written Opinion dated Jul. 6, 2004, for PCT Application No. PCT/US2003/28329, filed on Sep. 9, 2003, 5 pages.
Written Opinion dated May 12, 2009, for PCT Application No. PCT/US2009/000919, filed on Feb. 12, 2009, 7 pages.
Written Opinion dated Feb. 12, 2010, for PCT Application No. PCT/US2009/006445, filed on Dec. 7, 2009, 4 pages.
Written Opinion dated Feb. 12, 2010, for PCT Application No. PCT/US/2009/006446, filed on Dec. 7, 2009, 4 pages.
Written Opinion dated Apr. 26, 2011, for Application No. PCT/US2011/028194, filed on Mar. 11, 2011, 6 pages.
Zaragoza, D.F. (2005). Side Reactions in Organic Synthesis: A Guide to Successful Synthesis Design, Weinheim;WILEY-VCH Verlag GmbH &Co. KGaA, Preface, 2 pages.
U.S. Appl. No. 14/074,665, filed Nov. 7, 2013, Mitchell et al.
U.S. Appl. No. 14/274,618, filed May 9, 2014, Mitchell et al.
U.S. Appl. No. 14/300,189, filed Jun. 9, 2014, Mitchell et al.
Office Action dated Nov. 19, 2014 for Australian Patent Application No. 2011226689.
Office Action dated Jun. 23, 2015 for Chinese Patent Application No. 201180023252.0.
Office Action dated Feb. 3, 2015 for Japanese Patent Application No. 2012-557294.
Office Action dated Dec. 23, 2016 for Chinese Patent Application No. 201180023252.0, with English Translation, total 4 pages.
Office Action dated Nov. 11, 2015 for Japanese Patent Application No. 2012-557294, with English Translation, total 8 pages.
Office Action dated Jan. 13, 2016 for Australian Patent Application No. 2011226689.
Office Action dated Feb. 7, 2017 for Australian Patent Application No. 2016219585.
Office Action dated Jan. 16, 2017 for Canadian Patent Application No. 2792769.
Office Action dated Dec. 23, 2015 for Chinese Patent Application No. 201180023252.0 with English Translation (4 pages).
Office Action dated Oct. 10, 2014 for Chinese Patent Application No. 201180023252.0 with English Translation (13 pages).
Office Action dated Jun. 23, 2015 for Chinese Patent Application No. 201180023252.0 with English Translation (5 pages).
Office Action dated Jun. 18, 2013 for European Patent Application No. 11709600.8-1452.
Office Action dated Nov. 21, 2013 for European Patent Application No. 11709600.8-1452.
Office Action dated Feb. 3, 2015 for Japanese Patent Application No. 2012-557294 with English Translation (13 pages).
Office Action dated Nov. 11, 2015 for Japanese Patent Application No. 2012-557294 with English Translation (8 pages).
Office Action dated Jun. 14, 2016 for Japanese Patent Application No. 2015-094508.
Office Action dated Feb. 14, 2017 for Japanese Patent Application No. 2015-094508 with English Translation (7 pages).
Office Action dated Jun. 29, 2016 for Korean Patent Application No. 10-2012-7026472 with English Translation (11 pages).
Office Action dated Nov. 16, 2016 for Korean Patent Application No. 10/2012/7026472 with English Translation (7 pages).
Office Action dated Feb. 24, 2017 for Mexican Patent Application No. MX/a/2012/010418 with English Translation (4 pages).
Office Action dated May 16, 2013 for New Zealand Patent Application No. 602362.

IMIDAZOPYRIDINES SYK INHIBITORS

FIELD OF THE INVENTION

Provided herein are certain imidazopyridines, compositions, and methods of their manufacture and use.

BACKGROUND

Protein kinases, the largest family of human enzymes, encompass well over 500 proteins. Spleen Tyrosine Kinase (Syk) is a member of the Syk family of tyrosine kinases, and is a regulator of early B-cell development as well as mature B-cell activation, signaling, and survival.

Syk is a non-receptor tyrosine kinase that plays critical roles in immunoreceptor- and integrin-mediated signaling in a variety of cell types, including B-cells, macrophages, monocytes, mast cells, eosinophils, basophils, neutrophils, dendritic cells, platelets, and osteoclasts. Immunoreceptors as described here include classical immunoreceptors and immunoreceptor-like molecules. Classical immunoreceptors include B-cell and T-cell antigen receptors as well as various immunoglobulin receptors (Fc receptors). Immunoreceptor-like molecules are either structurally related to immunoreceptors or participate in similar signal transduction pathways and are primarily involved in non-adaptive immune functions, including neutrophil activation, natural killer cell recognition, and osteoclast activity. Integrins are cell surface receptors that play key roles in the control of leukocyte adhesion and activation in both innate and adaptive immunity.

Ligand binding leads to activation of both immunoreceptors and integrins, which results in Src family kinases being activated, and phosphorylation of immunoreceptor tyrosine-based activation motifs (ITAMs) in the cytoplasmic face of receptor-associated transmembrane adaptors. Syk binds to the phosphorylated ITAM motifs of the adaptors, leading to activation of Syk and subsequent phosphorylation and activation of downstream signaling pathways.

Syk is essential for B-cell activation through B-cell receptor (BCR) signaling. Syk becomes activated upon binding to phosphoryated BCR and thus initiates the early signaling events following BCR activation. B-cell signaling through BCR can lead to a wide range of biological outputs, which in turn depend on the developmental stage of the B-cell. The magnitude and duration of BCR signals must be precisely regulated. Aberrant BCR-mediated signaling can cause disregulated B-cell activation and/or the formation of pathogenic auto-antibodies leading to multiple autoimmune and/or inflammatory diseases. Mice lacking Syk show impaired maturation of B-cells, diminished immunoglobulin production, compromised T-cell-independent immune responses and marked attenuation of the sustained calcium sign upon BCR stimulation.

A large body of evidence supports the role of B-cells and the humoral immune system in the pathogenesis of autoimmune and/or inflammatory diseases. Protein-based therapeutics (such as Rituxan) developed to deplete B-cells represent an approach to the treatment of a number of autoimmune and inflammatory diseases. Auto-antibodies and their resulting immune complexes are known to play pathogenic roles in autoimmune disease and/or inflammatory disease. The pathogenic response to these antibodies is dependent on signaling through Fc Receptors, which is, in turn, dependent upon Syk. Because of Syk's role in B-cell activation, as well as FcR dependent signaling, inhibitors of Syk can be useful as inhibitors of B-cell mediated pathogenic activity, including autoantibody production. Therefore, inhibition of Syk enzymatic activity in cells is proposed as a treatment for autoimmune disease through its effects on autoantibody production.

Syk also plays a key role in FCεRI mediated mast cell degranulation and eosinophil activation. Thus, Syk is implicated in allergic disorders including asthma. Syk binds to the phosphorylated gamma chain of FCεRI via its SH2 domains and is essential for downstream signaling. Syk deficient mast cells demonstrate defective degranulation, arachidonic acid and cytokine secretion. This also has been shown for pharmacologic agents that inhibit Syk activity in mast cells. Treatment with Syk antisense oligonucleotides inhibits antigen-induced infiltration of eosinophils and neutrophils in an animal model of asthma. Syk deficient eosinophils also show impaired activation in response to FCεRI stimulation. Therefore, small molecule inhibitors of Syk will be useful for treatment of allergy-induced inflammatory diseases including asthma.

Syk is also expressed in mast cells and monocytes and has been shown to be important for the function of these cells. For example, Syk deficiency in mice is associated with impaired IgE-mediated mast cell activation, manifested as marked diminution of TNF-alpha and other inflammatory cytokine release. Syk kinase inhibitors have also been shown to inhibit mast cell degranulation in cell based assays. Additionally, Syk inhibitors have been shown to inhibit antigen-induced passive cutaneous anaphylaxis, bronchoconstriction and bronchial edema in rats.

Thus, the inhibition of Syk activity can be useful for the treatment of allergic disorders, autoimmune diseases and inflammatory diseases such as: SLE, rheumatoid arthritis, multiple vasculitides, idiopathic thrombocytopenic purpura (ITP), fibrotic disease, myasthenia gravis, allergic rhinitis, chronic obstructive pulmonary disease (COPD), adult respiratory distress syndrome (ARDs) and asthma. In addition, Syk has been reported to play an important role in ligand-independent tonic signaling through the B-cell receptor, known to be an important survival signal in B-cells. Thus, inhibition of Syk activity may be useful in treating certain types of cancer, including B-cell lymphoma and leukemia.

SUMMARY OF THE INVENTION

Provided is at least one chemical entity chosen from compounds of Formula I:

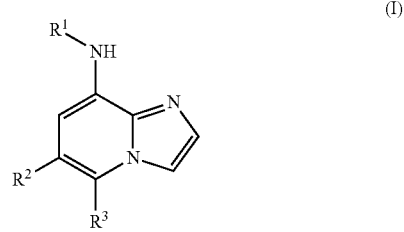

and pharmaceutically acceptable salts thereof, wherein
  $R^1$ is chosen from phenyl, pyridinyl, pyrimidinyl, pyridazinyl, pyrazolyl, and thiazolyl, each of which is optionally substituted, and each of which is further optionally fused to a heterocyclic or heteroaryl group, each of which is optionally substituted,
  $R^2$ is chosen from substituted aryl and optionally substituted heteroaryl; and R³ is chosen from hydrogen, lower alkyl, halogen, carboxamido or CO₂H, provided that if R² is 3-(4-(tert-butyl)benzamido)-2-methylphenyl, then R³ is lower alkyl, provided that if R¹ is 5-(morpholine-4-carbonyl)-pyridin-2-yl, then R³ is lower alkyl; and, further provided that the compound of Formula I is not 6-(6-phenyl-imidazo[1,2-a]pyridin-8-ylamino)-nicotinic acid ethyl ester or (6-phenyl-imidazo[1,2-a]pyridin-8-yl)-pyridin-2-yl-amine.

Also provided is a pharmaceutical composition, comprising at least one chemical entity described herein, together with at least one pharmaceutically acceptable vehicle chosen from carriers, adjuvants, and excipients.

Also provided is a method for treating a patient having a disease responsive to inhibition of Syk activity, comprising administering to the patient an effective amount of at least one chemical entity described herein.

Also provided is a method for treating a patient having a disease chosen from cancer, autoimmune diseases, inflammatory diseases, acute inflammatory reactions, and allergic disorders comprising administering to the patient an effective amount of at least one chemical entity described herein. Also provided is a method for treating a patient having polycystic kidney disease comprising administering to the patient an effective amount of at least one chemical entity described herein.

Also provided is a method for increasing sensitivity of cancer cells to chemotherapy, comprising administering to a patient undergoing chemotherapy with a chemotherapeutic agent an amount of at least one chemical entity described herein, sufficient to increase the sensitivity of cancer cells to the chemotherapeutic agent.

Also provided is a method for inhibiting ATP hydrolysis, the method comprising contacting cells expressing Syk with at least one chemical entity described herein in an amount sufficient to detectably decrease the level of ATP hydrolysis in vitro.

Also provided is a method for determining the presence of Syk in a sample, comprising contacting the sample with at least one chemical entity described herein under conditions that permit detection of Syk activity, detecting a level of Syk activity in the sample, and therefrom determining the presence or absence of Syk in the sample.

Also provided is a method for inhibiting B-cell activity comprising contacting cells expressing Syk with at least one chemical entity described herein in an amount sufficient to detectably decrease B-cell activity in vitro.

At present, selected compounds for use in the invention include, but are not limited to:

N-(3,4-dimethoxyphenyl)-6-(1H-indazol-6-yl)imidazo[1,2-a]pyridin-8-amine,
N-[6-(1H-indazol-6-yl)imidazo[1,2-a]pyridin-8-yl]-5,6-dimethoxypyridin-2-amine,
N-[6-(1H-indazol-6-yl)imidazo[1,2-a]pyridin-8-yl]pyrimidin-4-amine,
N-[6-(1,3-benzothiazol-5-yl)imidazo[1,2-a]pyridin-8-yl]-5,6-dimethoxypyridin-2-amine,
7-{8-[(5,6-dimethoxypyridin-2-yl)amino]imidazo[1,2-a]pyridin-6-yl}quinoxalin-2-o,l
6-{8-[(5,6-dimethoxypyridin-2-yl)amino]imidazo[1,2-a]pyridin-6-yl}-1H-indazol-3-amine,
N-[6-(3,4-dihydro-2H-1,4-benzoxazin-6-yl)imidazo[1,2-a]pyridin-8-yl]-5,6-dimethoxypyridin-2-amine,
N-[6-(1H-indazol-6-yl)imidazo[1,2-a]pyridin-8-yl]-1,5-dimethyl-1H-pyrazol-3-amine,
6-{8-[(1-ethyl-1H-pyrazol-3-yl)amino]imidazo[1,2-a]pyridin-6-yl}-3,4-dihydro-2H-1,4-benzoxazin-3-one,
6-{8-[(1-ethyl-1H-pyrazol-3-yl)amino]imidazo[1,2-a]pyridin-6-yl}quinazolin-2-amine,
1,5-dimethyl-N-[6-(1-methyl-1H-1,3-benzodiazol-6-yl)imidazo[1,2-a]pyridin-8-yl]-1H-pyrazol-3-amine,
N-[6-(1H-indazol-6-yl)imidazo[1,2-a]pyridin-8-yl]-5-(morpholin-4-yl)pyridin-2-amine,
N-[6-(1H-indazol-6-yl)imidazo[1,2-a]pyridin-8-yl]-2-methoxypyrimidin-4-amine,
N-[6-(3,4-dihydro-2H-1,4-benzoxazin-6-yl)imidazo[1,2-a]pyridin-8-yl]-1,5-dimethyl-1H-pyrazol-3-amine,
N-[6-(1H-indazol-6-yl)imidazo[1,2-a]pyridin-8-yl]-1-methyl-1H-pyrazol-3-amine,
1,5-dimethyl-N-[6-(1-methyl-1H-1,3-benzodiazol-5-yl)imidazo[1,2-a]pyridin-8-yl]-1H-pyrazol-3-amine,
2-N-[6-(1H-indazol-6-yl)imidazo[1,2-a]pyridin-8-yl]pyridine-2,6-diamine,
1-(6-{[6-(1H-indazol-6-yl)imidazo[1,2-a]pyridin-8-yl]amino}pyridin-3-yl)-4-methylpiperidin-4-ol,
2-[(6-{[6-(1H-indazol-6-yl)imidazo[1,2-a]pyridin-8-yl]amino}pyridin-3-yl)(methyl)amino]ethan-1-ol,
6-(1H-indazol-6-yl)-N-{4H,6H,7H-pyrazolo[3,2-c][1,4]oxazin-2-yl}imidazo[1,2-a]pyridin-8-amine,
2-N-[6-(1H-indazol-6-yl)imidazo[1,2-a]pyridin-8-yl]-5-N-(2-methoxyethyl)-5-N-methylpyridine-2,5-diamine,
N-[6-(1H-indazol-6-yl)imidazo[1,2-a]pyridin-8-yl]-6-(morpholin-4-yl)pyridazin-3-amine;
1-ethyl-N-[6-(1H-indazol-6-yl)imidazo[1,2-a]pyridin-8-yl]-5-methyl-1H-pyrazol-3-amine;
6-(8-{[6-(morpholin-4-yl)pyridazin-3-yl]amino}imidazo[1,2-a]pyridin-6-yl)-3,4-dihydro-2H-1,4-benzoxazin-3-one;
1-(6-{[6-(1H-indazol-6-yl)imidazo[1,2-a]pyridin-8-yl]amino}pyridin-3-yl)azetidin-3-ol;
1-(6-{[6-(1H-indazol-6-yl)imidazo[1,2-a]pyridin-8-yl]amino}pyridin-3-yl)-3-methylazetidin-3-ol;
1-[(6-{[6-(1H-indazol-6-yl)imidazo[1,2-a]pyridin-8-yl]amino}pyridin-3-yl)oxy]-2-methylpropan-2-ol;
[(2S)-4-(6-{[6-(1H-indazol-6-yl)imidazo[1,2-a]pyridin-8-yl]amino}pyridin-3-yl)morpholin-2-yl]methanol;
N-[6-(1H-indazol-6-yl)-5-methylimidazo[1,2-a]pyridin-8-yl]-5-(morpholin-4-yl)pyridin-2-amine;
[(2R)-4-(6-{[6-(1H-indazol-6-yl)imidazo[1,2-a]pyridin-8-yl]amino}pyridin-3-yl)morpholin-2-yl]methanol;
N-[6-(1H-indazol-6-yl)imidazo[1,2-a]pyridin-8-yl]-2-(morpholin-4-yl)-1,3-thiazol-4-amine;
N-{4H,6H,7H-pyrazolo[3,2-c][1,4]oxazin-2-yl}-6-{1H-pyrrolo[3,2-b]pyridin-6-yl}imidazo[1,2-a]pyridin-8-amine;
1-methyl-N-(6-{1H-pyrrolo[3,2-b]pyridin-6-yl}imidazo[1,2-a]pyridin-8-yl)-1H-pyrazol-3-amine;
N-(5-methyl-6-{1H-pyrrolo[3,2-b]pyridin-6-yl}imidazo[1,2-a]pyridin-8-yl)-5-(morpholin-4-yl)pyridin-2-amine;
1,5-dimethyl-N-(6-{1H-pyrrolo[3,2-b]pyridin-6-yl}imidazo[1,2-a]pyridin-8-yl)-1H-pyrazol-3-amine;
1-(2-hydroxyethyl)-5-(8-{[5-(morpholin-4-yl)pyridin-2-yl]amino}imidazo[1,2-a]pyridin-6-yl)-2,3-dihydro-1H-1,3-benzodiazol-2-one;
2-[ethyl({6-[(6-{1H-pyrrolo[3,2-b]pyridin-6-yl}imidazo[1,2-a]pyridin-8-yl)amino]pyridin-3-yl}amino]ethan-1-ol;
1-(4-{6-[(6-{1H-pyrrolo[3,2-b]pyridin-6-yl}imidazo[1,2-a]pyridin-8-yl)amino]pyridin-3-yl}piperazin-1-yl)ethan-1-one;
2-[4-({6-[3-(2-hydroxyethyl)-1H-indol-6-yl]imidazo[1,2-a]pyridin-8-yl}amino)phenyl]-2-methylpropan-1-ol;
1-{4-[6-({6-[3-(2-hydroxyethyl)-1H-indol-6-yl]imidazo[1,2-a]pyridin-8-yl}amino)pyridin-3-yl]piperazin-1-yl}ethan-1-one;

2-{5-methyl-3-[(6-{1H-pyrrolo[3,2-b]pyridin-6-yl}imidazo[1,2-a]pyridin-8-yl)amino]-1H-pyrazol-1-yl}ethan-1-ol;
6-(8-{[5-(hydroxymethyl)-1-methyl-1H-pyrazol-3-yl]amino}imidazo[1,2-a]pyridin-6-yl)-2,3-dihydro-1H-indol-2-one;
6-[8-({5-acetyl-4H,5H,6H,7H-pyrazolo[1,5-a]pyrazin-2-yl}amino)imidazo[1,2-a]pyridin-6-yl]-2,3-dihydro-1H-indol-2-one;
2-hydroxy-1-(4-{6-[(6-{1H-pyrrolo[3,2-b]pyridin-6-yl}imidazo[1,2-a]pyridin-8-yl)amino]pyridin-3-yl}piperazin-1-yl)ethan-1-one;
6-(8-{[1-(2-hydroxyethyl)-5-methyl-1H-pyrazol-3-yl]amino}imidazo[1,2-a]pyridin-6-yl)-2,3-dihydro-1H-indol-2-one;
{1-methyl-3-[(6-{1H-pyrrolo[3,2-b]pyridin-6-yl}imidazo[1,2-a]pyridin-8-yl)amino]-1H-pyrazol-5-yl}methanol;
6-[8-({5-methanesulfonyl-4H,5H,6H,7H-pyrazolo[1,5-a]pyrazin-2-yl}amino)imidazo[1,2-a]pyridin-6-yl]-2,3-dihydro-1H-indol-2-one;
N-{5-methanesulfonyl-4H,5H,6H,7H-pyrazolo[1,5-a]pyrazin-2-yl}-6-{1H-pyrrolo[3,2-b]pyridin-6-yl}imidazo[1,2-a]pyridin-8-amine;
6-(8-{[5-(4-acetylpiperazin-1-yl)pyridin-2-yl]amino}imidazo[1,2-a]pyridin-6-yl)-2,3-dihydro-1H-indol-2-one;
5-(4-ethylpiperazin-1-yl)-N-(6-{1H-pyrrolo[3,2-b]pyridin-6-yl}imidazo[1,2-a]pyridin-8-yl)pyridin-2-amine;
2-(6-(8-(5-morpholinopyridin-2-ylamino)imidazo[1,2-a]pyridin-6-yl)-1H-indol-3-yl)ethanol;
N-(5-(methoxymethyl)-1-methyl-1H-pyrazol-3-yl)-6-(1H-pyrrolo[3,2-b]pyridin-6-yl)imidazo[1,2-a]pyridin-8-amine;
N-(5-methyl-6-(1H-pyrrolo[3,2-b]pyridin-6-yl)imidazo[1,2-a]pyridin-8-yl)-6,7-dihydro-4H-pyrazolo[5,1-c][1,4]oxazin-2-amine;
6-(8-(6,7-dihydro-4H-pyrazolo[5,1-c][1,4]oxazin-2-ylamino)-5-methylimidazo[1,2-a]pyridin-6-yl)indolin-2-one;
1-(2-(6-(1H-pyrrolo[3,2-b]pyridin-6-yl)imidazo[1,2-a]pyridin-8-ylamino)-6,7-dihydropyrazolo[1,5-a]pyrazin-5(4H)-yl)ethanone;
6-(8-(5-(2-hydroxypropan-2-yl)-1-methyl-1H-pyrazol-3-ylamino)imidazo[1,2-a]pyridin-6-yl)indolin-2-one;
2-(6-(8-(6,7-dihydro-4H-pyrazolo[5,1-c][1,4]oxazin-2-ylamino)imidazo[1,2-a]pyridin-6-yl)-1H-indol-3-yl)ethanol;
5-(8-(5-(2-hydroxypropan-2-yl)-1-methyl-1H-pyrazol-3-ylamino)imidazo[1,2-a]pyridin-6-yl)-1-methyl-1H-benzo[d]imidazol-2(3H)-one;
2-(3-(6-(1H-pyrrolo[3,2-b]pyridin-6-yl)imidazo[1,2-a]pyridin-8-ylamino)-1-methyl-1H-pyrazol-5-yl)propan-2-ol;
N-(6-(3,4-dihydro-2H-benzo[b][1,4]oxazin-6-yl)imidazo[1,2-a]pyridin-8-yl)-6,7-dihydro-4H-pyrazolo[5,1-c][1,4]oxazin-2-amine;
N-(6-(1H-indazol-6-yl)-5-methylimidazo[1,2-a]pyridin-8-yl)-6,7-dihydro-4H-pyrazolo[5,1-c][1,4]oxazin-2-amine;
6-(8-(5-cyclopropyl-1H-pyrazol-3-ylamino)imidazo[1,2-a]pyridin-6-yl)indolin-2-one;
6-(8-(6,7-dihydro-4H-pyrazolo[5,1-c][1,4]oxazin-2-ylamino)imidazo[1,2-a]pyridin-6-yl)indolin-2-one;
N-(6-(1H-indol-6-yl)imidazo[1,2-a]pyridin-8-yl)-6,7-dihydro-4H-pyrazolo[5,1-c][1,4]oxazin-2-amine;
N-(5-cyclopropyl-1H-pyrazol-3-yl)-6-(1H-indazol-6-yl)imidazo[1,2-a]pyridin-8-amine;
6-(8-(5-(1-hydroxy-2-methylpropan-2-yl)pyridin-2-ylamino)imidazo[1,2-a]pyridin-6-yl)indolin-2-one;
2-(6-(8-(5-(4-ethylpiperazin-1-yl)pyridin-2-ylamino)imidazo[1,2-a]pyridin-6-yl)-1H-indazol-3-yl)ethanol;
2-(6-(8-(5-morpholinopyridin-2-ylamino)imidazo[1,2-a]pyridin-6-yl)-1H-indazol-3-yl)ethanol;
N-(5-(4-ethylpiperazin-1-yl)pyridin-2-yl)-6-(1H-indazol-6-yl)-5-methylimidazo[1,2-a]pyridin-8-amine;
N-(5-(4-ethylpiperazin-1-yl)pyridin-2-yl)-6-(1H-indol-6-yl)-5-methylimidazo[1,2-a]pyridin-8-amine;
6-(8-(5-(4-ethylpiperazin-1-yl)pyridin-2-ylamino)-5-methylimidazo[1,2-a]pyridin-6-yl)indolin-2-one;
2-(6-(8-(5-(4-ethylpiperazin-1-yl)pyridin-2-ylamino)-5-methylimidazo[1,2-a]pyridin-6-yl)-1H-indol-3-yl)ethanol;
6-(8-(5-(4-ethylpiperazin-1-yl)pyridin-2-ylamino)-5-methylimidazo[1,2-a]pyridin-6-yl)-N-methyl-1H-indole-3-carboxamide;
5-methyl-N-(5-morpholinopyridin-2-yl)-6-(1H-pyrrolo[2,3-b]pyridin-5-yl)imidazo[1,2-a]pyridin-8-amine;
1-methyl-6-(5-methyl-8-(5-morpholinopyridin-2-ylamino)imidazo[1,2-a]pyridin-6-yl)indolin-2-one;
6-(1H-indazol-6-yl)-5-methyl-N-(5-(piperazin-1-yl)pyridin-2-yl)imidazo[1,2-a]pyridin-8-amine;
5-(8-(5-(4-ethylpiperazin-1-yl)pyridin-2-ylamino)-5-methylimidazo[1,2-a]pyridin-6-yl)-1-(2-methoxyethyl)-1H-benzo[d]imidazol-2(3H)-one;
N-(5-(4-ethylpiperazin-1-yl)pyridin-2-yl)-5-methyl-6-(2-methyl-1H-indol-6-yl)imidazo[1,2-a]pyridin-8-amine;
5-ethyl-N-(5-(4-ethylpiperazin-1-yl)pyridin-2-yl)-6-(1H-indazol-6-yl)imidazo[1,2-a]pyridin-8-amine;
5-ethyl-N-(5-(4-ethylpiperazin-1-yl)pyridin-2-yl)-6-(1H-indol-6-yl)imidazo[1,2-a]pyridin-8-amine;
6-(5-ethyl-8-(5-(4-ethylpiperazin-1-yl)pyridin-2-ylamino)imidazo[1,2-a]pyridin-6-yl)indolin-2-one;
2-(1-methyl-6-(5-methyl-8-(5-morpholinopyridin-2-ylamino)imidazo[1,2-a]pyridin-6-yl)-1H-indol-3-yl)ethanol;
5-chloro-N-(5-(4-ethylpiperazin-1-yl)pyridin-2-yl)-6-(1H-indol-6-yl)imidazo[1,2-a]pyridin-8-amine;
6-(5-chloro-8-(5-(4-ethylpiperazin-1-yl)pyridin-2-ylamino)imidazo[1,2-a]pyridin-6-yl)indolin-2-one;
5-chloro-6-(1H-indazol-6-yl)-N-(5-(4-isopropylpiperazin-1-yl)pyridin-2-yl)imidazo[1,2-a]pyridin-8-amine;
2-(6-(5-chloro-8-(5-(4-ethylpiperazin-1-yl)pyridin-2-ylamino)imidazo[1,2-a]pyridin-6-yl)-1H-indol-3-yl)ethanol;
2-(6-(5-chloro-8-(5-(4-ethylpiperazin-1-yl)pyridin-2-ylamino)imidazo[1,2-a]pyridin-6-yl)-1-methyl-1H-indol-3-yl)ethanol;
5-chloro-N-(5-(4-ethylpiperazin-1-yl)pyridin-2-yl)-6-(1H-indazol-6-yl)imidazo[1,2-a]pyridin-8-amine;
6-(5-chloro-8-(5-(4-isopropylpiperazin-1-yl)pyridin-2-ylamino)imidazo[1,2-a]pyridin-6-yl)indolin-2-one;
2-(6-(5-chloro-8-(5-(4-isopropylpiperazin-1-yl)pyridin-2-ylamino)imidazo[1,2-a]pyridin-6-yl)-1-methyl-1H-indol-3-yl)ethanol;
2-(6-(5-chloro-8-(5-(4-isopropylpiperazin-1-yl)pyridin-2-ylamino)imidazo[1,2-a]pyridin-6-yl)-1H-indol-3-yl)ethanol;
5-(5-chloro-8-(5-(4-isopropylpiperazin-1-yl)pyridin-2-ylamino)imidazo[1,2-a]pyridin-6-yl)-1-(2-methoxyethyl)-1H-benzo[d]imidazol-2(3H)-one;
N-(6-(1H-indol-6-yl)imidazo[1,2-a]pyridin-8-yl)-5-methyl-4,5,6,7-tetrahydrothiazolo[5,4-c]pyridin-2-amine;
N-(6-(1H-indol-6-yl)imidazo[1,2-a]pyridin-8-yl)-5-methylisoxazol-3-amine;
5-fluoro-6-(1H-indazol-6-yl)-N-(5-(4-isopropylpiperazin-1-yl)pyridin-2-yl)imidazo[1,2-a]pyridin-8-amine;

N-(6-(1H-pyrazolo[4,3-b]pyridin-6-yl)imidazo[1,2-a]pyridin-8-yl)-5-methyl-4,5,6,7-tetrahydropyrazolo[1,5-a]pyrazin-2-amine;
6-(1H-indazol-6-yl)-8-(5-morpholinopyridin-2-ylamino)imidazo[1,2-a]pyridine-5-carboxamide;
(6-(1H-indazol-6-yl)-8-(5-morpholinopyridin-2-ylamino)imidazo[1,2-a]pyridin-5-yl)methanol;
6-(1H-indazol-6-yl)-8-(5-morpholinopyridin-2-ylamino)imidazo[1,2-a]pyridine-5-carboxylic acid; and
methyl 6-(1H-indazol-6-yl)-8-(5-morpholinopyridin-2-ylamino)imidazo[1,2-a]pyridine-5-carboxylate, and pharmaceutically acceptable salts thereof.

DETAILED DESCRIPTION OF THE INVENTION

Definitions and General Parameters

As used herein, when any variable occurs more than one time in a chemical formula, its definition on each occurrence is independent of its definition at every other occurrence. In accordance with the usual meaning of "a" and "the" in patents, reference, for example, to "a" kinase or "the" kinase is inclusive of one or more kinases.

As used in the present specification, the following words, phrases and symbols are generally intended to have the meanings as set forth below, except to the extent that the context in which they are used indicates otherwise. The following abbreviations and terms have the indicated meanings throughout:

A dash ("—") that is not between two letters or symbols is used to indicate a point of attachment for a substituent. For example, —CONH$_2$ is attached through the carbon atom.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

"Alkyl" encompasses straight chain and branched chain having the indicated number of carbon atoms, usually from 1 to 20 carbon atoms, for example 1 to 8 carbon atoms, such as 1 to 6 carbon atoms. For example $C_1$-$C_6$ alkyl encompasses both straight and branched chain alkyl of from 1 to 6 carbon atoms. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. Alkylene is another subset of alkyl, referring to the same residues as alkyl, but having two points of attachment. Alkylene groups will usually have from 2 to 20 carbon atoms, for example 2 to 8 carbon atoms, such as from 2 to 6 carbon atoms. For example, $C_0$ alkylene indicates a covalent bond and $C_1$ alkylene is a methylene group. When an alkyl residue having a specific number of carbons is named, all geometric isomers having that number of carbons are intended to be encompassed; thus, for example, "butyl" is meant to include n-butyl, sec-butyl, isobutyl and t-butyl; "propyl" includes n-propyl and isopropyl. "Lower alkyl" refers to alkyl groups having 1 to 4 carbons.

"Alkenyl" indicates an unsaturated branched or straight-chain alkyl group having at least one carbon-carbon double bond derived by the removal of one molecule of hydrogen from adjacent carbon atoms of the parent alkyl. The group may be in either the cis or trans configuration about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl; and the like. In some embodiments, an alkenyl group has from 2 to 20 carbon atoms and in other embodiments, from 2 to 6 carbon atoms.

"Cycloalkyl" indicates a saturated hydrocarbon ring group, having the specified number of carbon atoms, usually from 3 to 7 ring carbon atoms. Examples of cycloalkyl groups include cyclopropyl, cyclobutyl, cyclopentyl, and cyclohexyl as well as bridged and caged saturated ring groups such as norbornane.

By "alkoxy" is meant an alkyl group of the indicated number of carbon atoms attached through an oxygen bridge such as, for example, methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. Alkoxy groups will usually have from 1 to 6 carbon atoms attached through the oxygen bridge. "Lower alkoxy" refers to alkoxy groups having 1 to 4 carbons.

"Aminocarbonyl" encompasses a group of the formula —(C=O)NR$^a$R$^b$ where R$^a$ and R$^b$ are independently chosen from hydrogen and the optional substituents for "substituted amino" described below.

"Acyl" refers to the groups (alkyl)-C(O)—; (cycloalkyl)-C(O)—; (aryl)-C(O)—; (heteroaryl)-C(O)—; and (heterocycloalkyl)-C(O)—, wherein the group is attached to the parent structure through the carbonyl functionality and wherein alkyl, cycloalkyl, aryl, heteroaryl, and heterocycloalkyl are as described herein. Acyl groups have the indicated number of carbon atoms, with the carbon of the keto group being included in the numbered carbon atoms. For example a $C_2$ acyl group is an acetyl group having the formula CH$_3$(C=O)—.

By "alkoxycarbonyl" is meant an ester group of the formula (alkoxy)(C=O)— attached through the carbonyl carbon wherein the alkoxy group has the indicated number of carbon atoms. Thus a $C_1$-$C_6$ alkoxycarbonyl group is an alkoxy group having from 1 to 6 carbon atoms attached through its oxygen to a carbonyl linker.

By "amino" is meant the group —NH$_2$.

"Aryl" encompasses:
5- and 6-membered carbocyclic aromatic rings, for example, benzene;
bicyclic ring systems wherein at least one ring is carbocyclic and aromatic, for example, naphthalene, indane, and tetralin; and
tricyclic ring systems wherein at least one ring is carbocyclic and aromatic, for example, fluorene.

For example, aryl includes 5- and 6-membered carbocyclic aromatic rings fused to a 5- to 7-membered heterocycloalkyl ring containing 1 or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings is fused with a heterocycloalkyl aromatic ring, the resulting ring system is heteroaryl, not aryl, as defined herein.

The term "aryloxy" refers to the group —O-aryl.

The term "halo" includes fluoro, chloro, bromo, and iodo, and the term "halogen" includes fluorine, chlorine, bromine, and iodine.

"Heteroaryl" encompasses:
5- to 7-membered aromatic, monocyclic rings containing one or more, for example, from 1 to 4, or in some embodiments, from 1 to 3, heteroatoms chosen from N, O, and S, with the remaining ring atoms being carbon; and
bicyclic heterocycloalkyl rings containing one or more, for example, from 1 to 4, or in some embodiments, from 1 to 3, heteroatoms chosen from N, O, and S, with the remaining ring atoms being carbon and wherein at least one heteroatom is present in an aromatic ring.

For example, heteroaryl includes a 5- to 7-membered heterocycloalkyl, aromatic ring fused to a 5- to 7-membered cycloalkyl ring. For such fused, bicyclic heteroaryl ring systems wherein only one of the rings contains one or more heteroatoms, the point of attachment may be at the heteroaromatic ring or the cycloalkyl ring. When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1. Examples of heteroaryl groups include, but are not limited to, (as numbered from the linkage position assigned priority 1), 2-pyridyl, 3-pyridyl, 4-pyridyl, 2,3-pyrazinyl, 3,4-pyrazinyl, 2,4-pyrimidinyl, 3,5-pyrimidinyl, 2,3-pyrazolinyl, 2,4-imidazolinyl, isoxazolinyl, oxazolinyl, thiazolinyl, thiadiazolinyl, tetrazolyl, thienyl, benzothiophenyl, furanyl, benzofuranyl, benzoimidazolinyl, indolinyl, pyridizinyl, triazolyl, quinolinyl, pyrazolyl, and 5,6,7,8-tetrahydroisoquinoline. Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. Heteroaryl does not encompass or overlap with aryl as defined above.

Substituted heteroaryl also includes ring systems substituted with one or more oxide (—O$^-$) substituents, such as pyridinyl N-oxides.

The term "heteroaryloxy" refers to the group —O-heteroaryl.

By "heterocycloalkyl" is meant a single aliphatic ring, usually with 3 to 7 ring atoms, containing at least 2 carbon atoms in addition to 1-3 heteroatoms independently selected from oxygen, sulfur, and nitrogen, as well as combinations comprising at least one of the foregoing heteroatoms. Suitable heterocycloalkyl groups include, for example (as numbered from the linkage position assigned priority 1), 2-pyrrolinyl, 2,4-imidazolidinyl, 2,3-pyrazolidinyl, 2-piperidinyl, 3-piperidinyl, 4-piperidinyl, and 2,5-piperazinyl. Morpholinyl groups are also contemplated, including 2-morpholinyl and 3-morpholinyl (numbered wherein the oxygen is assigned priority 1). Substituted heterocycloalkyl also includes ring systems substituted with one or more oxo moieties, such as piperidinyl N-oxide, morpholinyl-N-oxide, 1-oxo-1-thiomorpholinyl and 1,1-dioxo-1-thiomorpholinyl.

The term "heterocycloalkyloxy" refers to the group —O-heterocylcoalkyl.

The term "nitro" refers to the group —NO2.

The term "phosphono" refers to the group —PO3H2.

"Thiocarbonyl" refers to the group —C(=O)SH.

The term "optionally substituted thiocarbonyl" includes the following groups:
—C(=O)S-(optionally substituted ($C_1$-$C_6$)alkyl), —C(=O)S-(optionally substituted aryl), C(=O)S-(optionally substituted heteroaryl), and —C(=O)S-(optionally substituted heterocycloalkyl).

The term "sulfanyl" includes the groups: —S-(optionally substituted ($C_1$-$C_6$)alkyl), —S-(optionally substituted aryl), —S-(optionally substituted heteroaryl), and —S-(optionally substituted heterocycloalkyl). Hence, sulfanyl includes the group C1-C6 alkylsulfanyl.

The term "sulfinyl" includes the groups: —S(O)—H, —S(O)-(optionally substituted (C1-C6)alkyl), —S(O)-optionally substituted aryl), —S(O)-optionally substituted heteroaryl), —S(O)-(optionally substituted heterocycloalkyl); and —S(O)-(optionally substituted amino).

The term "sulfonyl" includes the groups: —S(O2)-H, —S(O2)-(optionally substituted (C1-C6)alkyl), —S(O2)-optionally substituted aryl), —S(O2)-optionally substituted heteroaryl), —S(O2)-(optionally substituted heterocycloalkyl), —S(O2)-(optionally substituted alkoxy), —S(O2)-optionally substituted aryloxy), —S(O2)-optionally substituted heteroaryloxy), —S(O2)-(optionally substituted heterocyclyloxy); and —S(O2)-(optionally substituted amino).

The term "substituted", as used herein, means that any one or more hydrogens on the designated atom or group is replaced with a selection from the indicated group, provided that the designated atom's normal valence is not exceeded. When a substituent is oxo (i.e., =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

The terms "substituted" alkyl, cycloalkyl, aryl, heterocycloalkyl, and heteroaryl (including without limitation pyridinyl, pyridizinyl, pyrazolyl, oxazolyl, pyrrolyl, thiazolyl, and imidazolyl group), unless otherwise expressly defined, refer respectively to alkyl, cycloalkyl, aryl, heterocycloalkyl, and heteroaryl (including without limitation pyridinyl, pyridizinyl, pyrazolyl, oxazolyl, pyrrolyl, thiazolyl, and imidazolyl group) wherein one or more (such as up to 5, for example, up to 3) hydrogen atoms are replaced by a substituent independently chosen from: —$R^a$, —$OR^b$, —O($C_1$-$C_2$ alkyl)O— (e.g., methylenedioxy-), —$SR^b$, guanidine, guanidine wherein one or more of the guanidine hydrogens are replaced with a lower-alkyl group, —$NR^bR^c$, halo, cyano, oxo (as a substituent for heterocycloalkyl), nitro, —$COR^b$, —$CO_2R^b$, —$CONR^bR^c$, —$OCOR^b$, —$OCO_2R^a$, —OCONR$^b$R$^c$, —NR$^c$COR$^b$, —NR$^c$CO$_2$R$^a$, —NR$^c$CO-NR$^b$R$^c$, —SOR$^a$, —SO$_2$R$^a$, —SO$_2$NR$^b$R$^c$, and —NR$^c$SO$_2$R$^a$, where R$^a$ is chosen from optionally substituted C$_1$-C$_6$ alkyl, optionally substituted cycloalkyl, optionally substituted aryl, optionally substituted heterocycloalkyl, and optionally substituted heteroaryl;

R$^b$ is chosen from H, optionally substituted C$_1$-C$_6$ alkyl, optionally substituted aryl, and optionally substituted heteroaryl; and R$^c$ is chosen from hydrogen and optionally substituted C$_1$-C$_4$ alkyl; or R$^b$ and R$^c$, and the nitrogen to which they are attached, form an optionally substituted heterocycloalkyl group; and where each optionally substituted group is unsubstituted or independently substituted with one or more, such as one, two, or three, substituents independently selected from C$_1$-C$_4$ alkyl, C$_3$-C$_6$ cycloalkyl, aryl, heteroaryl, aryl-C$_1$-C$_4$ alkyl-, heteroaryl-C$_1$-C$_4$ alkyl-, C$_1$-C$_4$ haloalkyl-, —OC$_1$-C$_4$ alkyl, —OC$_1$-C4 alkylphenyl, —C$_1$-C$_4$ alkyl-OH, —C$_1$-C$_4$ alkyl-O—C$_1$-C$_4$ alkyl, —OC$_1$-C$_4$ haloalkyl, halo, —OH, —NH$_2$, —C$_1$-C$_4$ alkyl-NH$_2$, —N(C$_1$-C$_4$ alkyl)(C$_1$-C$_4$ alkyl), —NH(C$_1$-C$_4$ alkyl), —N(C$_1$-C$_4$ alkyl)(C$_1$-C$_4$ alkylphenyl), —NH(C$_1$-C$_4$ alkylphenyl), cyano, nitro, oxo (as a substitutent for heteroaryl), —CO$_2$H, —C(O)OC$_1$-C$_4$ alkyl, —CON(C$_1$-C$_4$ alkyl)(C$_1$-C$_4$ alkyl), —CONH(C$_1$-C$_4$ alkyl), —CONH$_2$, —NHC(O)(C$_1$-C$_4$ alkyl), —NHC(O)(phenyl), —N(C$_1$-C$_4$ alkyl)C(O)(C$_1$-C$_4$ alkyl), —N(C$_1$-C$_4$ alkyl)C(O)(phenyl), —C(O)C$_1$-C$_4$ alkyl, —C(O)C$_1$-C$_4$ phenyl, —C(O)C$_1$-C$_4$ haloalkyl, —OC(O)C$_1$-C$_4$ alkyl, —SO$_2$(C$_1$-C$_4$ alkyl), —SO$_2$(phenyl), —SO$_2$(C$_1$-C$_4$ haloalkyl), —SO$_2$NH$_2$, —SO$_2$NH(C$_1$-C$_4$ alkyl), —SO$_2$NH(phenyl), —NHSO$_2$(C$_1$-C$_4$ alkyl), —NHSO$_2$(phenyl), and —NHSO$_2$(C$_1$-C$_4$ haloalkyl).

The term "substituted acyl" refers to the groups (substituted alkyl)-C(O)—; (substituted cycloalkyl)-C(O)—; (substituted aryl)-C(O)—; (substituted heteroaryl)-C(O)—; and (substituted heterocycloalkyl)-C(O)—, wherein the group is attached to the parent structure through the carbonyl functionality and wherein substituted alkyl, cycloalkyl, aryl, heteroaryl, and heterocycloalkyl are as described herein.

The term "substituted alkoxy" refers to alkoxy wherein the alkyl constituent is substituted (i.e., —O—(substituted alkyl)) wherein "substituted alkyl" is as described herein.

The term "substituted alkoxycarbonyl" refers to the group (substituted alkyl)-O—C(O)— wherein the group is attached to the parent structure through the carbonyl functionality and wherein substituted alkyl is as described herein.

The term "substituted aryloxy" refers to aryloxy wherein the aryl constituent is substituted (i.e., —O—(substituted aryl)) wherein "substituted aryl" is as described herein.

The term "substituted heteroaryloxy" refers to heteroaryloxy wherein the aryl constituent is substituted (i.e., —O—(substituted heteroaryl)) wherein "substituted heteroaryl" is as described herein.

The term "substituted cycloalkyloxy" refers to cycloalkyloxy wherein the cycloalkyl constituent is substituted (i.e., —O—(substituted cycloalkyl)) wherein "substituted cycloalkyl" is as described herein.

The term "substituted heterocycloalkyloxy" refers to heterocycloalkyloxy wherein the alkyl constituent is substituted (i.e., —O—(substituted heterocycloalkyl)) wherein "substituted heterocycloalkyl" is as described herein.

The term "substituted amino" refers to the group —NHRd or —NRdRd where each Rd is independently chosen from: hydroxy, optionally substituted alkyl, optionally substituted cycloalkyl, optionally substituted acyl, aminocarbonyl, optionally substituted aryl, optionally substituted heteroaryl, optionally substituted heterocycloalkyl, alkoxycarbonyl, sulfinyl and sulfonyl, each as described herein, and provided that only one Rd may be hydroxyl. The term "substituted amino" also refers to N-oxides of the groups —NHRd, and NRdRd each as described above. N-oxides can be prepared by treatment of the corresponding amino group with, for example, hydrogen peroxide or m-chloroperoxybenzoic acid. The person skilled in the art is familiar with reaction conditions for carrying out the N-oxidation.

Compounds described herein include, but are not limited to, their optical isomers, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, such compounds include Z- and E-forms (or cis- and trans-forms) of compounds with carbon-carbon double bonds. Where compounds described herein exist in various tautomeric forms, chemical entities include all tautomeric forms of the compound. Such compounds also include crystal forms including polymorphs and clathrates.

Compounds of Formula I also include crystalline and amorphous forms of those compounds, including, for example, polymorphs, pseudopolymorphs, solvates, hydrates, unsolvated polymorphs (including anhydrates), conformational polymorphs, and amorphous forms of the compounds, as well as mixtures thereof "Crystalline form," "polymorph," and "novel form" may be used interchangeably herein, and are meant to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to. Compounds of Formula I also include pharmaceutically acceptable forms of the recited compounds, including chelates, non-covalent complexes, prodrugs, and mixtures thereof.

Compounds of Formula I also include different enriched isotopic forms, e.g., compounds enriched in the content of 2H, 3H, 11C, 13C and/or 14C. In some embodiments, the compounds are deuterated. Such deuterated forms can be made by the procedure described in U.S. Pat. Nos. 5,846,514 and 6,334,997. As described in U.S. Pat. Nos. 5,846,514 and 6,334,997, deuteration may improve the efficacy and increase the duration of action of drugs.

Deuterium substituted compounds can be synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] 2000, 110; Kabalka, George W.; Varma, Rajender S. The Synthesis of Radiolabeled Compounds via Organometallic Intermediates, Tetrahedron, 1989, 45(21), 6601-21, and Evans, E. Anthony. Synthesis of radiolabeled compounds, J. Radioanal. Chem., 1981, 64(1-2), 9-32.

Chemical entities include, but are not limited to compounds described herein and all pharmaceutically acceptable forms thereof. Hence, the terms "chemical entity" and "chemical entities" also encompass pharmaceutically acceptable salts.

"Pharmaceutically acceptable salts" include, but are not limited to salts with inorganic acids, such as hydrochlorate, phosphate, diphosphate, hydrobromate, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, HOOC—$(CH_2)$n-COOH where n is 0-4, and like salts. Similarly, pharmaceutically acceptable cations include, but are not limited to sodium, potassium, calcium, aluminum, lithium, and ammonium.

In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

As noted above, prodrugs also fall within the scope of compounds of Formula I. In some embodiments, the "prodrugs" described herein include any compound that becomes a compound of Formula I when administered to a patient, e.g., upon metabolic processing of the prodrug. Examples of prodrugs include derivatives of functional groups, such as a carboxylic acid group, in the compounds of Formula I. Exemplary prodrugs of a carboxylic acid group include, but are not limited to, carboxylic acid esters such as alkyl esters, hydroxyalkyl esters, arylalkyl esters, and aryloxyalkyl esters.

A "solvate" is formed by the interaction of a solvent and a compound. The term "compound" is intended to include solvates of compounds. Similarly, "salts" includes solvates of salts. Suitable solvates are pharmaceutically acceptable solvates, such as hydrates, including monohydrates and hemi-hydrates.

A "chelate" is formed by the coordination of a compound to a metal ion at two (or more) points. The term "compound" is intended to include chelates of compounds. Similarly, "salts" includes chelates of salts.

A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding). Such non-covalent complexes are included in the term "compound'.

The term "hydrogen bond" refers to a form of association between an electronegative atom (also known as a hydrogen bond acceptor) and a hydrogen atom attached to a second, relatively electronegative atom (also known as a hydrogen bond donor). Suitable hydrogen bond donor and acceptors are well understood in medicinal chemistry (G. C. Pimentel and A. L. McClellan, The Hydrogen Bond, Freeman, San Francisco, 1960; R. Taylor and O. Kennard, "Hydrogen Bond Geometry in Organic Crystals", Accounts of Chemical Research, 17, pp. 320-326 (1984)).

"Hydrogen bond acceptor" refers to a group comprising an oxygen or nitrogen, especially an oxygen or nitrogen that is sp2-hybridized, an ether oxygen, or the oxygen of a sulfoxide or N-oxide.

The term "hydrogen bond donor" refers to an oxygen, nitrogen, or heteroaromatic carbon that bears a hydrogen-.group containing a ring nitrogen or a heteroaryl group containing a ring nitrogen.

As used herein the terms "group", "radical" or "fragment" are synonymous and are intended to indicate functional groups or fragments of molecules attachable to a bond or other fragments of molecules.

The term "active agent" is used to indicate a chemical entity which has biological activity. In some embodiments, an "active agent" is a compound having pharmaceutical utility. For example an active agent may be an anti-cancer therapeutic.

The term "therapeutically effective amount" of a chemical entity described herein means an amount effective, when administered to a human or non-human patient, to provide a therapeutic benefit such as amelioration of symptoms, slowing of disease progression, or prevention of disease e.g., a therapeutically effective amount may be an amount sufficient to decrease the symptoms of a disease responsive to inhibition of Syk activity. In some embodiments, a therapeutically effective amount is an amount sufficient to reduce cancer symptoms, the symptoms of an allergic disorder, the symptoms of an autoimmune and/or inflammatory disease, or the symptoms of an acute inflammatory reaction. In some embodiments a therapeutically effective amount is an amount sufficient to decrease the number of detectable cancerous cells in an organism, detectably slow, or stop the growth of a cancerous tumor. In some embodiments, a therapeutically effective amount is an amount sufficient to shrink a cancerous tumor. In some embodiments, a patient suffering from cancer may not present symptoms of being affected. In some embodiments, a therapeutically effective amount of a chemical entity is an amount sufficient to prevent a significant increase or significantly reduce the detectable level of cancerous cells or cancer markers in the patient's blood, serum, or tissues. In some embodiments, a therapeutically effective amount may also be an amount sufficient, when administered to a patient, to detectably slow progression of the disease, or prevent the patient to whom the chemical entity is given from presenting symptoms of the allergic disorders and/or autoimmune and/or inflammatory disease, and/or acute inflammatory response. In some embodiments, a therapeutically effective amount may also be an amount sufficient to produce a detectable decrease in the amount of a marker protein or cell type in the patient's blood or serum. In some embodiments a therapeutically effective amount is an amount of a chemical entity described herein sufficient to significantly decrease the activity of B-cells. In some embodiments, a therapeutically effective amount is an amount of a chemical entity described herein sufficient to decrease the level of anti-acetylcholine receptor antibody in a patient's blood with the disease myasthenia gravis.

The term "inhibition" indicates a significant decrease in the baseline activity of a biological activity or process. "Inhibition of Syk activity" refers to a decrease in Syk activity as a direct or indirect response to the presence of at least one chemical entity described herein, relative to the activity of Syk in the absence of the at least one chemical entity. The decrease in activity may be due to the direct interaction of the compound with Syk, or due to the interaction of the chemical entity(ies) described herein with one or more other factors that in turn affect Syk activity. For example, the presence of the chemical entity(ies) may decrease Syk activity by directly binding to the Syk, by causing (directly or indirectly) another factor to decrease Syk activity, or by (directly or indirectly) decreasing the amount of Syk present in the cell or organism.

Inhibition of Syk activity also refers to observable inhibition of Syk activity in a standard biochemical assay for Syk activity, such as the ATP hydrolysis assay described below. In some embodiments, the chemical entity described herein has an IC50 value less than or equal to 1 micromolar. In some embodiments, the chemical entity has an IC50 value less than or equal to less than 100 nanomolar. In some embodiments, the chemical entity has an IC50 value less than or equal to 10 nanomolar.

"Inhibition of B-cell activity" refers to a decrease in B-cell activity as a direct or indirect response to the presence of at least one chemical entity described herein, relative to the activity of B-cells in the absence of the at least one chemical entity. The decrease in activity may be due to the direct interaction of the compound with Syk or with one or more other factors that in turn affect B-cell activity.

Inhibition of B-cell activity also refers to observable inhibition of CD86 expression in a standard assay such as the assay described below. In some embodiments, the chemical entity described herein has an IC50 value less than or equal to 10 micromolar. In some embodiments, the chemical entity has an IC50 value less than or equal to less than 1 micromolar. In some embodiments, the chemical entity has an IC50 value less than or equal to 500 nanomolar.

"B-cell activity" also includes activation, redistribution, reorganization, or capping of one or more various B-cell membrane receptors, or membrane-bound immunoglobulins, e.g, IgM, IgG, and IgD. Most B-cells also have membrane receptors for Fc portion of IgG in the form of either antigen-antibody complexes or aggregated IgG. B-cells also carry membrane receptors for the activated components of complement, e.g., C3b, C3d, C4, and C1q. These various membrane receptors and membrane-bound immunoglobulins have membrane mobility and can undergo redistribution and capping that can initiate signal transduction.

B-cell activity also includes the synthesis or production of antibodies or immunoglobulins. Immunoglobulins are synthesized by the B-cell series and have common structural features and structural units. Five immunoglobulin classes, i.e., IgG, IgA, IgM, IgD, and IgE, are recognized on the basis of structural differences of their heavy chains including the amino acid sequence and length of the polypeptide chain. Antibodies to a given antigen may be detected in all or several classes of immunoglobulins or may be restricted to a single class or subclass of immunoglobulin. Autoantibodies or autoimmune antibodies may likewise belong to one or several classes of immunoglobulins. For example, rheumatoid factors (antibodies to IgG) are most often recognized as an IgM imnnunoglobulin, but can also consist of IgG or IgA.

In addition, B-cell activity also is intended to include a series of events leading to B-cell clonal expansion (proliferation) from precursor B lymphocytes and differentiation into antibody-synthesizing plasma cells which takes place in conjunction with antigen-binding and with cytokine signals from other cells.

"Inhibition of B-cell proliferation" refers to inhibition of proliferation of abnormal B-cells, such as cancerous B-cells, e.g. lymphoma B-cells and/or inhibition of normal, non-diseased B-cells. The term "inhibition of B-cell proliferation" indicates any significant decrease in the number of B-cells, either in vitro or in vivo. Thus an inhibition of B-cell proliferation in vitro would be any significant decrease in the number of B-cells in an in vitro sample contacted with at least one chemical entity described herein as compared to a matched sample not contacted with the chemical entity(ies).

Inhibition of B-cell proliferation also refers to observable inhibition of B-cell proliferation in a standard thymidine incorporation assay for B-cell proliferation, such as the assay described herein. In some embodiments, the chemical entity has an IC50 value less than or equal to 10 micromolar. In some embodiments, the chemical entity has an IC50 value less than or equal to less than 1 micromolar. In some embodiments, the chemical entity has an IC50 value less than or equal to 500 nanomolar.

An "allergy" or "allergic disorder" refers to acquired hypersensitivity to a substance (allergen). Allergic conditions include eczema, allergic rhinitis or coryza, hay fever, bronchial asthma, urticaria (hives) and food allergies, and other atopic conditions.

"Asthma" refers to a disorder of the respiratory system characterized by inflammation, narrowing of the airways and increased reactivity of the airways to inhaled agents. Asthma is frequently, although not exclusively associated with atopic or allergic symptoms.

By "significant" is meant any detectable change that is statistically significant in a standard parametric test of statistical significance such as Student's T-test, where $p < 0.05$.

A "disease responsive to inhibition of Syk activity" is a disease in which inhibiting Syk kinase provides a therapeutic benefit such as an amelioration of symptoms, decrease in disease progression, prevention or delay of disease onset, or inhibition of aberrant activity of certain cell-types (monocytes, B-cells, and mast cells).

"Treatment" or "treating" means any treatment of a disease in a patient, including:

a) preventing the disease, that is, causing the clinical symptoms of the disease not to develop;

b) inhibiting the disease;

c) slowing or arresting the development of clinical symptoms;

and/or d) relieving the disease, that is, causing the regression of clinical symptoms.

"Patient" refers to an animal, such as a mammal, that has been or will be the object of treatment, observation or experiment. The methods described herein may be useful in both human therapy and veterinary applications. In some embodiments, the patient is a mammal; in some embodiments the patient is human; and in some embodiments the patient is chosen from cats and dogs.

Nomenclature

Names of compounds of the present invention are provided using ACD/Name software for naming chemical compounds (Advanced Chemistry Development, Inc., Toronto). Other compounds or radicals may be named with common names, or systematic or non-systematic names. The naming and numbering of the compounds of the invention is illustrated with a representative compound of Formula I:

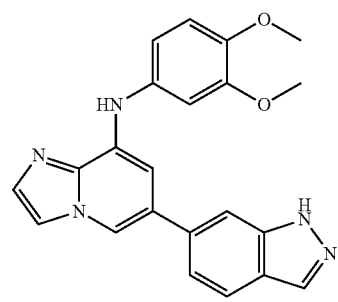 [SMILES: COc1ccc(Nc2cc(-c3ccc4cn[nH]c4c3)cn3ccnc23)cc1OC]

which is named N-(3,4-dimethoxyphenyl)-6-(1H-indazol-6-yl)imidazo[1,2-a]pyridin-8-amine.

Compounds of Formula I

Accordingly, in typical embodiments the present invention provides compounds that function as Syk inhibitors. In typical embodiments the invention relates to compounds of Formula I:

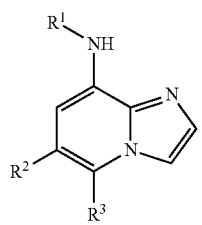

(I)

and pharmaceutically acceptable salts thereof, wherein
$R^1$ is chosen from phenyl, pyridinyl, pyrimidinyl, pyridazinyl, pyrazolyl, and thiazolyl, each of which is optionally substituted, and each of which is further optionally fused to a heterocyclic or heteroaryl group, each of which is optionally substituted,
$R^2$ is chosen from substituted aryl and optionally substituted heteroaryl; and
$R^3$ is chosen from hydrogen, lower alkyl, halogen, carboxamido or $CO_2H$, provided that if $R^2$ is 3-(4-(tert-butyl)benzamido)-2-methylphenyl, then $R^3$ is lower alkyl, provided that if $R^1$ is 5-(morpholine-4-carbonyl)-pyridin-2-yl, then $R^3$ is lower alkyl; and,
further provided that the compound of Formula I is not 6-(6-phenyl-imidazo[1,2-a]pyridin-8-ylamino)-nicotinic acid ethyl ester or (6-phenyl-imidazo[1,2-a]pyridin-8-yl)-pyridin-2-yl-amine.

In some embodiments, $R^1$ is chosen from phenyl, pyridinyl, pyrimidinyl, pyridazinyl, pyrazolyl, and thiazolyl, each of which is optionally substituted with one or more groups chosen from
hydroxy;
—$NR^bR^c$ wherein $R^b$ is chosen from hydrogen and $C_1$-$C_6$ alkyl optionally substituted with one or two groups chosen from hydroxy and —$OC_1$-$C_4$ alkyl and $R^c$ is independently chosen from hydrogen and $C_1$-$C_4$ alkyl optionally substituted with one or two groups chosen from hydroxy and —$OC_1$-$C_4$ alkyl;
heterocycloalkyl optionally substituted with one or two groups chosen from hydroxy, $C_3$-$C_6$ cycloalkyl, $C_1$-$C_4$ alkyl, —$C_1$-$C_4$ alkyl-OH, —$C_1$-$C_4$ alkyl-O—$C_1$-$C_4$ alkyl, —$C_1$-$C_4$ alkyl-$NH_2$, —$N(C_1$-$C_4$ alkyl)($C_1$-$C_4$ alkyl), —$NH(C_1$-$C_4$ alkyl), —$C(O)(C_1$-$C_4$ alkyl), —$C(O)(C_1$-$C_4$ alkyl-OH), and —$OC_1$-$C_4$ alkyl;
—$OC_1$-$C_6$ alkyl optionally substituted with one or two groups chosen from hydroxy, $C_3$-$C_6$ cycloalkyl, $C_1$-$C_4$ alkyl, —$C_1$-$C_4$ alkyl-OH, —$C_1$-$C_4$ alkyl-O—$C_1$-$C_4$ alkyl, —$C_1$-$C_4$ alkyl-$NH_2$, —$N(C_1$-$C_4$ alkyl)($C_1$-$C_4$ alkyl), —$NH(C_1$-$C_4$ alkyl), and —$OC_1$-$C_4$ alkyl; and
$C_1$-$C_6$ alkyl optionally substituted with one or two groups chosen from hydroxy, $C_3$-$C_6$ cycloalkyl, $C_1$-$C_4$ alkyl, —$C_1$-$C_4$ alkyl-OH, —$C_1$-$C_4$ alkyl-O—$C_1$-$C_4$ alkyl, —$C_1$-$C_4$ alkyl-$NH_2$, —$N(C_1$-$C_4$ alkyl)($C_1$-$C_4$ alkyl), —$NH(C_1$-$C_4$ alkyl), and —$OC_1$-$C_4$ alkyl.

In some embodiments, $R^1$ is chosen from pyridinyl, pyrimidinyl, pyridazinyl, pyrazolyl, and thiazolyl, each of which is optionally substituted with one or more groups chosen from:
hydroxy;
—$NR^bR^c$ wherein $R^b$ is chosen from hydrogen and $C_1$-$C_6$ alkyl optionally substituted with one or two groups chosen from hydroxy and —$OC_1$-$C_4$ alkyl and $R^c$ is independently chosen from hydrogen and $C_1$-$C_4$ alkyl optionally substituted with one or two groups chosen from hydroxy and —$OC_1$-$C_4$ alkyl;
heterocycloalkyl optionally substituted with one or two groups chosen from hydroxy, —$OC_1$-$C_4$ alkyl, —$C_1$-$C_4$ alkyl-OH, and $C_1$-$C_4$ alkyl;
—$OC_1$-$C_6$ alkyl optionally substituted with one or two groups chosen from hydroxy, —$OC_1$-$C_4$ alkyl, —$NH_2$, —$N(C_1$-$C_4$ alkyl)H, and —$N(C_1$-$C_4$ alkyl)($C_1$-$C_4$ alkyl); and $C_1$-$C_6$ alkyl optionally substituted with hydroxy.

In some embodiments, $R^1$ is chosen from; 3,4-dimethoxyphenyl, 4-(1-hydroxy-2-methylpropan-2-yl)phenyl, 5,6-dimethoxypyridin-2-yl, 5-(morpholin-4-yl)pyridin-2-yl, (R)-5-(2-(hydroxymethyl)morpholino)pyridin-2-yl, (S)-5-(2-(hydroxymethyl)morpholino)pyridin-2-yl, 6-aminopyridin-2-yl, 5-(4-hydroxy-4-methylpiperidin-1-yl)pyridin-2-yl, 5-((2-hydroxyethyl)(methyl)amino)pyridin-2-yl, 5-((2-methoxyethyl)(methyl)amino)pyridin-2-yl, 5-(3-hydroxyazetidin-1-yl)pyridin-2-yl, 5-(3-hydroxy-3-methylazetidin-1-yl)pyridin-2-yl, 5-(2-hydroxy-2-methylpropoxy)pyridin-2-yl, 5-(ethyl(2-hydroxyethyl)amino)pyridin-2-yl, 5-(4-acetylpiperazin-1-yl)pyridin-2-yl, 5-(4-(2-hydroxyacetyl)piperazin-1-yl)pyridin-2-yl, 5-(4-ethylpiperazin-1-yl)pyridin-2-yl, pyrimidin-4-yl, 2-methoxypyrimidin-4-yl, 1-methyl-1H-pyrazol-3-yl, 1-ethyl-1H-pyrazol-3-yl, 1-ethyl-5-methyl-1H-pyrazol-3-yl, 1,5-dimethyl-1H-pyrazol-3-yl, 1-(2-hydroxyethyl)-5-methyl-1H-pyrazol-3-yl, 5-(hydroxymethyl)-1-methyl-1H-pyrazol-3-yl, 6-(morpholin-4-yl)pyridazin-3-yl, and 2-morpholinothiazol-4-yl.

In some embodiments, $R^1$ is chosen from phenyl, pyridinyl, pyrimidinyl, pyridazinyl, pyrazolyl, and thiazolyl, each of which is optionally substituted and each of which is fused to a heterocyclic or heteroaryl group and each of which is optionally substituted.

In some embodiments, $R^1$ is optionally substituted pyrazolyl fused to a heterocyclic or heteroaryl group, each of which is optionally substituted.

In some embodiments, $R^1$ is chosen from 6,7-dihydro-4H-pyrazolo[5,1-c][1,4]oxazin-2-yl, 5-acetyl-4,5,6,7-tetrahydropyrazolo[1,5-a]pyrazin-2-yl, and 5-methanesulfonyl-4H,5H,6H,7H-pyrazolo[1,5-a]pyrazin-2-yl.

In some embodiments, $R^2$ is chosen from optionally substituted heteroaryl, dihydroindolyl optionally substituted with oxo and C1-C6 alkyl, and dihydrobenzoxazinyl optionally substituted with oxo.

In some embodiments, $R^2$ is chosen from 2,3-dimethyl-2H-indazol-6-yl, 1H-indazolyl-6-yl, 1-methyl-1H-indazol-5-yl, 1-methyl-1H-indazol-6-yl, 3,4-dihydro-2H-1,4-benzoxazin-3-one-6-yl, 1-(2-hydroxyethyl)-1H-benzo[d]imidazol-2(3H)-one-5-yl, 3-amino-1H-indazol-6-yl, 1H-pyrrolo[3,2-b]pyridine-6-yl, 1,3-benzoxazol-6-yl, 3,4-dihydro-2H-1,4-benzoxazin-6-yl, 2-hydroxyquinoxalin-7-yl, 3-aminoquinolin-6-yl, 2,3-dihydro-1H-indol-6-yl, 1H,2H,3H-pyrido[2,3-b][1,4]oxazin-2-one, (3-hydroxyethyl)-1H-indol-6-yl, benzothiazolyl, 2-aminoquinazolin-6-yl, 3,3-dimethylindolin-2-one, 2,3-dihydro-1H-indol-2-one, 4-fluoro-1H-indazol-6-yl, 5-fluoro-1H-indazol-6-yl, and 3-amino-1H-indazol-6-yl.

In some embodiments, $R^2$ is chosen from 1H-indazolyl-6-yl, 1-methyl-1H-indazol-5-yl, 1-methyl-1H-indazol-6-yl, 3,4-dihydro-2H-1,4-benzoxazin-3-one-6-yl, 1,3-benzoxazol-6-yl, 3-aminoquinolin-6-yl, 1H-pyrrolo[3,2-b]pyridin-6-yl, and 2,3-dihydro-1H-indol-2-one-6-yl.

In some embodiments, $R^3$ is chosen from hydrogen and methyl.

In some embodiments, $R^3$ is hydrogen.

In all of the foregoing examples, the chemical entities can be administered alone, as mixtures, or in combination with other active agents.

General Syntheses:

The compounds of the invention may be prepared using methods disclosed herein and routine modifications thereof which will be apparent given the disclosure herein and methods well known in the art. Conventional and well-known synthetic methods may be used in addition to the teachings herein. The synthesis of typical compounds described herein, e.g. compounds having structures described by one or more of Formula I, may be accomplished as described in the following examples.

Typical embodiments of compounds in accordance with the present invention may be synthesized using the general reaction scheme described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection.

Starting materials are typically obtained from commercial sources or synthesized using published methods. For synthesizing compounds which are embodiments of the present invention, inspection of the structure of the compound to be synthesized will provide the identity of each substituent group. The identity of the final product will generally render apparent the identity of the necessary starting materials by a simple process of inspection, given the examples herein.

As a general method, the compounds of the invention are typically synthesized by reacting a di-halogeniated core (A) with an amino derivative of the desired $R^1$ moiety (B) to provide an $R^1$ substituted intermediate (C). This intermediate (C) is then reacted with an appropriately substituted boronic acid or dioxaborolane derivative (D), thereby coupling the desired $R^2$ moiety onto the $R^1$ coupled core. When the reaction is substantially complete, the product of Formula I is isolated by conventional means.

REACTION SCHEME 1

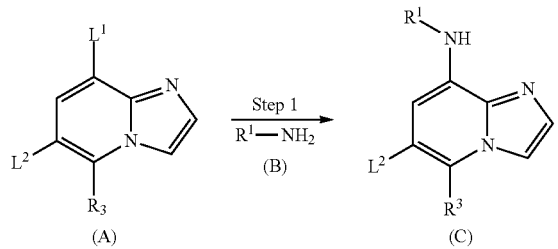

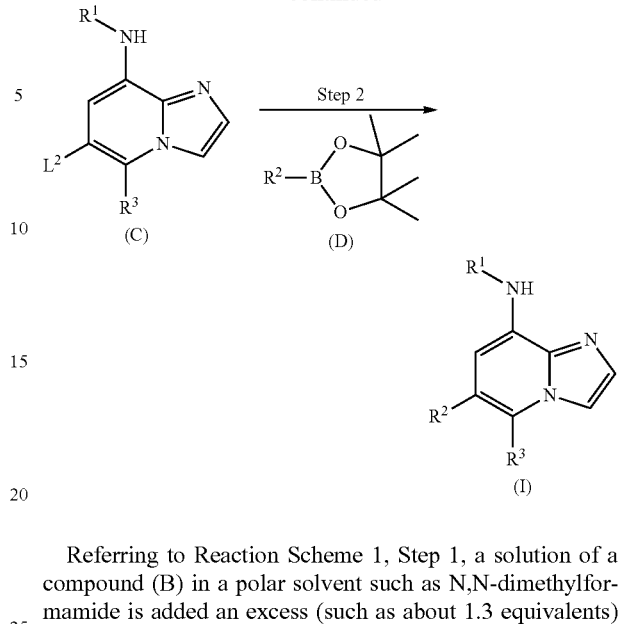

Referring to Reaction Scheme 1, Step 1, a solution of a compound (B) in a polar solvent such as N,N-dimethylformamide is added an excess (such as about 1.3 equivalents) to a compound (A), where $L^1$ and $L^2$ and leaving groups which may be the same or different such as bromide and/or chloride. An organic base such as N,N-diisopropylethylamine is added and the mixture is stirred at about 80° C.-120° C. for about 12-24 hours. The product, compound (C), is isolated and optionally purified.

Referring to Reaction Scheme 1, Step 2, an excess of compound (D) (such as about 1.1 equivalents) and compound (C) are taken up in an aqueous solution of base (such as 1M sodium carbonate) and an inert solvent such as 1,4-dioxane. The reaction mixture is sparged with nitrogen and stirred for about 5-20 min. The resulting mixture is treated with about 0.1 equivalent of tetrakis(triphenylphosphine)palladium(0) and reacted under microwave irradiation at about 110° C. to 135° C. for about 30 min to an hour. The resulting product, a compound of Formula I, is isolated and optionally purified.

Compounds of formulas (B) and (D) may be commercially obtained or may be synthesized de novo. It will be appreciated that various R subsitutents can be modified or added either before or after the addition of the $R^1$ and/or $R^2$ moieties. For example, in certain embodiments, the $R^2$ moiety may be coupled to the core before addition of the $R^1$ substituent. Also, in the case where the $R^1$ substituent contains a heteroaryl ring, the ring may be synthesized and cyclized before or after addition of the $R^1$ portion.

It will also be appreciated that the addition of any substituent may result in the production of a number of isomeric products any or all of which may be isolated and purified using conventional techniques.

Optional Core Synthesis

When the core compound (A) is synthesized de novo, the $R^3$ components of the compounds are typically established by selecting the appropriate reactants for core synthesis. Additional modification to provide a desired $R^3$ substituent may be introduced using conventional techniques as illustrated in the examples that follow.

Further Embodiments

Accordingly, provided is a method of treating a patient, for example, a mammal, such as a human, having a disease responsive to inhibition of Syk activity, comprising administrating to the patient having such a disease, an effective amount of at least one chemical entity described herein.

In some embodiments, the chemical entities described herein may also inhibit other kinases, such that disease, disease symptoms, and conditions associated with these kinases is also treated.

Methods of treatment also include inhibiting Syk activity and/or inhibiting B-cell activity, by inhibiting ATP binding or hydrolysis by Syk or by some other mechanism, in vivo, in a patient suffering from a disease responsive to inhibition of Syk activity, by administering an effective concentration of at least one chemical entity chosen described herein. An example of an effective concentration would be that concentration sufficient to inhibit Syk activity in vitro. An effective concentration may be ascertained experimentally, for example by assaying blood concentration of the chemical entity, or theoretically, by calculating bioavailability.

In some embodiments, the condition responsive to inhibition of Syk activity and/or B-cell activity is cancer, an allergic disorder and/or an autoimmune and/or inflammatory disease, and/or an acute inflammatory reaction.

Also provided is a method of treating a patient having cancer, an allergic disorder and/or an autoimmune and/or inflammatory disease, and/or an acute inflammatory reaction, by administering an effective amount of at least one chemical entity described herein.

In some embodiments, the conditions and diseases that can be affected using chemical entities described herein, include, but are not limited to: allergic disorders, including but not limited to eczema, allergic rhinitis or coryza, hay fever, bronchial asthma, urticaria (hives) and food allergies, and other atopic conditions; autoimmune and/or inflammatory diseases, including but not limited to psoriasis, Crohn's disease, irritable bowel syndrome, Sjogren's disease, tissue graft rejection, and hyperacute rejection of transplanted organs, asthma, systemic lupus erythematosus (and associated glomerulonephritis), dermatomyositis, multiple sclerosis, scleroderma, vasculitis (ANCA-associated and other vasculitides), autoimmune hemolytic and thrombocytopenic states, Goodpasture's syndrome (and associated glomerulonephritis and pulmonary hemorrhage), atherosclerosis, rheumatoid arthritis, chronic Idiopathic thrombocytopenic purpura (ITP), Addison's disease, Parkinson's disease, Alzheimer's disease, diabetes, septic shock, myasthenia gravis, and the like; acute inflammatory reactions, including but not limited to skin sunburn, inflammatory pelvic disease, inflammatory bowel disease, urethritis, uvitis, sinusitis, pneumonitis, encephalitis, meningitis, myocarditis, nephritis, osteomyelitis, myositis, hepatitis, gastritis, enteritis, dermatitis, gingivitis, appendicitis, pancreatitis, and cholocystitis; polycystic kidney disease, and cancer, including but not limited to, B-cell lymphoma, lymphoma (including Hodgkin's and non-Hodgkins lymphoma), hairy cell leukemia, multiple myeloma, chronic and acute myelogenous leukemia, and chronic and acute lymphocytic leukemia.

Syk is a known inhibitor of apoptosis in lymphoma B-cells. Defective apoptosis contributes to the pathogenesis and drug resistance of human leukemias and lymphomas. Thus, further provided is a method of promoting or inducing apoptosis in cells expressing Syk comprising contacting the cell with at least one chemical entity described herein.

Combination Therapy

Also provided are methods of treatment in which at least one chemical entity described herein is the only active agent given to a patient and also includes methods of treatment in which at least one chemical entity described herein is given to a patient in combination with one or more additional active agents.

Thus in some embodiments, a method of treating cancer, an allergic disorder and/or an autoimmune and/or inflammatory disease, and/or an acute inflammatory reaction comprises administering to a patient in need thereof an effective amount of at least one chemical entity described herein, together with a second active agent, which can be useful for treating a cancer, an allergic disorder and/or an autoimmune and/or inflammatory disease, and/or an acute inflammatory reaction. For example the second agent may be an anti-inflammatory agent. Treatment with the second active agent may be prior to, concomitant with, or following treatment with at least one chemical entity described herein. In some embodiments, at least one chemical entity described herein is combined with another active agent in a single dosage form. Suitable antitumor therapeutics that may be used in combination with at least one chemical entity described herein include, but are not limited to, chemotherapeutic agents, for example mitomycin C, carboplatin, taxol, cisplatin, paclitaxel, etoposide, doxorubicin, or a combination comprising at least one of the foregoing chemotherapeutic agents. Radiotherapeutic antitumor agents may also be used, alone or in combination with chemotherapeutic agents.

Chemical entities described herein can be useful as chemosensitizing agents, and, thus, can be useful in combination with other chemotherapeutic drugs, in particular, drugs that induce apoptosis.

A method for increasing sensitivity of cancer cells to chemotherapy, comprising administering to a patient undergoing chemotherapy a chemotherapeutic agent together with at least one chemical entity described herein in an amount sufficient to increase the sensitivity of cancer cells to the chemotherapeutic agent is also provided herein.

Examples of other chemotherapeutic drugs that can be used in combination with chemical entities described herein include topoisomerase I inhibitors (camptothesin or topotecan), topoisomerase II inhibitors (e.g. daunomycin and etoposide), alkylating agents (e.g. cyclophosphamide, melphalan and BCNU), tubulin directed agents (e.g. taxol and vinblastine), and biological agents (e.g. antibodies such as anti CD20 antibody, IDEC 8, immunotoxins, and cytokines).

In some embodiments, the chemical entities described herein are used in combination with Rituximab or other agents that work by selectively depleting CD20+B-cells.

Included herein are methods of treatment in which at least one chemical entity described herein is administered in combination with an anti-inflammatory agent. Anti-inflammatory agents include but are not limited to NSAIDs, non-specific and COX-2 specific cyclooxgenase enzyme inhibitors, gold compounds, corticosteroids, methotrexate, tumor necrosis factor receptor (TNF) receptors antagonists, immunosuppressants and methotrexate.

Examples of NSAIDs include, but are not limited to ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors (i.e., a compound that inhibits COX-2 with an IC50 that is at least 50-fold lower than the IC50 for COX-1) such as celecoxib, valdecoxib, lumiracoxib, etoricoxib and/or rofecoxib.

In some embodiments, the anti-inflammatory agent is a salicylate. Salicylates include but are not limited to acetylsalicylic acid or aspirin, sodium salicylate, and choline and magnesium salicylates.

The anti-inflammatory agent may also be a corticosteroid. For example, the corticosteroid may be chosen from cortisone, dexamethasone, methylprednisolone, prednisolone, prednisolone sodium phosphate, and prednisone.

In some embodiments, the anti-inflammatory therapeutic agent is a gold compound such as gold sodium thiomalate or auranofin.

In some embodiments, the anti-inflammatory agent is a metabolic inhibitor such as a dihydrofolate reductase inhibitor, such as methotrexate or a dihydroorotate dehydrogenase inhibitor, such as leflunomide.

In some embodiments, combinations in which at least one anti-inflammatory compound is an anti-C5 monoclonal antibody (such as eculizumab or pexelizumab), a TNF antagonist, such as entanercept, or infliximab, which is an anti-TNF alpha monoclonal antibody are used.

In some embodiments, combinations in which at least one active agent is an immunosuppressant compound such as methotrexate, leflunomide, cyclosporine, tacrolimus, azathioprine, or mycophenolate mofetil are used.

Pharmaceutical Compositions and Administration

Dosage levels of the order, for example, of from 0.1 mg to 140 mg per kilogram of body weight per day can be useful in the treatment of the above-indicated conditions (0.5 mg to 7 g per patient per day). The amount of active ingredient that may be combined with the vehicle to produce a single dosage form will vary depending upon the host treated and the particular mode of administration. Dosage unit forms will generally contain from 1 mg to 500 mg of an active ingredient.

Frequency of dosage may also vary depending on the compound used and the particular disease treated. In some embodiments, for example, for the treatment of an allergic disorder and/or autoimmune and/or inflammatory disease, a dosage regimen of 4 times daily or less is used. In some embodiments, a dosage regimen of 1 or 2 times daily is used. It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease in the patient undergoing therapy.

A labeled form of a chemical entity described herein can be used as a diagnostic for identifying and/or obtaining compounds that have the function of modulating an activity of a kinase as described herein. The chemical entities described herein may additionally be used for validating, optimizing, and standardizing bioassays.

By "labeled" herein is meant that the compound is either directly or indirectly labeled with a label which provides a detectable signal, e.g., radioisotope, fluorescent tag, enzyme, antibodies, particles such as magnetic particles, chemiluminescent tag, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

Compounds provided in accordance with the present invention are usually administered in the form of pharmaceutical compositions. This invention therefore provides pharmaceutical compositions that contain, as the active ingredient, one or more of the compounds described, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The pharmaceutical compositions may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.)

The pharmaceutical compositions may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parenteral, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound according to the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of compounds in accordance with the invention. Administration may be via capsule or enteric coated tablets, or the like. In making the pharmaceutical compositions that include at least one compound described herein, the active ingredient is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds are generally administered in a pharmaceutically effective amount. Preferably, for oral administration, each dosage unit contains from 1 mg to 2 g of a compound described herein, and for parenteral administration, preferably from 0.1 to 700 mg of a compound a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

EXAMPLES

The invention is further illustrated by the following non-limiting examples.

In the examples below, the following abbreviations have the following meanings. If an abbreviation is not defined, it has its generally accepted meaning.

DME=dimethyl ether
DMEM=Dulbecco's modified Eagle's medium
DMF=N,N-dimethylformamide
DMSO=dimethylsulfoxide
$Et_2O$=diethylether
g=gram
h=hour
mg=milligram
min=minutes
mL=milliliter
mmol=millimoles
mM=millimolar
ng=nanogram
nm=nanometer
nM=nanomolar
PBS=phosphate buffered saline
µL=microliter
µM=micromolar

Example 1

Preparation of N-{4H,6H,7H-pyrazolo[3,2-c][1,4]oxazin-2-yl}-6-{1H-pyrrolo[3,2-b]pyridin-6-yl}imidazo[1,2-a]pyridin-8-amine (1)

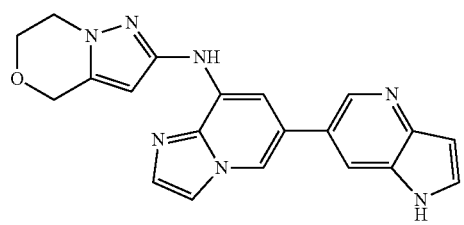

REACTION SCHEME 2

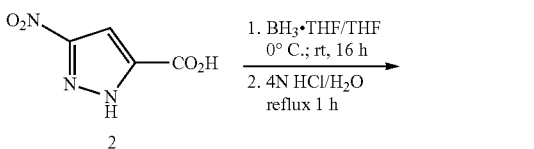

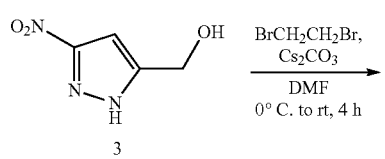

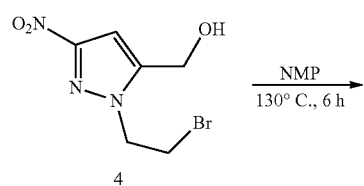

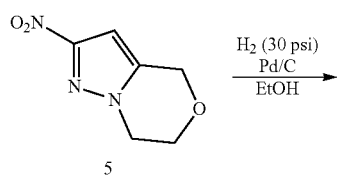

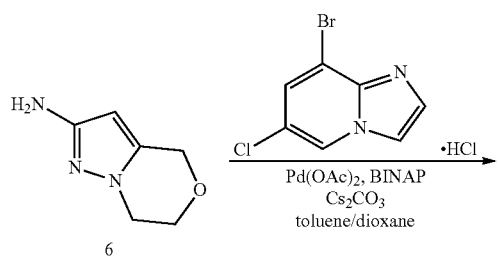

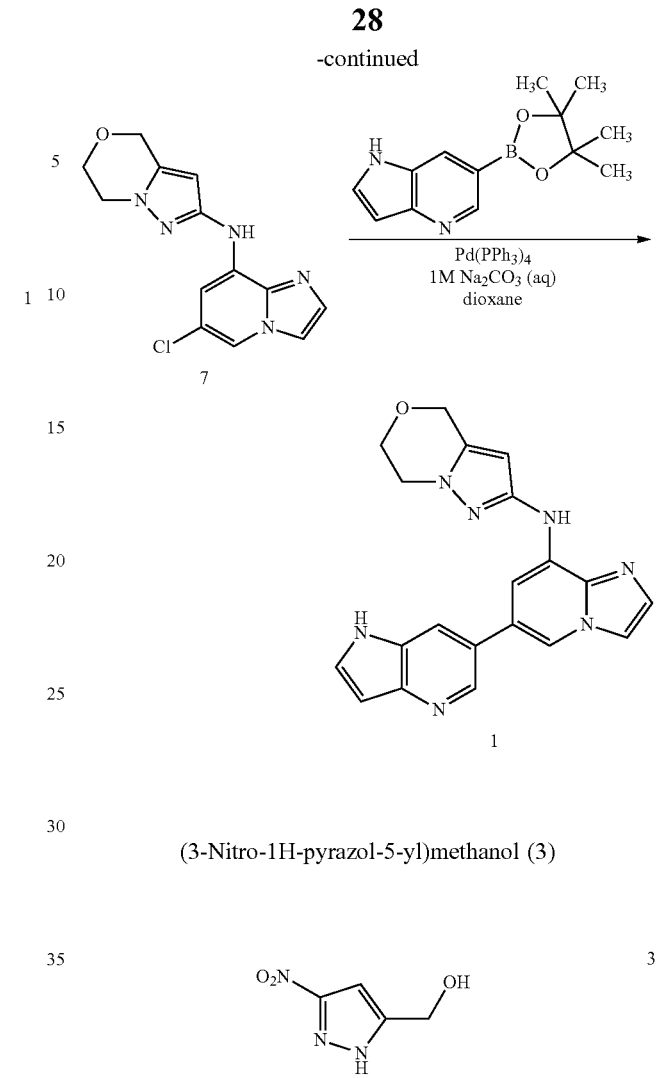

(3-Nitro-1H-pyrazol-5-yl)methanol (3)

A 3-L three-neck round-bottomed flask equipped with a mechanical stirrer, addition funnel and nitrogen inlet was purged with nitrogen and charged with 3-nitro-1H-pyrazole-5-carboxylic acid (2) (28.0 g, 178 mmol) and THF (420 mL) and cooled to −5° C. using an ice/acetone bath. Borane-THF complex solution (1.0 M, 535 mL, 535 mmol) was added at a rate that maintained the internal reaction temperature below 5° C. After the addition was complete the cooling bath was removed and the reaction was stirred at room temperature for 18 h. After this time the reaction was cooled to −5° C. using an ice/acetone bath, water (70 mL) and 4N hydrochloric acid (70 mL) was added and the reaction was stirred at reflux for 1 h in order to destroy the borane complex with pyrazole. The reaction was cooled to room temperature and concentrated under reduced pressure to a volume of approximately 30 mL. Ethyl acetate (175 mL) was added and the mixture stirred for 15 min. The aqueous layer was separated and extracted with ethyl acetate (4×200 mL). The combined organic layers were washed with saturated aqueous sodium bicarbonate (2×50 mL), brine (50 mL) and dried over sodium sulfate, the drying agent was removed by filtration, and the filtrate concentrated under reduced pressure to afford (3) as a light yellow solid: $^1$H NMR (300 MHz, DMSO-$d_6$) δ 13.90 (br s, 1H), 6.87 (s, 1H), 5.58 (t, 1H, J=5.4 Hz), 4.53 (d, 2H, J=5.1 Hz); MS (ESI+) m/z 144.0 (M+H).

(1-(2-Bromoethyl)-3-nitro-1H-pyrazol-5-yl)methanol (4)

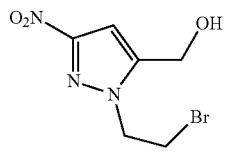

A 1-L three-necked round-bottomed flask equipped with a mechanical stirrer and thermoregulator was purged with nitrogen and charged with 3 (25.0 g, 175 mmol), DMF (250 mL), and cesium carbonate (70.0 g, 215 mmol) was heated at 104° C. for 5 min. The reaction mixture was then cooled to 0° C. using an ice/acetone bath and dibromoethane (329 g, 1.75 mol) was added portionwise (no exotherm). The reaction was stirred at 0° C. for 1 then at room temperature for 4 h. After this time a solution of $KH_2PO_4$ (40 g) in water (400 mL) was added slowly. The reaction mixture stirred at room temperature for 30 min. Ethyl acetate (450 mL) was added and the aqueous layer was separated and extracted with ethyl acetate (2×100 mL). The combined organic layers were washed with water (200 mL), brine (200 mL), dried over sodium sulfate, and the drying agent was removed by filtration. The filtrate was concentrated under reduced pressure to afford crude (4) as an orange oil: $^1$H NMR (300 MHz, $CDCl_3$) δ 6.85 (s, 1H), 4.82 (d, 2H, J=5.4 Hz), 4.66 (t, 2H, J=6.3 Hz), 3.83 (t, 2H, J=6.3 Hz); MS (ESI+) m/z 249.9 (M+H). This material was used in the following step directly.

Preparation of 2-nitro-6,7-dihydro-4H-pyrazolo[5,1-c][1,4]oxazine (5)

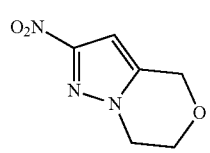

A solution of (1-(2-bromoethyl)-3-nitro-1H-pyrazol-5-yl) methanol (4) (650 mg, 2.60 mmol) in N-methylpyrrolidinone (1.5 mL) was stirred at 130° C. for 6 h. After this time, the reaction was cooled to room temperature, diluted with methylene chloride (50 mL) and washed with water (2×100 mL), then brine (100 mL). The combined organic layers were dried over sodium sulfate, filtered and the filtrate concentrated under reduced pressure. The resulting residue was purified by chromatography (silica, gradient, methylene chloride to 3:97 methanol/methylene chloride) to afford 2-nitro-6,7-dihydro-4H-pyrazolo[5,1-c][1,4]oxazine (5) as a white solid: $^1$H NMR (400 MHz, DMSO-$d_6$) δ 6.87 (s, 1H), 4.83 (s, 2H), 4.24 (t, J=5.6 Hz, 2H), 4.13 (t, J=5.6 Hz, 2H).

Preparation of 6,7-dihydro-4H-pyrazolo[5,1-c][1,4]oxazin-2-amine (6)

A 500-mL Parr hydrogenation bottle was purged with nitrogen and charged with 2-nitro-6,7-dihydro-4H-pyrazolo[5,1-c][1,4]oxazine(5) (250 mg, 1.48 mmol), ethanol (100 mL), and 10% palladium on carbon (50% wet, 50 mg dry weight). The bottle was evacuated, charged with hydrogen gas to a pressure of 30 psi and shaken for 30 min at room temperature on a Parr hydrogenation apparatus. After this time, the hydrogen was evacuated and nitrogen charged into the bottle. The catalyst was removed by filtration through a pad of Celite 521 and the filter cake washed with methanol (75 mL). The filtrate was concentrated under reduced pressure to afford 6,7-dihydro-4H-pyrazolo[5,1-c][1,4]oxazin-2-amine (6) as a light yellow oil: $^1$H NMR (400 MHz, DMSO-$d_6$) δ 5.26 (s, 1H), 5.20 (bs, 2H), 4.62 (s, 2H), 3.97 (t, J=4.8 Hz, 2H), 3.79 (t, J=4.8 Hz, 2H).

Preparation of N-(6-chloroimidazo[1,2-a]pyridin-8-yl)-6,7-dihydro-4H-pyrazolo[5,1-c][1,4]oxazin-2-amine(7)

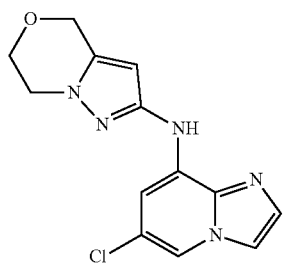

A mixture of 6,7-dihydro-4H-pyrazolo[5,1-c][1,4]oxazin-2-amine (6) (150 mg, 1.08 mmol), 8-bromo-6-chloroimidazo[1,2-a]pyridine hydrochloride salt (241 mg, 0.899 mmol), 2,2'-bis(diphenylphosphino)-1,1'-binaphthalene (112 mg, 0.180 mmol) and cesium carbonate (731 mg, 2.24 mmol) in toluene (6 mL) and 1,4-dioxane (3 mL) was sparged with nitrogen while stirring for 10 min. Palladium (II) acetate (22 mg, 0.098 mmol) was then added and the reaction stirred at 100° C. for 2.5 h. After this time, the reaction was cooled to room temperature, diluted with a mixture of 1:4 methanol/methylene chloride (100 mL) and filtered through diatomaceous earth. The filtrate was concentrated under reduced pressure and the resulting residue purified by chromatography (silica, gradient, methylene chloride to 3:97 methanol/methylene chloride) to afford N-(6-chloroimidazo[1,2-a]pyridin-8-yl)-6,7-dihydro-4H-pyrazolo[5,1-c][1,4]oxazin-2-amine (7) as an off-white solid: $^1$H NMR (400 MHz, $CDCl_3$) δ 7.69 (d, J=1.6 Hz, 1H), 7.61 (d, J=1.6 Hz, 1H), 7.50-7.49 (m, 2H), 7.47 (bs, 1H), 5.72 (s, 1H), 4.81 (s, 2H), 4.15-4.14 (m, 4H); ESI MS m/z 290.1 [M+H]$^+$.

Preparation of N-(6-(1H-pyrrolo[3,2-b]pyridin-6-yl)imidazo[1,2-a]pyridin-8-yl)-6,7-dihydro-4H-pyrazolo[5,1-c][1,4]oxazin-2-amine (1)

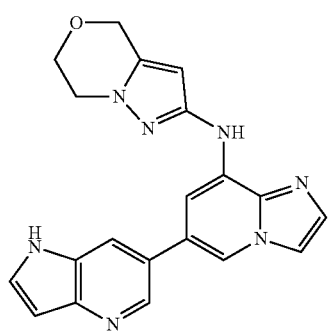

A mixture of N-(6-chloroimidazo[1,2-a]pyridin-8-yl)-6,7-dihydro-4H-pyrazolo[5,1-c][1,4]oxazin-2-amine (7) (67 mg, 0.23 mmol), 6-(4,4,5,5-tetramethyl-1,3,2-dioxaborolan-2-yl)-1H-pyrrolo[3,2-b]pyridine (85 mg, 0.35 mmol) and 1 M aqueous sodium carbonate (0.5 mL) in 1,4-dioxane (1.5 mL) was sparged with nitrogen while stirring for 5 min. Tetrakis(triphenylphosphine)palladium(0) (40 mg, 0.035 mmol) was then added and the reaction heated under microwave irradiation at 145° C. for 30 min. After this time, the reaction was cooled to room temperature, diluted with a mixture of 1:4 methanol/methylene chloride (75 mL) and filtered through diatomaceous earth. The filtrate was concentrated under reduced pressure and the resulting residue purified by chromatography (silica, gradient, methylene chloride to 1:9 methanol/methylene chloride), then trituration with acetonitrile, followed by trituration with ethyl acetate to afford N-(6-(1H-pyrrolo[3,2-b]pyridin-6-yl)imidazo[1,2-a]pyridin-8-yl)-6,7-dihydro-4H-pyrazolo[5,1-c][1,4]oxazin-2-amine (1) as a light yellow solid: mp 192-195° C.; $^1$H NMR (400 MHz, DMSO-$d_6$) δ 11.43 (bs, 1H), 8.86 (s, 1H), 8.62 (d, J=2.0 Hz, 1H), 8.35 (d, J=2.0 Hz, 1H), 8.09 (d, J=1.2 Hz, 1H), 7.95-7.93 (m, 2H), 7.70 (t, J=2.8 Hz, 1H), 7.54 (d, J=0.8 Hz, 1H), 6.60 (bs, 1H), 6.02 (s, 1H), 4.77 (s, 2H), 4.07-4.04 (m, 4H); ESI MS m/z 372.0 [M+H]$^+$; HPLC, 3.56 min, >99% (AUC).

Example 2

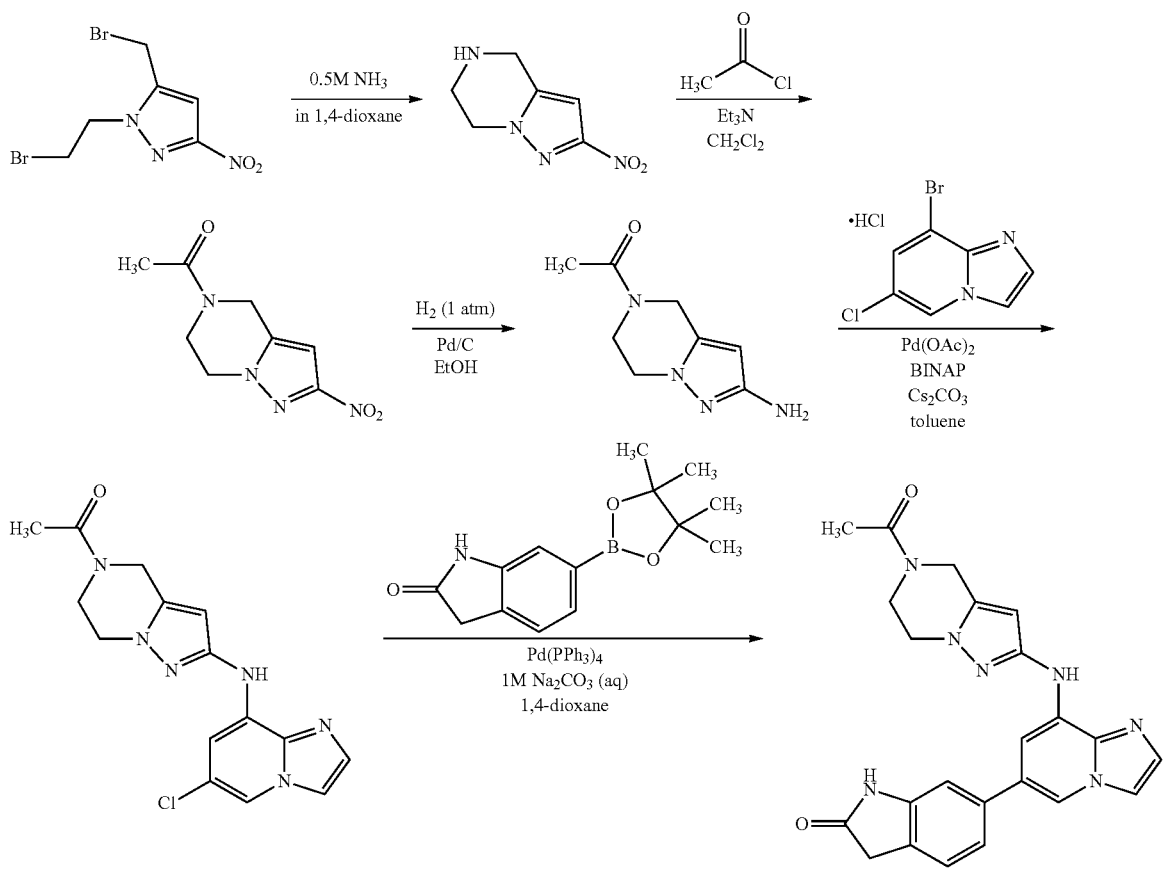

Preparation of 2-nitro-4,5,6,7-tetrahydropyrazolo[1,5-a]pyrazine

A solution of 1-(2-bromoethyl)-5-(bromomethyl)-3-nitro-1H-pyrazole (2.00 g, 6.39 mmol) and 0.5 M ammonia in 1,4-dioxane (100 mL) was stirred, in a sealed vessel, at 50° C. for 20 h. After this time, the reaction was concentrated under reduced pressure and the resulting residue purified by chromatography (silica, gradient, methylene chloride to 19:1 methylene chloride/methanol) to afford 2-nitro-4,5,6,7-tetrahydropyrazolo[1,5-a]pyrazine as a yellow solid: $^1$H NMR (400 MHz, DMSO-$d_6$) δ 6.79 (s, 1H), 4.06 (t, J=5.2 Hz, 2H), 3.91 (s, 2H), 3.15 (t, J=5.2 Hz, 2H), 2.78 (bs, 1H).

Preparation of 1-(2-nitro-6,7-dihydropyrazolo[1,5-a]pyrazin-5(4H)-yl)ethanone

A solution of 2-nitro-4,5,6,7-tetrahydropyrazolo[1,5-a]pyrazine (360 mg, 2.14 mmol) and triethylamine (650 mg, 6.42 mmol) in methylene chloride (16 mL) was treated dropwise with acetyl chloride (202 mg, 2.57 mmol) and the reaction was stirred at room temperature for 20 h. After this time, the reaction was concentrated under reduced pressure and the resulting residue partitioned between ethyl acetate (20 mL) and water (20 mL). The layers were separated and the aqueous phase extracted with ethyl acetate (20 mL). The combined organic layers were washed with brine (10 mL) and dried over sodium sulfate. The drying agent was removed by filtration and the filtrate concentrated under reduced pressure. The resulting residue was purified by chromatography (silica, gradient, methylene chloride to 49:1 methylene chloride/methanol) to afford 1-(2-nitro-6,7-dihydropyrazolo[1,5-a]pyrazin-5(4H)-yl)ethanone as a white solid: $^1$H NMR (400 MHz, DMSO-$d_6$) δ 6.95-6.92 (m, 1H), 4.81-4.72 (m, 2H), 4.32-4.17 (m, 2H), 4.00-3.96 (m, 2H), 2.14-2.10 (m, 3H).

Preparation of 1-(2-amino-6,7-dihydropyrazolo[1,5-a]pyrazin-5(4H)-yl)ethanone

A round bottom flask was charged with 1-(2-nitro-6,7-dihydropyrazolo[1,5-a]pyrazin-5(4H)-yl)ethanone (200 mg, 0.952 mmol), ethanol (20 mL) and 10% palladium on carbon (50% wet, 80 mg dry weight). The flask was sparged with nitrogen, charged with hydrogen gas to a pressure of 1 atm (balloon) and stirred for 3 h at room temperature. After this time, the hydrogen gas was evacuated and nitrogen charged into the flask. The catalyst was removed by filtration through a pad of diatomaceous earth and the filter cake washed with methanol (50 mL). The filtrate was concentrated under reduced pressure to afford 1-(2-amino-6,7-dihydropyrazolo[1,5-a]pyrazin-5(4H)-yl)ethanone as a yellow foam: $^1$H NMR (400 MHz, DMSO-$d_6$) δ 5.28-5.26 (m, 1H), 4.58-4.51 (m, 4H), 3.86-3.73 (m, 4H), 2.09-2.05 (m, 3H).

Preparation of 1-(2-(6-chloroimidazo[1,2-a]pyridin-8-ylamino)-6,7-dihydropyrazolo[1,5-a]pyrazin-5(4H)-yl)ethanone A mixture of 1-(2-amino-6,7-dihydropyrazolo[1,5-a]pyrazin-5(4H)-yl)ethanone (167 mg, 0.927 mmol), 8-bromo-6-chloroimidazo[1,2-a]pyridine hydrochloride salt (207 mg, 0.773 mmol) and cesium carbonate (630 mg, 1.93 mmol) in toluene (4 mL) was sparged with nitrogen while stirring for 10 min. Palladium(II) acetate (17 mg, 0.076 mmol) and 2,2'-bis(diphenylphosphino)-1,1'-binaphthalene (96 mg, 0.154 mmol) were then added and the reaction stirred at reflux for 18 h. After this time, the reaction was cooled to room temperature, diluted with a mixture of 1:1 methanol/methylene chloride (20 mL), filtered through diatomaceous earth and the filter cake washed with a mixture of 1:1 methanol/methylene chloride (80 mL). The filtrate was concentrated under reduced pressure and the resulting residue purified by chromatography (silica, gradient, methylene chloride to 19:1 methylene chloride/methanol) to afford 1-(2-(6-chloroimidazo[1,2-a]pyridin-8-ylamino)-6,7-dihydropyrazolo[1,5-a]pyrazin-5(4H)-yl)ethanone as a yellow foam: $^1$H NMR (400 MHz, DMSO-$d_6$) δ 9.17-9.12 (m, 1H), 8.19 (d, J=2.0 Hz, 1H), 7.87 (d, J=0.8 Hz, 1H), 7.77-7.75 (m, 1H), 7.52 (s, 1H), 6.07-6.03 (m, 1H), 4.74-4.64 (m, 2H), 4.15-4.01 (m, 2H), 3.93 (t, J=5.6 Hz, 2H), 2.14-2.09 (m, 3H); ESI MS m/z 331.1 [M+H]$^+$.

Preparation of 6-(8-(5-acetyl-4,5,6,7-tetrahydropyrazolo[1,5-a]pyrazin-2-ylamino)imidazo[1,2-a]pyridin-6-yl)indolin-2-one A mixture of 1-(2-(6-chloroimidazo[1,2-a]pyridin-8-ylamino)-6,7-dihydropyrazolo[1,5-a]pyrazin-5(4H)-yl)ethanone (89 mg, 0.27 mmol) and 6-(4,4,5,5-tetramethyl-1,3,2-dioxaborolan-2-yl)indolin-2-one (90 mg, 0.35 mmol) in 1 M aqueous sodium carbonate (0.54 mL) and 1,4-dioxane (2 mL) was sparged with nitrogen while stirring for 5 min. Tetrakis(triphenylphosphine)palladium(0) (62 mg, 0.054 mmol) was then added and the reaction heated under microwave irradiation at 150° C. for 1 h. After this time, the mixture was filtered through diatomaceous earth and the filter cake washed with a mixture of 3:7 methanol/methylene chloride (100 mL). The filtrate was washed with water (20 mL), then brine (20 mL) and dried over sodium sulfate. The drying agent was removed by filtration and the filtrate was concentrated under reduced pressure. The resulting residue was purified by chromatography (silica, gradient, methylene chloride to 19:1 methylene chloride/methanol) to afford 6-(8-(5-acetyl-4,5,6,7-tetrahydropyrazolo[1,5-a]pyrazin-2-ylamino)imidazo[1,2-a]pyridin-6-yl)indolin-2-one as an orange-brown solid: mp 161-165° C.; $^1$H NMR (400 MHz, DMSO-$d_6$, 107° C. δ 10.09 (bs, 1H), 8.15-8.14 (m, 2H), 7.86 (d, J=1.2 Hz, 1H), 7.78 (d, J=1.6 Hz, 1H), 7.47 (d, J=1.2 Hz, 1H), 7.27 (d, J=7.6 Hz, 1H), 7.17 (dd, J=7.6, 1.6 Hz, 1H), 7.05 (d, J=1.2 Hz, 1H), 6.04 (s, 1H), 4.68 (s, 2H), 4.06 (t, J=5.6 Hz, 2H), 3.93 (t, J=5.6 Hz, 2H), 3.47 (s, 2H), 2.10 (s, 3H); ESI MS m/z 428.2 [M+H]$^+$; HPLC, 4.06 min, >99% (AUC).

Example 3

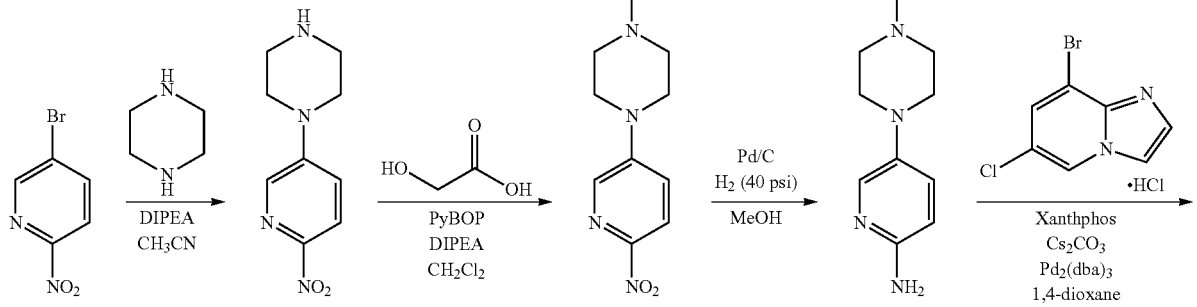

-continued

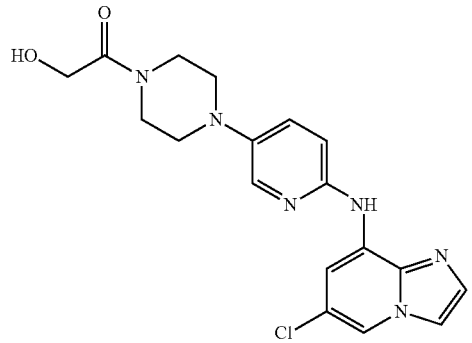

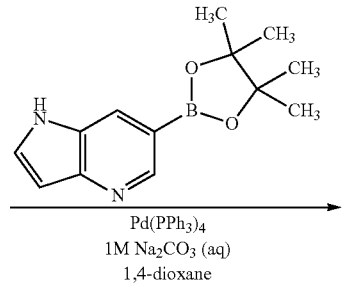

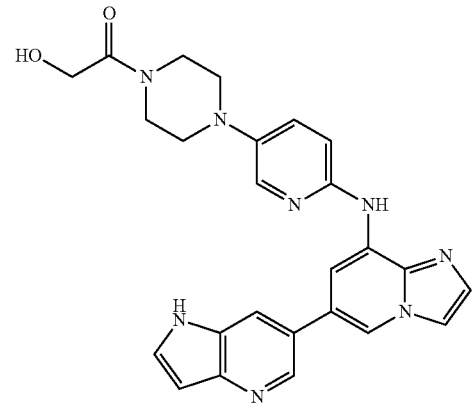

Preparation of 1-(6-nitropyridin-3-yl)piperazine

A mixture of 5-bromo-2-nitropyridine (3.00 g, 14.8 mmol) and piperazine (12.7 g, 147 mmol) in acetonitrile (10 mL) was stirred at reflux for 18 h. After this time, the reaction was cooled to room temperature and concentrated under reduced pressure. The residue was diluted in ethyl acetate (50 mL), washed with water (2×25 mL), then brine (25 mL) and dried over sodium sulfate. The drying agent was removed by filtration and the filtrate concentrated under reduced pressure. The resulting residue was purified by chromatography (silica, gradient, heptane to ethyl acetate) to afford 1-(6-nitropyridin-3-yl)piperazine as a yellow solid: $^1$H NMR (400 MHz, DMSO-$d_6$) δ 8.23 (d, J=2.8 Hz, 1H), 8.13 (d, J=9.2 Hz, 1H), 7.88 (dd, J=9.2, 2.8 Hz, 1H), 3.40 (t, J=4.8 Hz, 4H), 2.82 (t, J=4.8 Hz, 4H), NH (1H, not observed).

Preparation of 2-hydroxy-1-(4-(6-nitropyridin-3-yl)piperazin-1-yl)ethanone

A mixture of 1-(6-nitropyridin-3-yl)piperazine (1.00 g, 4.80 mmol), 2-hydroxyacetic acid (438 mg, 5.76 mmol), N,N-diisopropylethylamine (1.24 g, 9.56 mmol), and (benzotriazol-1-yloxy)-tripyrrolidinophosphonium hexafluorophosphate (2.18 g, 4.19 mmol) was stirred at room temperature for 18 h. After this time, the reaction was poured into ethyl acetate (50 mL) and washed with water (2×25 mL). The organic phase was dried over sodium sulfate, filtered and the filtrate concentrated under reduced pressure to afford 2-hydroxy-1-(4-(6-nitropyridin-3-yl)piperazin-1-yl)ethanone as a yellow solid which was used in the next step without purification: $^1$H NMR (400 MHz, DMSO-$d_6$) δ 8.26 (d, J=3.2 Hz, 1H), 8.18 (d, J=9.2 Hz, 1H), 7.48 (dd, J=9.2, 3.2 Hz, 1H), 4.67 (s, 1H), 4.14 (s, 2H), 3.63-3.56 (m, 8H); ESI MS m/z 267.1 [M+H]$^+$.

Preparation of 1-(4-(6-aminopyridin-3-yl)piperazin-1-yl)-2-hydroxyethanone

A 500-mL Parr hydrogenation bottle was purged with nitrogen and charged with impure 2-hydroxy-1-(4-(6-nitropyridin-3-yl)piperazin-1-yl)ethanone (1.56 g, 4.80 mmol assumed), methanol (50 mL) and 10% palladium on carbon (50% wet, 156 mg dry weight). The bottle was evacuated, charged with hydrogen gas to a pressure of 40 psi and shaken for 30 min at room temperature on a Parr hydrogenation apparatus. After this time, the hydrogen gas was evacuated and nitrogen charged into the bottle. The catalyst was removed by filtration through a pad of diatomaceous earth and the filter cake washed with methanol (100 mL). The filtrate was concentrated under reduced pressure to afford 1-(4-(6-aminopyridin-3-yl)piperazin-1-yl)-2-hydroxyethanone as a brown solid which was used in the next step without purification: $^1$H NMR (400 MHz, DMSO-$d_6$) δ 7.61 (d, J=2.8 Hz, 1H), 7.21 (dd, J=9.2, 2.8, Hz, 1H), 6.42 (d, J=9.2 Hz, 1H), 5.53 (s, 2H), 4.58 (t, J=4.8 Hz, 1H), 4.11 (d, J=4.8 Hz, 2H), 3.59-3.58 (m, 2H), 3.46-3.45 (m, 2H), 2.91-2.90 (m, 4H).

Preparation of 1-(4-(6-(6-chloroimidazo[1,2-a]pyridin-8-ylamino)pyridin-3-yl)piperazin-1-yl)-2-hydroxyethanone A mixture of 8-bromo-6-chloroimidazo[1,2-a]pyridine hydrochloride salt (997 mg, 3.72 mmol), impure 1-(4-(6-aminopyridin-3-yl)piperazin-1-yl)-2-hydroxyethanone (1.10 g, 4.66 mmol assumed), cesium carbonate (3.64 g, 11.2 mmol) and 4,5-bis(diphenylphosphino)-9,9-dimethylxanthene (431 mg, 0.745 mmol) in 1,4-dioxane (15 mL) was sparged with nitrogen while stirring for 5 min. Tris(dibenzylideneacetone)dipalladium(0) (340 mg, 0.371 mmol) was then added and the reaction stirred at 100° C. for 18 h. After this time, the reaction was cooled to room temperature, diluted with chloroform (100 mL) and filtered through diatomaceous earth. The filtrate was washed with water (100 mL), then brine (100 mL) and dried over sodium sulfate. The drying agent was removed by filtration and the filtrate concentrated under reduced pressure. The resulting residue was purified by chromatography (silica, gradient, methylene chloride to 1:9 methanol/methylene chloride), then chromatography (silica, gradient, methanol chloride to 1:10:20 methanol/ethyl acetate/methylene chloride) to afford 1-(4-(6-(6-(6-chloroimidazo[1,2-a]pyridin-8-ylamino)pyridin-3-yl)piperazin-1-yl)-2-hydroxyethanone as a solid: $^1$H NMR (400 MHz, DMSO-$d_6$) δ 9.17 (s, 1H), 8.32 (d, J=1.6 Hz, 1H), 8.30 (d, J=1.6 Hz, 1H), 8.02 (d, J=2.8 Hz, 1H), 7.90 (d, J=1.2 Hz, 1H), 7.55 (d, J=1.2 Hz, 1H), 7.46 (dd, J=9.2, 2.8 Hz, 1H), 7.38 (d, J=9.2 Hz, 1H), 4.62 (t, J=5.6 Hz, 1H), 4.14 (d, J=5.6 Hz, 2H), 3.63-3.62 (m, 2H), 3.52-3.51 (m, 2H), 3.11-3.10 (m, 4H).

Preparation of 1-(4-(6-(6-(1H-pyrrolo[3,2-b]pyridin-6-yl)imidazo[1,2-a]pyridin-8-ylamino)pyridin-3-yl)piperazin-1-yl)-2-hydroxyethanone A mixture of 1-(4-(6-(6-chloroimidazo[1,2-a]pyridin-8-ylamino)pyridin-3-yl)piperazin-1-yl)-2-hydroxyethanone (250 mg, 0.646 mmol), 6-(4,4,5,5-tetramethyl-1,3,2-dioxaborolan-2-yl)-1H-pyrrolo[3,2-b]pyridine (221 mg, 0.904 mmol) and 1 M aqueous sodium carbonate (1.9 mL) in 1,4-dioxane (3 mL) was sparged with nitrogen while stirring for 5 min. Tetrakis(triphenylphosphine)palladium(0) (75 mg, 0.065 mmol) was then added and the reaction heated under microwave irradiation at 150° C. for 45 min. After this time, the reaction was cooled to room temperature, diluted with a mixture of 1:9 methanol/methylene chloride (75 mL) and washed with water (75 mL), then brine (50 mL). The organic phase was dried over sodium sulfate, filtered and the filtrate concentrated under reduced pressure. The resulting residue was purified by chromatography (silica, gradient, methylene chloride to 1:9 methanol/methylene chloride), then trituration with acetonitrile (10 mL) to afford 1-(4-(6-(6-(1H-pyrrolo[3,2-b]pyridin-6-yl)imidazo[1,2-a]pyridin-8-ylamino)pyridin-3-yl)piperazin-1-yl)-2-hydroxyethanone as an off-white solid: mp 218-220° C.; $^1$H NMR (400 MHz, DMSO-$d_6$) δ 11.42 (s, 1H), 8.98 (s, 1H), 8.63-8.61 (m, 2H), 8.43 (d, J=1.2 Hz, 1H), 7.99-7.96 (m, 3H), 7.71 (t, J=2.8 Hz, 1H), 7.56 (s, 1H), 7.47 (dd, J=9.2, 2.8 Hz, 1H), 7.38 (d, J=9.2 Hz, 1H), 6.61 (s, 1H), 4.61 (t, J=5.6 Hz, 1H), 4.13 (d, J=5.6 Hz, 2H), 3.63-3.61 (m, 2H), 3.51-3.49 (m, 2H), 3.10-3.08 (m, 4H); ESI MS m/z 469.4 [M+H]$^+$; HPLC, 3.28 min, 95.9% (AUC).

Example 4

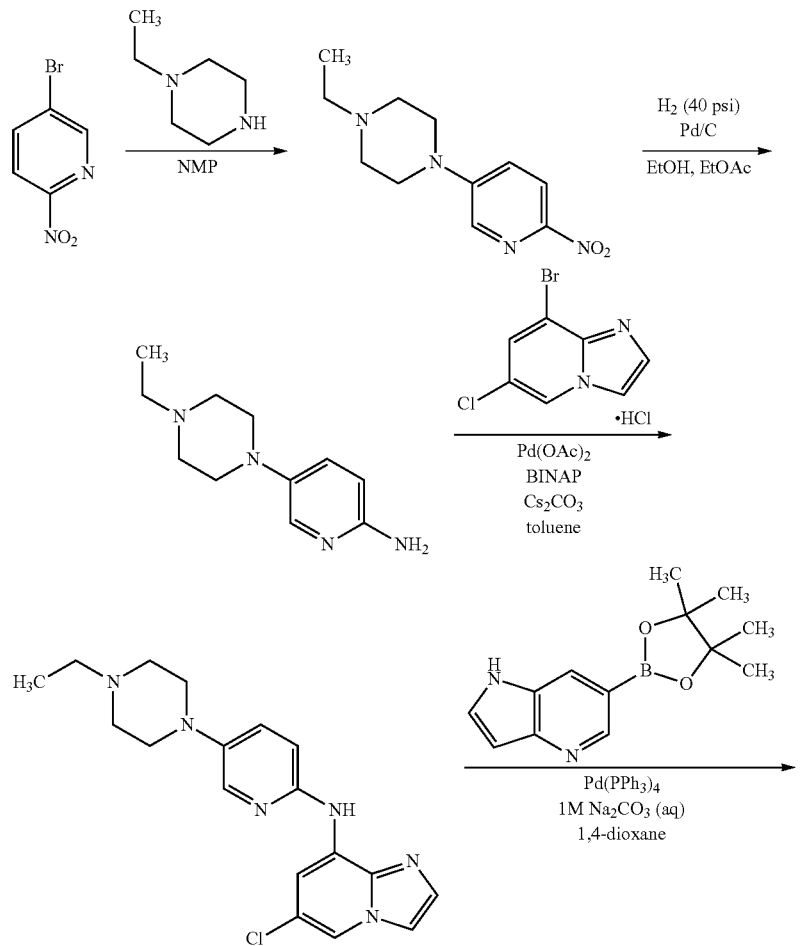

-continued

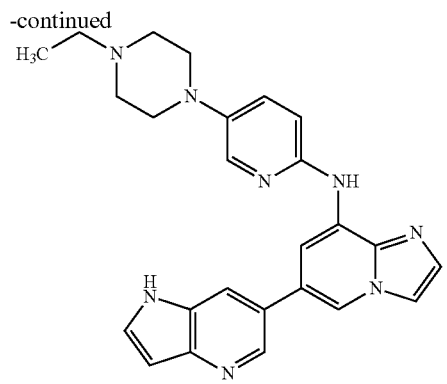

Preparation of 1-ethyl-4-(6-nitropyridin-3-yl)piperazine

A mixture of 5-bromo-2-nitropyridine (1.02 g, 5.02 mmol) and 1-ethylpiperazine (1.71 g, 15.0 mmol) in N-methyl-2-pyrrolidinone (5 mL) was stirred at 120° C. for 3 h. After this time, the reaction was cooled to room temperature, poured into water (100 mL) and extracted with methylene chloride (2×100 mL). The combined organic layers were dried over sodium sulfate, filtered and the filtrate concentrated under reduced pressure. The resulting residue was purified by chromatography (silica, gradient, 1:49 methanol/methylene chloride to 1:9 methanol/methylene chloride) to afford 1-ethyl-4-(6-nitropyridin-3-yl)piperazine as a yellow solid: $^1$H NMR (400 MHz, DMSO-$d_6$) δ 8.25 (d, J=2.8 Hz, 1H), 8.14 (d, J=9.2 Hz, 1H), 7.48 (dd, J=9.2, 2.8 Hz, 1H), 3.50-3.46 (m, 4H), 2.50-2.38 (m, 4H, merged with DMSO peak), 2.37 (q, J=7.2 Hz, 2H), 1.02 (t, J=7.2 Hz, 3H).

Preparation of 5-(4-ethylpiperazin-1-yl)pyridin-2-amine

A 500-mL Parr hydrogenation bottle was purged with nitrogen and charged with 1-ethyl-4-(6-nitropyridin-3-yl)piperazine (1.13 g, 4.78 mmol), ethanol (60 mL), ethyl acetate (120 mL) and 10% palladium on carbon (50% wet, 480 mg dry weight). The bottle was evacuated, charged with hydrogen gas to a pressure of 40 psi and shaken for 1 h at room temperature on a Parr hydrogenation apparatus. After this time, the hydrogen gas was evacuated and nitrogen charged into the bottle. The catalyst was removed by filtration through a pad of diatomaceous earth and the filter cake washed with ethanol (10 mL). The filtrate was concentrated under reduced pressure to afford 5-(4-ethylpiperazin-1-yl)pyridin-2-amine as a light yellow solid which was used in the next step without purification: $^1$H NMR (400 MHz, DMSO-$d_6$) δ $^1$H NMR (400 MHz, DMSO-$d_6$) □□δ 7.59 (d, J=2.8 Hz, 1H), 7.15 (dd, J=8.8, 2.8 Hz, 1H), 6.38 (d, J=8.8 Hz, 1H), 5.36 (bs, 2H), 2.93-2.91 (m, 4H), 2.50-2.49 (m, 4H, merged with DMSO peak), 2.37 (q, J=7.2 Hz, 2H), 1.04 (t, J=7.2 Hz, 3H).

Preparation of 6-chloro-N-(5-(4-ethylpiperazin-1-yl)pyridin-2-yl)imidazo[1,2-a]pyridin-8-amine A mixture of impure 5-(4-ethylpiperazin-1-yl)pyridin-2-amine (1.00 g, 4.85 mmol assumed), 8-bromo-6-chloroimidazo[1,2-a]pyridine hydrochloride salt (1.30 g, 4.85 mmol), 2,2'-bis(diphenylphosphino)-1,1'-binaphthalene (634 mg, 1.02 mmol) and cesium carbonate (4.90 g, 15.0 mmol) in toluene (50 mL) was sparged with nitrogen while stirring for 10 min. Palladium(II) acetate (120 mg, 0.491 mmol) was then added and the reaction stirred at reflux for 18 h. After this time, the reaction was cooled to room temperature, diluted in a mixture of 1:1 methanol/methylene chloride (100 mL) and filtered through diatomaceous earth. The filtrate was concentrated under reduced pressure and the resulting residue purified by chromatography (silica, gradient, 1:19 methanol/methylene chloride to 1:6 methanol/methylene chloride) to afford 6-chloro-N-(5-(4-ethylpiperazin-1-yl)pyridin-2-yl)imidazo[1,2-a]pyridin-8-amine as a yellow-green solid: $^1$H NMR (400 MHz, DMSO-$d_6$) δ 9.12 (s, 1H), 8.30 (d, J=2.0 Hz, 1H), 8.26 (d, J=2.0 Hz, 1H), 7.99 (d, J=2.8 Hz, 1H), 7.89 (d, J=0.8 Hz, 1H), 7.55 (d, J=0.8 Hz, 1H), 7.43 (dd, J=8.8, 2.8 Hz, 1H), 7.35 (d, J=8.8 Hz, 1H), 3.11-3.10 (m, 4H), 2.50-2.49 (m, 4H, merged with DMSO peak), 2.38-2.37 (m, 2H), 1.04 (t, J=7.2 Hz, 3H).

Preparation of N-(5-(4-ethylpiperazin-1-yl)pyridin-2-yl)-6-(1H-pyrrolo[3,2-b]pyridin-6-yl)imidazo[1,2-a]pyridin-8-amine A mixture of 6-chloro-N-(5-(4-ethylpiperazin-1-yl)pyridin-2-yl)imidazo[1,2-a]pyridin-8-amine (357 mg, 1.00 mmol), 6-(4,4,5,5-tetramethyl-1,3,2-dioxaborolan-2-yl)-1H-pyrrolo[3,2-b]pyridine (244 mg, 1.00 mmol) and 1 M aqueous sodium carbonate (1.8 mL) in 1,4-dioxane (4 mL) was sparged with nitrogen while stirring for 15 min.

Tetrakis(triphenylphosphine)palladium(0) (230 mg, 0.194 mmol) was then added and the reaction heated under microwave irradiation at 150° C. for 40 min. After this time, the mixture was cooled to room temperature and extracted with a mixture of 1:1 methanol/methylene chloride (20 mL). The organic phase was dry loaded onto silica and purified by chromatography (silica, gradient, 1:49 methanol/methylene chloride to 1:9 methanol/methylene chloride), then trituration with acetonitrile to afford N-(5-(4-ethylpiperazin-1-yl)pyridin-2-yl)-6-(1H-pyrrolo[3,2-b]pyridin-6-yl)imidazo[1,2-a]pyridin-8-amine as a light gray solid: mp 227-230° C.; $^1$H NMR (400 MHz, DMSO-$d_6$) δ 11.41 (s, 1H), 8.92 (s, 1H), 8.63 (d, J=2.0 Hz, 1H), 8.60 (s, 1H), 8.42 (s, 1H), 7.97-7.96 (m, 3H), 7.71-7.70 (m, 1H), 7.56 (s, 1H), 7.43 (dd, J=9.0, 2.4 Hz, 1H), 7.35 (d, J=8.8 Hz, 1H), 6.61 (s, 1H), 3.10-3.08 (m, 4H), 2.38-2.36 (m, 2H), 1.04 (t, J=6.8 Hz, 3H), CH$_2$ (4H, not observed); ESI MS m/z 439.6 [M+H]$^+$; HPLC, 3.06 min, >99% (AUC).

Example 5

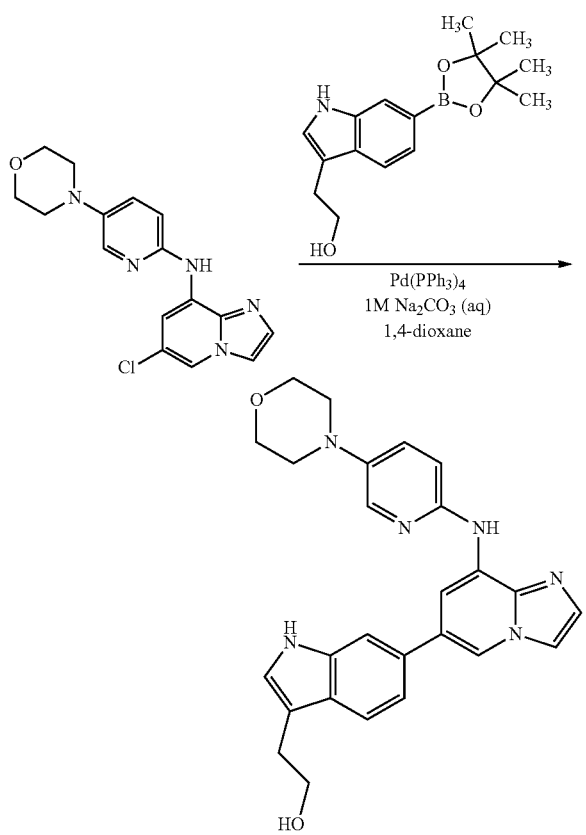

Preparation of 2-(6-(8-(5-morpholinopyridin-2-ylamino)imidazo[1,2-a]pyridin-6-yl)-1H-indol-3-yl)ethanol A mixture 6-chloro-N-(5-morpholinopyridin-2-yl)imidazo[1,2-a]pyridin-8-amine (231 mg, 0.700 mmol) and 2-(6-(4,4,5,5-tetramethyl-1,3,2-dioxaborolan-2-yl)-1H-indol-3-yl)ethanol (220 mg, 0.766 mmol) in 1 M aqueous sodium carbonate (0.8 mL) and 1,4-dioxane (3 mL) was sparged with nitrogen while stirring for 10 min.

Tetrakis(triphenylphosphine)palladium(0) (97 mg, 0.084 mmol) was then added and the reaction heated under microwave irradiation at 150° C. for 35 min. After this time, the reaction was cooled to room temperature and partitioned between a mixture of 5:1 methylene chloride/methanol (120 mL) and water (50 mL). The layers were separated and the aqueous phase extracted with a mixture of 4:1 methylene chloride/methanol (2×50 mL). The combined organic layers were dried over sodium sulfate, filtered and the filtrate concentrated under reduced pressure. The resulting residue was purified by chromatography (silica, 19:1 methylene chloride/methanol), then trituration with acetonitrile to afford 2-(6-(8-(5-morpholinopyridin-2-ylamino)imidazo[1,2-a]pyridin-6-yl)-1H-indol-3-yl)ethanol as a light brown solid: mp 159-161° C.; $^1$H NMR (400 MHz, DMSO-$d_6$) δ 10.93 (s, 1H), 8.91 (s, 1H), 8.62 (d, J=0.8 Hz, 1H), 8.36 (s, 1H), 7.97-7.95 (m, 2H), 7.62 (d, J=8.4 Hz, 1H), 7.58 (s, 1H), 7.44 (dd, J=8.8, 2.8 Hz, 1H), 7.33 (d, J=8.8 Hz, 1H), 7.29 (dd, J=8.4, 1.2 Hz, 1H), 7.21 (d, J=2.0 Hz, 1H), 4.62 (bs, 1H), 3.75 (t, J=4.8 Hz, 4H), 3.69-3.67 (m, 2H), 3.07 (t, J=4.8 Hz, 4H), 2.88 (t, J=7.2 Hz, 2H); ESI MS m/z 455.3 [M+H]$^+$; HPLC, 4.29 min, >99% (AUC).

Example 6

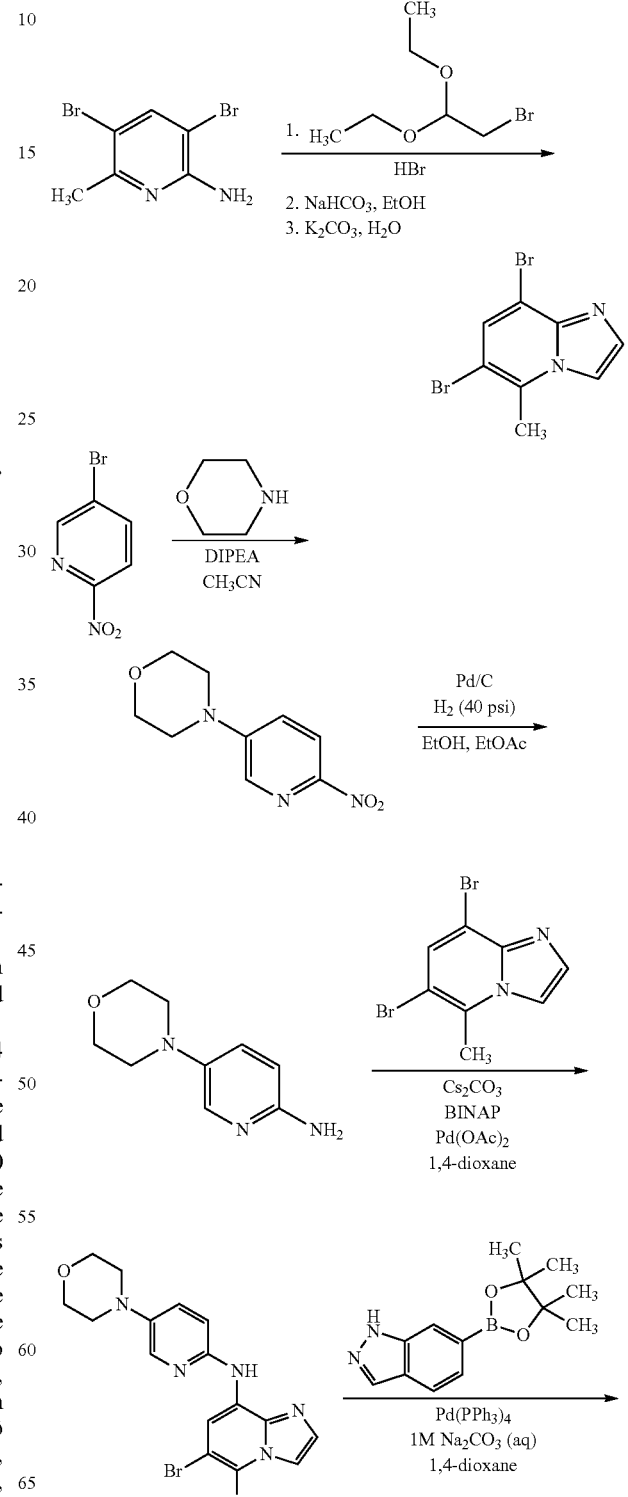

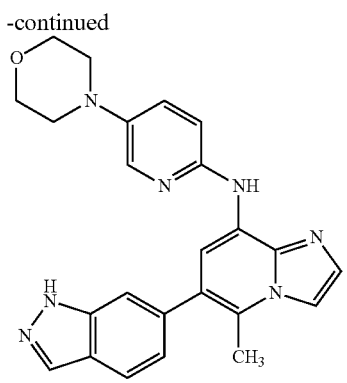

Preparation of 6,8-dibromo-5-methylimidazo[1,2-a]pyridine

A mixture of 2-bromo-1,1-diethoxyethane (1.78 g, 9.03 mmol) and 48% hydrobromic acid (2 mL) was stirred at reflux for 2 h. The reaction was then cooled to room temperature and treated with sodium bicarbonate until gas evolution ceased. The mixture was filtered and the filter cake washed with ethanol (10 mL). 3,5-Dibromo-6-methylpyridin-2-amine (1.50 g, 5.62 mmol) was then added to the filtrate and the mixture stirred at reflux for 5.5 h. The reaction was then cooled to room temperature and concentrated under reduced pressure. The residue was diluted with 0.19 M aqueous potassium carbonate (75 mL) and stirred at room temperature for 1 h. After this time, the resulting suspension was filtered and the filter cake purified by chromatography (silica, gradient, hexanes to ethyl acetate) to afford 6,8-dibromo-5-methylimidazo[1,2-a]pyridine as a light orange solid: $^1$H NMR (400 MHz, DMSO-$d_6$) δ 8.11 (d, J=1.2 Hz, 1H), 7.84 (s, 1H), 7.72 (d, J=1.2 Hz, 1H), 2.71 (s, 3H); ESI MS m/z 289.1 [M+H]$^+$.

Preparation of 4-(6-nitropyridin-3-yl)morpholine

A mixture of 5-bromo-2-nitropyridine (1.00 g, 4.93 mmol), morpholine (515 mg, 5.91 mmol) and N,N-diisopropylethylamine (1.91 g, 14.8 mmol) in acetonitrile (12 mL) was stirred at reflux for 16 h. After this time, the reaction was cooled to room temperature and concentrated under reduced pressure to afford 4-(6-nitropyridin-3-yl)morpholine as a yellow solid: $^1$H NMR (400 MHz, DMSO-$d_6$ δ 8.26 (d, J=3.2 Hz, 1H), 8.17 (d, J=9.2 Hz, 1H), 7.49 (dd, J=9.2, 3.2 Hz, 1H), 3.75 (t, J=4.8 Hz, 4H), 3.46 (t, J=4.8 Hz, 4H)

Preparation of 5-morpholinopyridin-2-amine

A 500-mL Parr hydrogenation bottle was purged with nitrogen and charged with 4-(6-nitropyridin-3-yl)morpholine (370 mg, 1.77 mmol), ethanol (80 mL), ethyl acetate (40 mL) and 10% palladium on carbon (50% wet, 180 mg dry weight). The bottle was evacuated, charged with hydrogen gas to a pressure of 40 psi and shaken for 30 min at room temperature on a Parr hydrogenation apparatus. After this time, the hydrogen gas was evacuated and nitrogen charged into the bottle. The catalyst was removed by filtration through a pad of diatomaceous earth and the filter cake washed with methanol (70 mL). The filtrate was concentrated under reduced pressure to afford 5-morpholinopyridin-2-amine as a tan solid which was used in the next step without purification: $^1$H NMR (400 MHz, DMSO-$d_6$) δ 7.60 (d, J=3.2 Hz, 1H), 7.16 (dd, J=8.8, 3.2 Hz, 1H), 6.40 (d, J=8.8 Hz, 1H), 5.38 (bs, 2H), 3.70 (t, J=4.8 Hz, 4H), 2.89 (t, J=4.8 Hz, 4H).

Preparation of 6-bromo-5-methyl-N-(5-morpholinopyridin-2-yl)imidazo[1,2-a]pyridin-8-amine A mixture of impure 5-morpholinopyridin-2-amine (259 mg, 1.45 mmol assumed), 6,8-dibromo-5-methylimidazo[1,2-a]pyridine (313 mg, 1.08 mmol), 2,2'-bis(diphenylphosphino)-1,1'-binaphthalene (134 mg, 0.215 mmol) and cesium carbonate (879 mg, 2.70 mmol) in toluene (5 mL) was sparged with nitrogen while stirring for 10 min. Palladium(II) acetate (24 mg, 0.098 mmol) was then added and the reaction stirred at reflux for 18 h. After this time, the reaction was cooled to room temperature, diluted with a mixture of 1:1 methanol/methylene chloride (100 mL) and filtered through diatomaceous earth. The filtrate was concentrated under reduced pressure and the resulting residue purified by chromatography (silica, gradient, methylene chloride to 1:9 methanol/methylene chloride) to afford 6-bromo-5-methyl-N-(5-morpholinopyridin-2-yl)imidazo[1,2-a]pyridin-8-amine as an off-white solid: $^1$H NMR (400 MHz, DMSO-$d_6$) δ 8.99 (s, 1H), 8.50 (s, 1H), 7.99 (d, J=3.2 Hz, 1H), 7.91 (d, J=0.8 Hz, 1H), 7.60 (d, J=0.8 Hz, 1H), 7.42 (dd, J=8.8, 3.2 Hz, 1H), 7.34 (d, J=8.8 Hz, 1H), 3.75 (t, J=4.8 Hz, 4H), 3.07 (t, J=4.8 Hz, 4H), 2.65 (s, 3H).

Preparation of 6-(1H-indazol-6-yl)-5-methyl-N-(5-morpholinopyridin-2-yl)imidazo[1,2-a]pyridin-8-amine A mixture of 6-bromo-5-methyl-N-(5-morpholinopyridin-2-yl)imidazo[1,2-a]pyridin-8-amine (250 mg, 0.644 mmol), 6-(4,4,5,5-tetramethyl-1,3,2-dioxaborolan-2-yl)-1H-indazole (188 mg, 0.770 mmol) and 1M aqueous sodium carbonate (0.9 mL) in 1,4-dioxane (4 mL) was sparged with nitrogen while stirring for 5 min. Tetrakis(triphenylphosphine)palladium(0) (111 mg, 0.0960 mmol) was then added and the reaction heated under microwave irradiation at 135° C. for 20 min. After this time, the reaction was cooled to room temperature, diluted with a mixture of 1:4 methanol/chloroform (75 mL) and filtered through diatomaceous earth. The filtrate was concentrated under reduced pressure and the resulting residue purified by chromatography (silica, gradient, methylene chloride to 1:9 methanol/methylene chloride), then trituration with acetonitrile to afford 6-(1H-indazol-6-yl)-5-methyl-N-(5-morpholinopyridin-2-yl)imidazo[1,2-a]pyridin-8-amine as a light yellow solid: mp 160-164° C.; $^1$H NMR (400 MHz, DMSO-$d_6$) δ 13.13 (s, 1H), 8.83 (s, 1H), 8.32 (s, 1H), 8.14 (s, 1H), 7.90 (d, J=0.8 Hz, 1H), 7.87-7.84 (m, 2H), 7.65 (d, J=0.8 Hz, 1H), 7.53 (s, 1H), 7.39 (dd, J=9.2, 3.2 Hz, 1H), 7.32 (d, J=9.2 Hz, 1H), 7.17 (dd, J=9.2, 1.2 Hz, 1H), 3.71 (t, J=4.8 Hz, 4H), 3.00 (t, J=4.8 Hz, 4H), 2.47 (s, 3H); ESI MS m/z 426.2 [M+H]$^+$; HPLC, 4.12 min, >99% (AUC).

Example 7

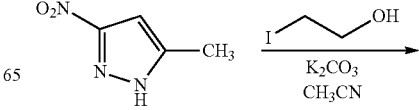

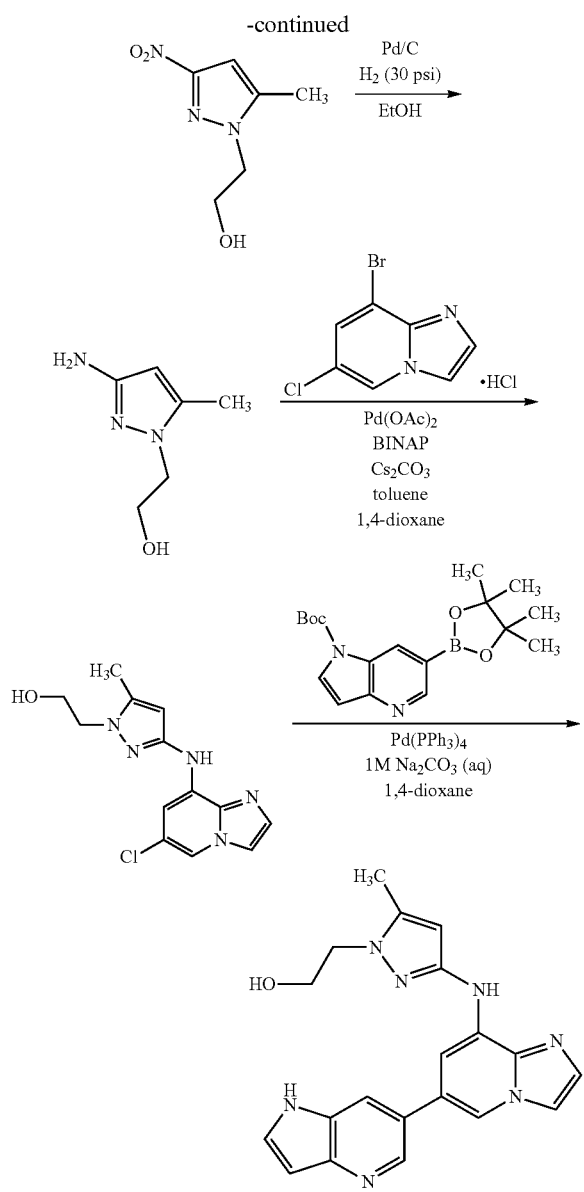

Preparation of
2-(5-methyl-3-nitro-1H-pyrazol-1-yl)ethanol

A solution of 5-methyl-3-nitro-1H-pyrazole (500 mg, 3.93 mmol) and potassium carbonate (1.08 g, 7.81 mmol) in acetonitrile (20 mL) was treated dropwise with 2-iodoethanol (2.00 g, 11.6 mmol) and the reaction stirred at reflux for 18 h. After this time, the reaction was cooled to room temperature, diluted with ethyl acetate (100 mL) and filtered through diatomaceous earth. The filtrate was concentrated under reduced pressure and the resulting residue purified by chromatography (silica, gradient, heptane to 1:1 ethyl acetate/heptane) to afford 2-(5-methyl-3-nitro-1H-pyrazol-1-yl)ethanol as a white solid: $^1$H NMR (400 MHz, DMSO-$d_6$) δ 6.82 (s, 1H), 4.97 (t, J=5.2 Hz, 1H), 4.19 (t, J=5.2 Hz, 2H), 3.75 (q, J=5.2 Hz, 2H), 2.35 (s, 3H).

Preparation of
2-(3-amino-5-methyl-1H-pyrazol-1-yl)ethanol

A 500-mL Parr hydrogenation bottle was purged with nitrogen and charged with 2-(5-methyl-3-nitro-1H-pyrazol-1-yl)ethanol (426 mg, 2.49 mmol), ethanol (100 mL) and 10% palladium on carbon (50% wet, 85 mg dry weight). The bottle was evacuated, charged with hydrogen gas to a pressure of 30 psi and shaken for 20 min at room temperature on a Parr hydrogenation apparatus. After this time, the hydrogen was evacuated and nitrogen charged into the bottle. The catalyst was removed by filtration through diatomaceous earth and the filter cake washed with methanol (75 mL). The filtrate was concentrated under reduced pressure to afford 2-(3-amino-5-methyl-1H-pyrazol-1-yl)ethanol as an off-white solid: $^1$H NMR (400 MHz, DMSO-$d_6$) δ 5.18 (s, 1H), 4.74 (t, J=5.2 Hz, 1H), 4.36 (bs, 2H), 3.76 (t, J=5.6 Hz, 2H), 3.61-3.58 (m, 2H), 2.10 (s, 3H).

Preparation of 2-(3-(6-chloroimidazo[1,2-a]pyridin-8-ylamino)-5-methyl-1H-pyrazol-1-yl)ethanol A mixture of 2-(3-amino-5-methyl-1H-pyrazol-1-yl)ethanol (345 mg, 2.44 mmol), 8-bromo-6-chloroimidazo[1,2-a]pyridine hydrochloride salt (514 mg, 1.92 mmol), 2,2'-bis(diphenylphosphino)-1,1'-binaphthalene (274 mg, 0.440 mmol) and cesium carbonate (1.43 g, 4.39 mmol) in toluene (3 mL) and 1,4-dioxane (3 mL) was sparged with nitrogen while stirring for 10 min. Palladium(II) acetate (54 mg, 0.22 mmol) was then added and the reaction stirred at 100° C. for 2 h. After this time, the reaction was cooled to room temperature, diluted with a mixture of 1:4 methanol/methylene chloride (150 mL) and filtered through diatomaceous earth. The filtrate was concentrated under reduced pressure and the resulting residue purified by chromatography (silica, gradient, methylene chloride to 1:19 methanol/methylene chloride) to afford 2-(3-(6-chloroimidazo[1,2-a]pyridin-8-ylamino)-5-methyl-1H-pyrazol-1-yl)ethanol as a green-brown foam: $^1$H NMR (400 MHz, CDCl$_3$) δ 7.68 (d, J=1.6 Hz, 1H), 7.51-7.47 (m, 3H), 7.42 (d, J=1.6 Hz, 1H), 5.79 (s, 1H), 4.12-4.09 (m, 2H), 4.06-4.04 (m, 2H), 2.29 (s, 3H), OH (1H, not observed); ESI MS m/z 292.1 [M+H]$^+$.

Preparation of 2-(3-(6-(1H-pyrrolo[3,2-b]pyridin-6-yl)imidazo[1,2-a]pyridin-8-ylamino)-5-methyl-1H-pyrazol-1-yl)ethanol A mixture of 2-(3-(6-chloroimidazo[1,2-a]pyridin-8-ylamino)-5-methyl-1H-pyrazol-1-yl)ethanol (210 mg, 0.720 mmol), tert-butyl 6-(4,4,5,5-tetramethyl-1,3,2-dioxaborolan-2-yl)-1H-pyrrolo[3,2-b]pyridine-1-carboxylate (297 mg, 0.863 mmol) and 1 M aqueous sodium carbonate (0.6 mL) in 1,4-dioxane (2 mL) was sparged with nitrogen while stirring for 5 min.

Tetrakis(triphenylphosphine)palladium(0) (125 mg, 0.108 mmol) was then added and the reaction heated under microwave irradiation at 145° C. for 30 min. After this time, the reaction was cooled to room temperature, dissolved in a mixture of 1:4 methanol/methylene chloride (75 mL) and filtered through diatomaceous earth. The filtrate was concentrated under reduced pressure and the resulting residue purified by chromatography (silica, gradient, methylene chloride to 1:9 methanol/methylene chloride), then semi-preparative HPLC (C18, 1:19 acetonitrile with 0.05% TFA/water with 0.05% TFA to 19:1 acetonitrile with 0.05% TFA/water with 0.05% TFA over 25 min). The combined column fractions were washed with saturated aqueous sodium bicarbonate (200 mL) and dried over sodium sulfate. The drying agent was removed by filtration and the filtrate concentrated under reduced pressure. The resulting residue was further purified by chromatography (silica, gradient, methylene chloride to 1:9 methanol/methylene chloride) to afford 2-(3-(6-(1H-pyrrolo[3,2-b]pyridin-6-yl)imidazo[1,2-a]pyridin-8-ylamino)-5-methyl-1H-pyrazol-1-yl)ethanol as a light brown solid: mp 127-130° C.; ¹H NMR (400 MHz, DMSO-d$_6$) δ 11.44 (bs, 1H), 8.63-8.62 (m, 2H), 8.34 (d, J=1.6 Hz, 1H), 8.08 (d, J=1.2 Hz, 1H), 7.95-7.94 (m, 1H), 7.92 (d, J=0.8 Hz, 1H), 7.70 (t, J=2.8 Hz, 1H), 7.52 (d, J=1.2 Hz, 1H), 6.60-6.59 (m, 1H), 5.95 (s, 1H), 4.83 (t, J=5.6 Hz, 1H), 4.01-3.98 (m, 2H), 3.77-3.74 (m, 2H), 2.25 (s, 3H); ESI MS m/z 374.2 [M+H]⁺; HPLC, 3.36 min, >99% (AUC).

Example 8

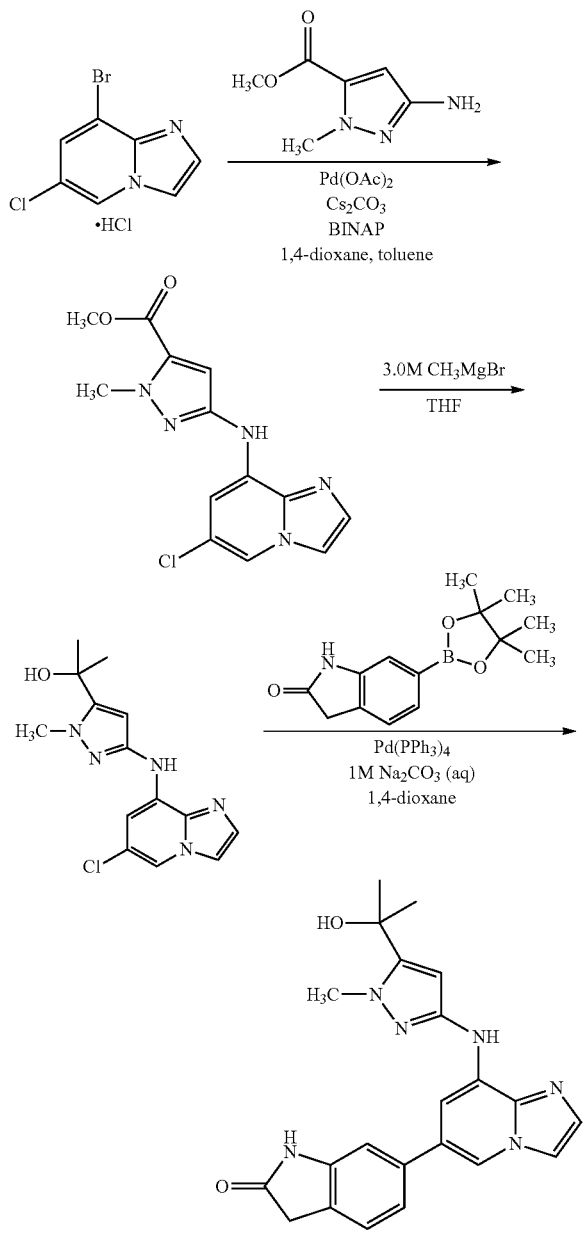

Preparation of methyl 3-(6-chloroimidazo[1,2-a]pyridin-8-ylamino)-1-methyl-1H-pyrazole-5-carboxylate A mixture of methyl 3-amino-1-methyl-1H-pyrazole-5-carboxylate (155 mg, 0.999 mmol), 8-bromo-6-chloroimidazo[1,2-a]pyridine hydrochloride salt (268 mg, 1.00 mmol), 2,2'-bis(diphenylphosphino)-1,1'-binaphthalene (135 mg, 0.216 mmol) and cesium carbonate (997 mg, 3.05 mmol) in toluene (5 mL) and 1,4-dioxane (5 mL) was sparged with nitrogen while stirring for 10 min. Palladium (II) acetate (25 mg, 0.11 mmol) was then added and the reaction stirred at reflux for 18 h. After this time, the reaction was cooled to room temperature, diluted with a mixture of 1:1 ethyl acetate/water (100 mL) and filtered through diatomaceous earth. The filtrate was concentrated under reduced pressure and the resulting residue purified by chromatography (silica, gradient, heptane to 3:7 heptane/ethyl acetate) to afford methyl 3-(6-chloroimidazo[1,2-a]pyridin-8-ylamino)-1-methyl-1H-pyrazole-5-carboxylate as a brown solid: ¹H NMR (400 MHz, DMSO-d$_6$) δ 9.37 (s, 1H), 8.24 (d, J=1.6 Hz, 1H), 7.89 (d, J=1.2 Hz, 1H), 7.73 (d, J=1.6 Hz, 1H), 7.55 (d, J=1.2 Hz, 1H), 6.72 (s, 1H), 4.06 (s, 3H), 3.84 (s, 3H); ESI MS m/z 306.2 [M+H]⁺.

Preparation of 2-(3-(6-chloroimidazo[1,2-a]pyridin-8-ylamino)-1-methyl-1H-pyrazol-5-yl)propan-2-ol A solution of methyl 3-(6-chloroimidazo[1,2-a]pyridin-8-ylamino)-1-methyl-1H-pyrazole-5-carboxylate (765 mg, 2.50 mmol) in tetrahydrofuran (15 mL) was cooled to −78° C. in an dry ice/acetone bath, under a nitrogen atmosphere, and treated with 3.0 M methyl magnesium bromide (5.0 mL). When the addition was complete, the cooling bath was removed and the reaction stirred at room temperature for 2 h. After this time, the reaction was cooled to 0° C., treated with water (2.0 mL) and extracted with ethyl acetate (250 mL). The organic phase was dried over sodium sulfate, filtered and the filtrate concentrated under reduced pressure to afford 2-(3-(6-chloroimidazo[1,2-a]pyridin-8-ylamino)-1-methyl-1H-pyrazol-5-yl)propan-2-ol as a solid: ¹H NMR (400 MHz, DMSO-d$_6$) δ 8.91 (s, 1H), 8.17 (d, J=2.0 Hz, 1H), 7.86 (d, J=0.8 Hz, 1H), 7.74 (d, J=2.0 Hz, 1H), 7.52 (s, 1H), 5.99 (s, 1H), 5.29 (s, 1H), 3.90 (s, 3H), 1.49 (s, 6H); ESI MS m/z 306.0 [M+H]⁺.

Preparation of 6-(8-(5-(2-hydroxypropan-2-yl)-1-methyl-1H-pyrazol-3-ylamino)imidazo[1,2-a]pyridin-6-yl)indolin-2-one A mixture of 2-(3-(6-chloroimidazo[1,2-a]pyridin-8-ylamino)-1-methyl-1H-pyrazol-5-yl)propan-2-ol (250 mg, 0.818 mmol), 6-(4,4,5,5-tetramethyl-1,3,2-dioxaborolan-2-yl)indolin-2-one (275 mg, 1.06 mmol) and 1M aqueous sodium carbonate (2.5 mL) in 1,4-dioxane (3 mL) was sparged with nitrogen while stirring for 5 min. Tetrakis(triphenylphosphine)palladium(0) (94 mg, 0.081 mmol) was then added and the reaction heated under microwave irradiation at 150° C. for 60 min. After this time, the reaction was cooled to room temperature, diluted with a mixture of 1:9 methanol/methylene chloride (150 mL) and filtered through diatomaceous earth. The filtrate was concentrated under reduced pressure and the resulting residue purified by chromatography (silica, gradient, methylene chloride to 1:4 methanol/methylene chloride), then trituration with acetonitrile, followed by trituration with methanol to afford 6-(8-(5-(2-hydroxypropan-2-yl)-1-methyl-1H-pyrazol-3-ylamino)imidazo[1,2-a]pyridin-6-yl)indolin-2-one as a light yellow solid: mp 180-182° C.; ¹H NMR (400 MHz, DMSO-d$_6$) δ 10.54 (s, 1H), 8.61 (s, 1H), 8.25 (d, J=1.6 Hz, 1H), 8.04 (d, J=1.2 Hz, 1H), 7.91 (d, J=1.2 Hz, 1H), 7.51 (d, J=0.8 Hz, 1H), 7.31 (d, J=7.6 Hz, 1H), 7.21 (dd, J=7.6, 1.6 Hz, 1H), 7.06 (d, J=0.8 Hz, 1H), 5.99 (s, 1H), 5.27 (s, 1H), 3.92 (s, 3H), 3.53 (s, 2H), 1.50 (s, 6H); ESI MS m/z 403.1 [M+H]⁺; HPLC, 4.30 min, >99% (AUC).

Example 9

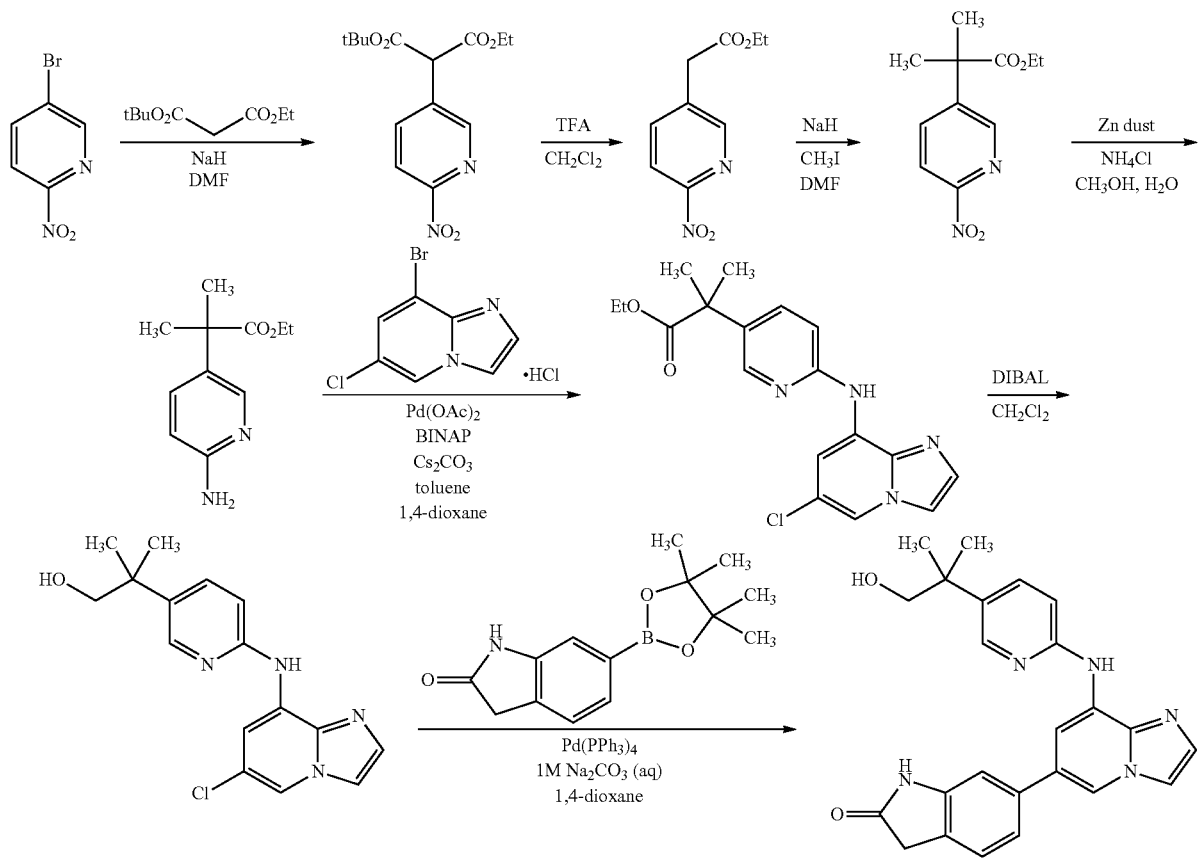

Preparation of 1-tert-butyl 3-ethyl 2-(6-nitropyridin-3-yl)malonate

A solution of tert-butyl ethyl malonate (1.11 g, 5.90 mmol) in N,N-dimethylformamide (10 mL) was treated with 60% sodium hydride dispersed in mineral oil (565 mg, 14.1 mmol), under a nitrogen atmosphere, and stirred at room temperature for 30 min. A solution of 5-bromo-2-nitropyridine (1.00 g, 4.93 mmol) in N,N-dimethylformamide (10 mL) was added dropwise, over 10 min, and the reaction stirred at room temperature for a further 32 h. After this time, the reaction was partitioned between water (100 mL) and ethyl acetate (100 mL). The layers were separated and the aqueous phase was extracted with ethyl acetate (100 mL). The combined organic layers were washed with water (200 mL), then brine (200 mL) and dried over sodium sulfate. The drying agent was removed by filtration and the filtrate concentrated under reduced pressure. The resulting residue was purified by chromatography (silica, gradient, heptane to 1:1 methylene chloride/heptane) to afford 1-tert-butyl 3-ethyl 2-(6-nitropyridin-3-yl)malonate as a yellow oil: $^1$H NMR (400 MHz, DMSO-$d_6$) δ 8.66 (d, J=2.0 Hz, 1H), 8.37 (d, J=8.4 Hz, 1H), 7.26 (dd, J=8.4, 2.0 Hz, 1H), 5.27 (s, 1H), 4.20 (q, J=7.2 Hz, 2H), 1.42 (s, 9H), 1.22 (t, J=7.2 Hz, 3H).

Preparation of ethyl 2-(6-nitropyridin-3-yl)acetate

A solution of 1-tert-butyl 3-ethyl 2-(6-nitropyridin-3-yl)malonate (2.40 g, 7.73 mmol) in trifluoroacetic acid (20 mL) and methylene chloride (20 mL) was stirred at reflux for 2 h. After this time, the reaction was cooled to room temperature and concentrated under reduced pressure. The resulting residue was diluted with methylene chloride (100 mL), washed with saturated aqueous sodium bicarbonate (100 mL) and dried over sodium sulfate. The drying agent was removed by filtration and the filtrate concentrated under reduced pressure to afford ethyl 2-(6-nitropyridin-3-yl)acetate as an orange oil: $^1$H NMR (400 MHz, DMSO-$d_6$) δ 8.59 (d, J=2.0 Hz, 1H), 8.31 (d, J=8.4 Hz, 1H), 8.17 (dd, J=8.4, 2.0 Hz, 1H), 4.13 (q, J=7.2 Hz, 2H), 3.98 (s, 2H), 1.21 (t, J=7.2 Hz, 3H).

Preparation ethyl 2-methyl-2-(6-nitropyridin-3-yl)propanoate

A solution of ethyl 2-(6-nitropyridin-3-yl)acetate (926 mg, 4.41 mmol) in N,N-dimethylformamide (12 mL) was cooled to 0° C., under a nitrogen atmosphere, and treated with 60% sodium hydride dispersed in mineral oil (186 mg, 4.65 mmol) and stirred at 0° C. for 5 min. Iodomethane (683 mg, 4.81 mmol) was then added and the reaction gradually warmed to room temperature. Once the purple color had dissipated, the reaction was cooled to 0° C. and treated with 60% sodium hydride dispersed in mineral oil (186 mg, 4.65 mmol) and N,N-dimethylformamide (2 mL), then stirred at 0° C. for 5 min. A second addition of iodomethane (683 mg, 4.81 mmol) was made and the reaction gradually warmed to room temperature over 2 h, then stirred at room temperature for 16 h. After this time, the reaction was partitioned between water (100 mL) and ethyl acetate (100 mL). The layers were separated and the organic phase was washed with water (100 mL), then brine (2×100 mL) and dried over sodium sulfate. The drying agent was removed by filtration and the filtrate concentrated under reduced pressure to afford ethyl 2-methyl-2-(6-nitropyridin-3-yl)propanoate as a yellow oil: $^1$H NMR (400 MHz, DMSO-$d_6$) δ 8.67 (d, J=2.4 Hz, 1H), 8.29 (d, J=8.4 Hz, 1H), 8.20 (dd, J=8.4, 2.4 Hz, 1H), 4.12 (q, J=7.2 Hz, 2H), 1.61 (s, 6H), 1.14 (t, J=7.2 Hz, 3H).

Preparation of ethyl 2-(6-aminopyridin-3-yl)-2-methylpropanoate

A mixture of ethyl 2-methyl-2-(6-nitropyridin-3-yl)propanoate (1.03 g, 4.32 mmol), ammonium chloride (5.75 g, 107 mmol) and zinc dust (2.81 g, 43.0 mmol) in a mixture of 2:1 methanol/water (30 mL) was stirred at room temperature for 3 h. After this time, the reaction was diluted with ethyl acetate (100 mL) and filtered through diatomaceous earth. The filtrate was washed with water (100 mL) and the aqueous layer extracted with ethyl acetate (2×50 mL). The combined organic layers were dried over sodium sulfate, filtered and the filtrate concentrated under reduced pressure to afford ethyl 2-(6-aminopyridin-3-yl)-2-methylpropanoate as an orange oil: $^1$H NMR (400 MHz, DMSO-$d_6$) δ 7.85 (d, J=2.4 Hz, 1H), 7.32 (dd, J=8.4, 2.4 Hz, 1H), 6.41 (d, J=8.4 Hz, 1H), 5.83 (bs, 2H), 4.04 (q, J=7.2 Hz, 2H), 1.44 (s, 6H), 1.11 (t, J=7.2 Hz, 3H).

Preparation of ethyl 2-(6-(6-chloroimidazo[1,2-a]pyridin-8-ylamino)pyridin-3-yl)-2-methylpropanoate A mixture of ethyl 2-(6-aminopyridin-3-yl)-2-methylpropanoate (775 mg, 3.72 mmol), 8-bromo-6-chloroimidazo[1,2-a]pyridine hydrochloride salt (831 mg, 3.10 mmol), 2,2'-bis(diphenylphosphino)-1,1'-binaphthalene (386 mg, 0.620 mmol) and cesium carbonate (2.02 g, 6.20 mmol) in toluene (5 mL) and 1,4-dioxane (5 mL) was sparged with nitrogen while stirring for 10 min. Palladium(II) acetate (76 mg, 0.34 mmol) was then added and the reaction stirred at 100° C. for 2.5 h. After this time, the reaction was cooled to room temperature, diluted with a mixture of 1:4 methanol/methylene chloride (150 mL) and filtered through diatomaceous earth. The filtrate was concentrated under reduced pressure and the resulting residue purified by chromatography (silica, gradient, heptane to 2:3 ethyl acetate/heptane) to afford impure ethyl 2-(6-(6-chloroimidazo[1,2-a]pyridin-8-ylamino)pyridin-3-yl)-2-methylpropanoate as a brown solid which was used without further purification in the next step: $^1$H NMR (400 MHz, DMSO-$d_6$) contained an impurity (25%) which made assignment of the aromatic peaks ambiguous; ESI MS m/z 359.1 [M+H]$^+$.

Preparation of 2-(6-(6-chloroimidazo[1,2-a]pyridin-8-ylamino)pyridin-3-yl)-2-methylpropan-1-ol A solution of impure ethyl 2-(6-(6-chloroimidazo[1,2-a]pyridin-8-ylamino)pyridin-3-yl)-2-methylpropanoate (575 mg, 1.60 mmol assumed) in anhydrous methylene chloride (15 mL) was cooled to 0° C., under a nitrogen atmosphere, and treated dropwise with 1M diisobutylaluminum hydride in methylene chloride (8.0 mL, 8.0 mmol) over 15 min. When the addition was complete, the reaction was gradually warm to room temperature over 2 h and stirred at room temperature for 1 h. The mixture was carefully treated with water (20 mL) (Caution: add slowly), then potassium sodium tartrate tetrahydrate (400 mg, 1.42 mmol) was added and the reaction stirred at room temperature for a further 30 min. After this time, the reaction was diluted with ethyl acetate (100 mL) and the layers were separated. The organic phase was dried over sodium sulfate, filtered and the filtrate concentrated under reduced pressure. The resulting residue was purified by chromatography (silica, gradient, heptane to 4:1 ethyl acetate/heptane) to afford 2-(6-(6-chloroimidazo[1,2-a]pyridin-8-ylamino)pyridin-3-yl)-2-methylpropan-1-ol as an off-white solid: $^1$H NMR (400 MHz, DMSO-$d_6$) δ 9.25 (s, 1H), 8.42 (d, J=2.0 Hz, 1H), 8.32-8.30 (m, 2H), 7.91 (d, J=1.2 Hz, 1H), 7.68 (dd, J=8.8, 2.8 Hz, 1H), 7.57 (d, J=1.2 Hz, 1H), 7.37 (d, J=8.8 Hz, 1H), 4.70 (t, J=5.2 Hz, 1H), 3.41 (d, J=5.2 Hz, 2H), 1.24 (s, 6H); ESI MS m/z 317.8 [M+H]$^+$.

Preparation of 6-(8-(5-(1-hydroxy-2-methylpropan-2-yl)pyridin-2-ylamino)imidazo[1,2-a]pyridin-6-yl)indolin-2-one A mixture of 2-(6-(6-chloroimidazo[1,2-a]pyridin-8-ylamino)pyridin-3-yl)-2-methylpropan-1-ol (195 mg, 0.616 mmol), 6-(4,4,5,5-tetramethyl-1,3,2-dioxaborolan-2-yl)indolin-2-one (176 mg, 0.679 mmol) and 1 M aqueous sodium carbonate (0.5 mL) in 1,4-dioxane (2 mL) was sparged with nitrogen while stirring for 5 min.

Tetrakis(triphenylphosphine)palladium(0) (107 mg, 0.0925 mmol) was then added and the reaction heated under microwave irradiation at 145° C. for 30 min. After this time, the reaction was cooled to room temperature, diluted with a mixture of 1:4 methanol/methylene chloride (100 mL) and filtered through diatomaceous earth. The filtrate was concentrated under reduced pressure and the resulting residue purified by chromatography (silica, gradient, methylene chloride to 1:19 methanol/methylene chloride), then trituration with methanol to afford 6-(8-(5-(1-hydroxy-2-methylpropan-2-yl)pyridin-2-ylamino)imidazo[1,2-a]pyridin-6-yl)indolin-2-one as a light pink-orange solid: mp 260-266° C. dec; $^1$H NMR (400 MHz, DMSO-$d_6$) δ 10.50 (s, 1H), 9.02 (s, 1H), 8.65 (d, J=1.2 Hz, 1H), 8.37 (d, J=1.2 Hz, 1H), 8.26 (d, J=2.4 Hz, 1H), 7.96 (d, J=0.8 Hz, 1H), 7.67 (dd, J=8.8, 2.8 Hz, 1H), 7.55 (d, J=0.8 Hz, 1H), 7.36-7.32 (m, 2H), 7.23 (dd, J=7.6, 1.6 Hz, 1H), 7.07 (d, J=0.8 Hz, 1H), 4.70 (t, J=7.2 Hz, 1H), 3.54 (s, 2H), 3.41 (d, J=7.2 Hz, 2H), 1.24 (s, 6H); ESI MS m/z 414.4 [M+H]$^+$; HPLC, 4.07 min, >99% (AUC).

Example 10

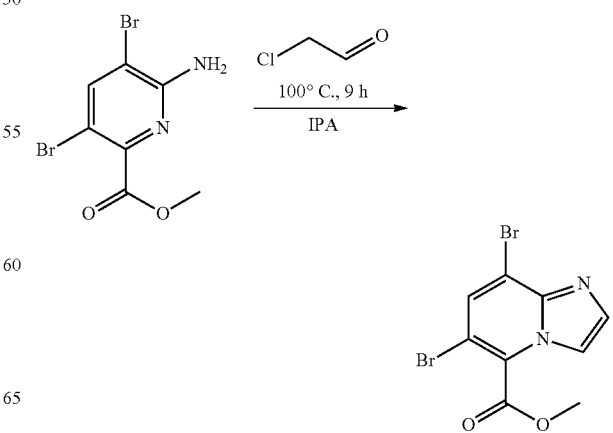

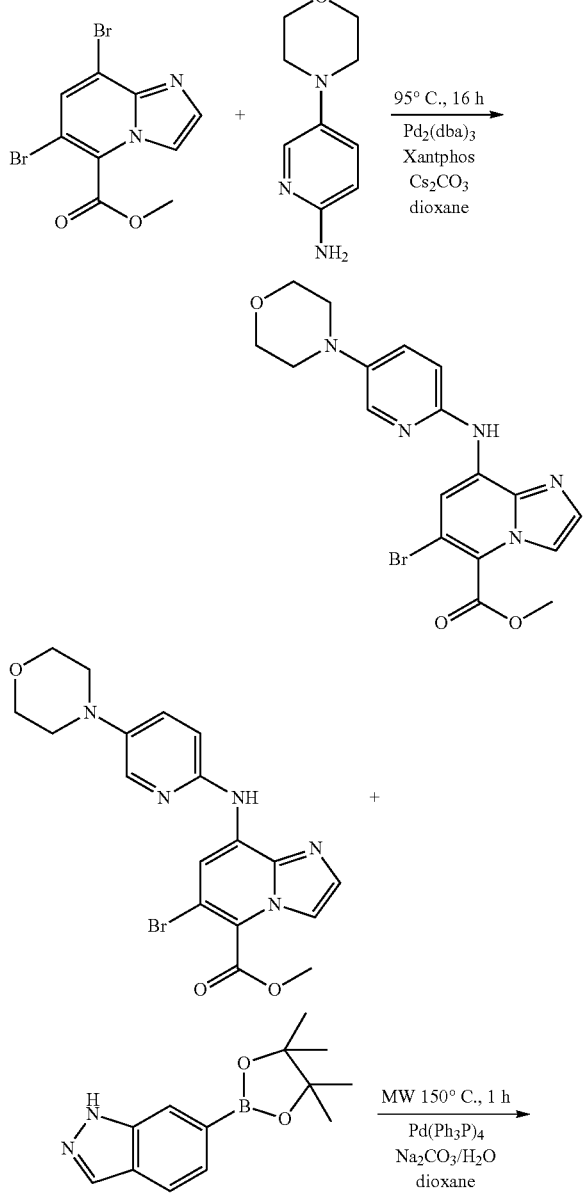

Methyl 6,8-dibromoimidazo[1,2-a]pyridine-5-carboxylate

A 200 mL round bottom flask was charged with methyl 6-amino-3,5-dibromopicolinate 1 (8.6 g, 0.0277 mol), 2-chloroacetaldehyde (19.93 mL, 0.139 mol, 45% w/w in water) and isopropanol (100 mL). The mixture was stirred at 100° C. for 9 h. After this time, the reaction mixture was concentrated under reduced pressure, and the residue was partitioned between water and ethyl acetate. The organic layer was dried over sodium sulfate and the resulting residue was purified by column chromatography. The solvent was removed by Rota vapor to afford methyl 6,8-dibromoimidazo[1,2-a]pyridine-5-carboxylate as an off-white solid.

Methyl 6-bromo-8-(5-morpholinopyridin-2-ylamino)imidazo[1,2-a]pyridine-5-carboxylate A 200 mL round bottom flask was charged with Methyl 6,8-dibromoimidazo[1,2-a]pyridine-5-carboxylate (1.86 g, 0.0055 mol), 5-morpholinopyridin-2-amine (1.0 g, 0.0055 mol), $Pd_2(dba)_3$ (0.25 g, 0.00027 mol), Xantphos (0.318, 0.00055 mol), $Cs_2CO_3$ (3.58 g, 0.011 mol), and dioxane 100 mL. The mixture was stirred at 95° C. for 16 h. After this time, the reaction mixture was filtered through celite and the filtrate was partitioned between water and ethyl acetate. The organic layer was dried over sodium sulfate and the resulting residue was purified by column chromatography. The solvent was removed by Rota vapor to afford methyl 6-bromo-8-(5-morpholinopyridin-2-ylamino)imidazo[1,2-a]pyridine-5-carboxylate as a solid.

Methyl 6-(1H-indazol-6-yl)-8-(5-morpholinopyridin-2-ylamino)imidazo[1,2-a]pyridine-5-carboxylate A 2-5 mL micro tube was charged with Methyl 6-bromo-8-(5-morpholinopyridin-2-ylamino)imidazo[1,2-a]pyridine-5-carboxylate (0.3 g, 0.00069 mol), 6-(4,4,5,5-tetramethyl-1,3,2-dioxaborolan-2-yl)-1H-indazole (0.2 g, 0.00083 mol), $Pd_2(dba)_3$ (0.04 g, 0.000035 mol), $Na_2CO_3/H_2O$ (1.6 mL, 0.0016 mol), and 4.5 mL of dioxane. The mixture was stirred at 150° C. for 1 h in biotage microwave. After this time, the reaction mixture was partitioned between between water and ethyl acetate. The organic layer was dried over sodium sulfate. The resulting residue was purified by column chromatography. The solvent was removed by Rota vapor to afford methyl 6-(1H-indazol-6-yl)-8-(5-morpholinopyridin-2-ylamino)imidazo[1,2-a]pyridine-5-carboxylate as an off-white solid. MS scan (ESI+)m/z:470.3 (M+H).

Example 11

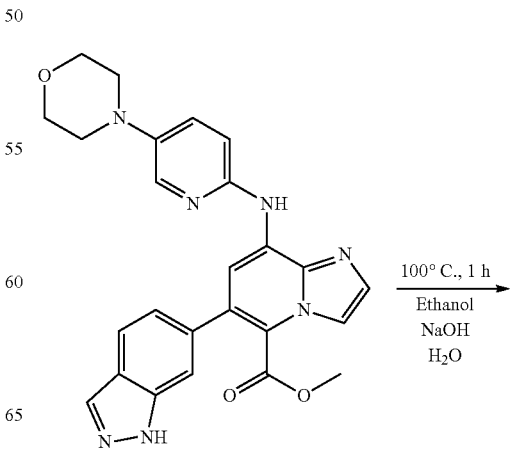

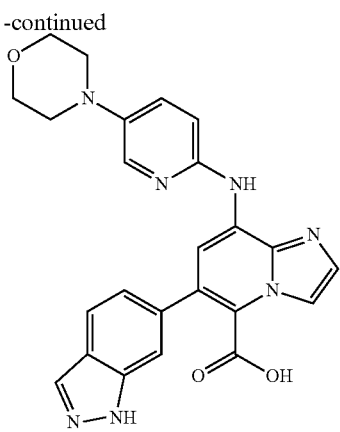

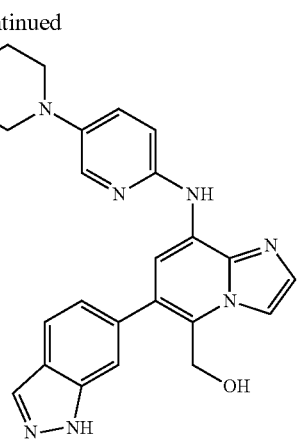

6-(1H-indazol-6-yl)-8-(5-morpholinopyridin-2-ylamino)imidazo[1,2-a]pyridine-5-carboxylic Acid A 100 mL round bottom flask was charged with Methyl 6-(1H-indazol-6-yl)-8-(5-morpholinopyridin-2-ylamino) imidazo[1,2-a]pyridine-5-carboxylate (0.15 g, 0.00032 mol), ethanol (20 mL) and 1M NaOH (3.2 mL, 0.0032 mol). The mixture was stirred at 100° C. for 1 h. After this time, the reaction mixture was concentrated under reduced pressure, and to the residue was acidified to pH 3 with 1N HCl, extracted with dichloromethane. The organic layer was dried over sodium sulfate. The resulting residue was purified by column chromatography. The solvent was removed by Rota vapor to afford 6-(1H-indazol-6-yl)-8-(5-morpholinopyridin-2-ylamino)imidazo[1,2-a]pyridine-5-carboxylic acid as a solid. MS scan (ESI+)m/z:456.2 (M+H).

Example 12

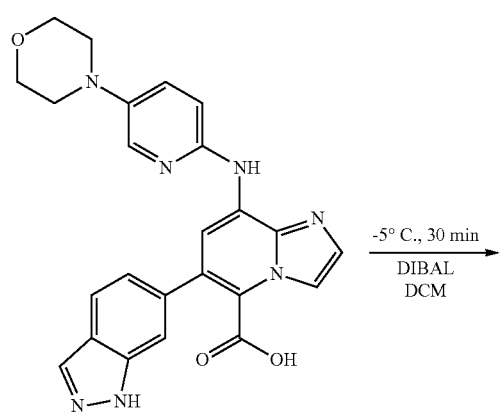

(6-(1H-indazol-6-yl)-8-(5-morpholinopyridin-2-ylamino)imidazo[1,2-a]pyridin-5-yl)methanol 9

A 100 mL round bottom flask was charged with 6-(1H-indazol-6-yl)-8-(5-morpholinopyridin-2-ylamino)imidazo [1,2-a]pyridine-5-carboxylic acid (0.15 g, 0.00032 mol) and dichloromethane (30 mL). The solution was cooled to −5° C., DIBAL (1.3 mL, 0.00128 mol, 1M in dochloromethane) was added dropwise via a syringe. The mixture was stirred at −5° C. for 30 min. After this time, the reaction mixture was quenched with methanol (1 mL) and added sat. aqueous Na/K tartrate (15 mL), stirred at RT for 30 min, extracted with ethyl acetate. The organic layer was dried over sodium sulfate. The resulting residue was purified by column chromatography. The solvent was removed by Rota vapor to afford (6-(1H-indazol-6-yl)-8-(5-morpholinopyridin-2-ylamino)imidazo[1,2-a]pyridin-5-yl)methanol as an off-white solid. MS scan (ESI+)m/z:442.3 (M+H).

Example 13

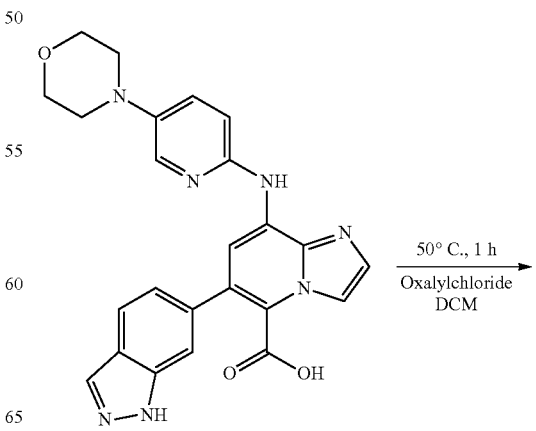

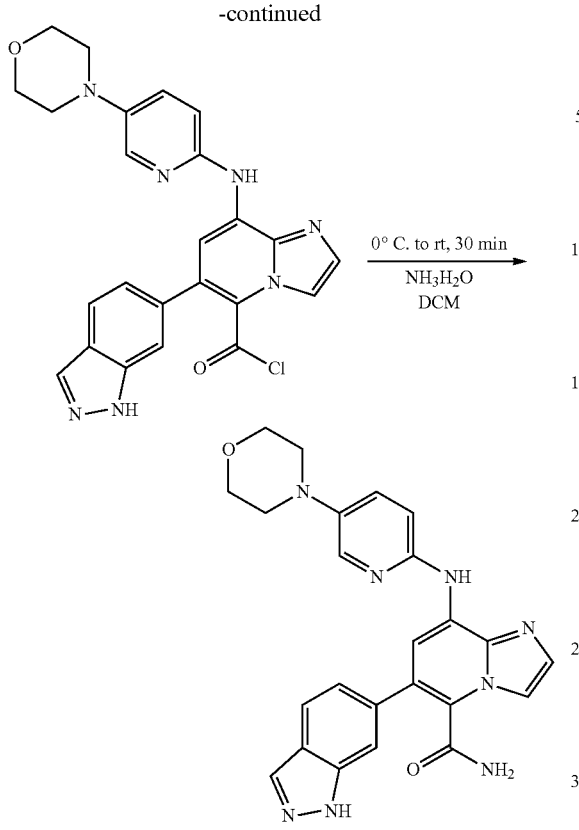

6-(1H-indazol-6-yl)-8-(5-morpholinopyridin-2-ylamino)imidazo[1,2-a]pyridine-5-carboxamide A 200 mL round bottom flask was charged with 6-(1H-indazol-6-yl)-8-(5-morpholinopyridin-2-ylamino)imidazo[1,2-a]pyridine-5-carboxylic acid (0.18 g, 0.0004 mol), dichloromethane (80 mL), Oxalylchloride (2.4 mL, 0.0048 mol, 2M in dichloromethane), and 1 drop of DMF. The mixture was stirred at 50° C. for 1 h. After this time, the solvent was removed by Rota vapor to afford 6-(1H-indazol-6-yl)-8-(5-morpholinopyridin-2-ylamino)imidazo[1,2-a]pyridine-5-carbonyl chloride as a solid, which was dissolved in dichloromethane (50 mL), $NH_3H_2O$ (20 mL) was added at 0° C. The mixture was stirred at RT for 30 min. After this time, the organic layer was separated and dried over sodium sulfate. The solvent was removed by Rota vapor to afford 6-(1H-indazol-6-yl)-8-(5-morpholinopyridin-2-ylamino)imidazo[1,2-a]pyridine-5-carboxamide as a solid. MS scan (ESI+)m/z:455.2 (M+H).

Example 14

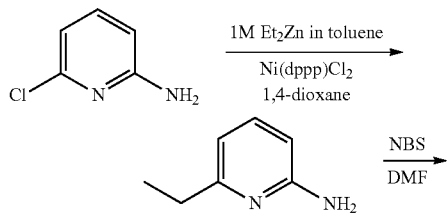

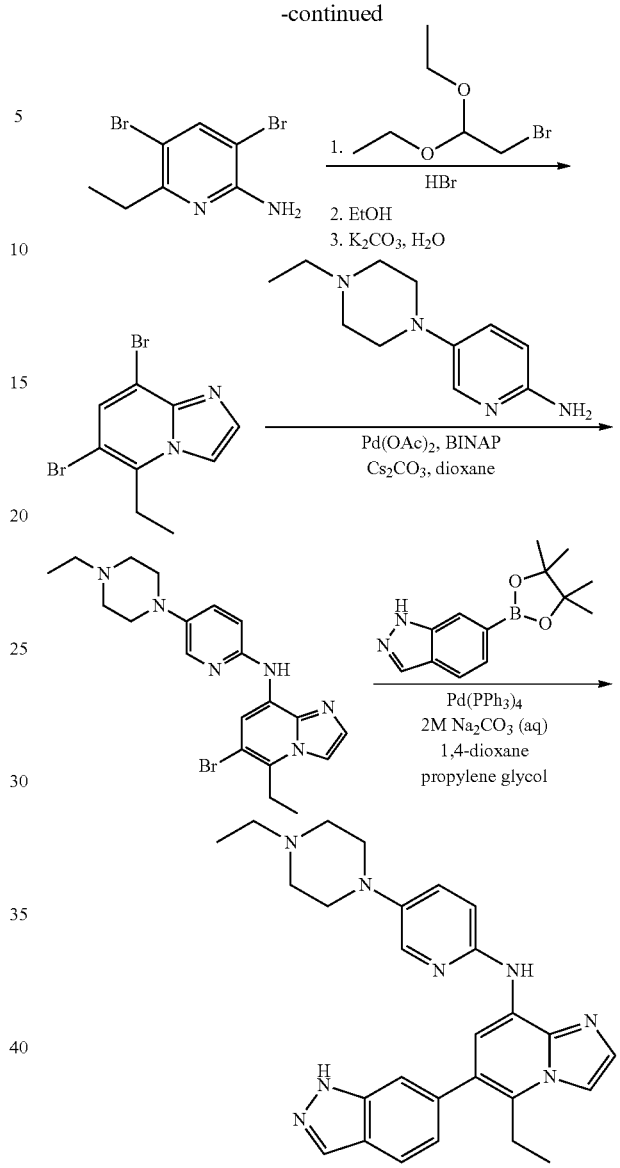

Preparation of 6-ethylpyridin-2-amine

A mixture of 6-chloro-2-aminopyridine (15.0 g, 116 mmol) and [1,3-bis(diphenylphosphino)propane]nickel(II) chloride (5.70 g, 10.5 mmol) in anhydrous 1,4-dioxane (450 mL) was treated with 1.1 M solution of diethylzinc in toluene (225 mL) and the reaction stirred, under a nitrogen atmosphere, at reflux for 16 h. After this time, the reaction was cooled to room temperature, treated with methanol (200 mL) and concentrated under reduced pressure. The resulting residue was diluted in brine (500 L) and extracted with a mixture of 9:1 methylene chloride/methanol (3×300 mL). The combined organic layers were dried over sodium sulfate, filtered and the filtrate concentrated under reduced pressure to afford 6-ethylpyridin-2-amine as a brown gel, which was used in the next step without further purification: $^1$H NMR (400 MHz, $CDCl_3$) δ 7.36 (t, J=7.6 Hz, 1H), 6.53 (d, J=7.6 Hz, 1H), 6.33 (d, J=7.6 Hz, 1H), 4.41 (bs, 2H), 2.64 (q, J=7.6 Hz, 2H), 1.26 (t, J=7.6 Hz, 3H).

Preparation of 3,5-dibromo-6-ethylpyridin-2-amine

To a mixture of 6-ethylpyridin-2-amine (2.00 g, 16.3 mmol) in N,N-dimethylformamide (20 mL) at 10° C. was added N-bromosuccinimide (5.80 g, 32.6 mmol) portion wise over a period of 15 min and the reaction was stirred at room temperature for 2 h. After this time, the reaction was poured into ice-cold water (100 mL) and extracted with ethyl acetate (2×50 mL). The combined organic layers were washed with water (2×25 mL) and dried over anhydrous sodium sulfate. The drying agent was removed by filtration and the filtrate was concentrated under reduced pressure. The resulting residue was purified by chromatography (silica, gradient, hexane to ethyl acetate) to afford 3,5-dibromo-6-ethylpyridin-2-amine as a yellow crystalline solid: $^1$H NMR (400 MHz, CDCl$_3$) δ 7.37 (s, 1H), 4.85 (bs, 2H), 2.76 (q, J=7.6 Hz, 2H), 1.22 (t, J=7.6 Hz, 3H).

Preparation of 6,8-dibromo-5-ethylimidazo[1,2-a]pyridine

A mixture of 2-bromo-1,1-diethoxyethane (9.58 mL, 63.7 mmol) and 48% aqueous hydrobromic acid (4.0 mL) was stirred at reflux for 2 h. After this time, the reaction was cooled to room temperature and treated with sodium bicarbonate (3.50 g, 41.6 mmol) until gas evolution ceased. The mixture was filtered and the filtrate diluted with ethanol (180 mL). 3,5-Dibromo-6-ethylpyridin-2-amine (17.9 g, 63.9 mmol) was then added and the mixture stirred at reflux for 16 h. After this time, the reaction was cooled to room temperature and concentrated under reduced pressure to a volume of approximately 10 mL. The resulting suspension was filtered and the filter cake washed with cold ethanol (40 mL). The filter cake was taken into water (250 mL) and the mixture was adjusted to pH~8 with potassium carbonate. The suspension was filtered and the filter cake dried to a constant weight under vacuum to afford 6,8-dibromo-5-ethylimidazo[1,2-a]pyridine as a light brown solid: $^1$H NMR (400 MHz, CDCl$_3$) δ 7.73 (s, 1H), 7.67 (s, 1H), 7.61 (s, 1H), 3.15 (q, J=7.6 Hz, 2H), 1.30 (t, J=7.6 Hz, 3H).

Preparation of 6-bromo-5-ethyl-N-(5-(4-ethylpiperazin-1-yl)pyridin-2-yl)imidazo[1,2-a]pyridin-8-amine A mixture of 5-(4-ethylpiperazin-1-yl)pyridin-2-amine (3.30 g, 16.0 mmol), 6,8-dibromo-5-ethylimidazo[1,2-a]pyridine (5.00 g, 16.4 mmol), 2,2'-bis(diphenylphosphino)-1,1'-binaphthalene (2.14 g, 3.44 mmol) and cesium carbonate (16.4 g, 50.5 mmol) in 1,4-dioxane (200 mL) was sparged with nitrogen while stirring for 10 min. Palladium (II) acetate (368 mg, 1.51 mmol) was then added and the reaction stirred at reflux for 18 h. After this time, the reaction was cooled to room temperature, diluted with a mixture of 1:1 methanol/methylene chloride (200 mL) and filtered through a pad of diatomaceous earth. The filtrate was concentrated under reduced pressure and the resulting residue purified by chromatography (silica, gradient, 1:24 methanol/methylene chloride to 2:23 methanol/methylene chloride) to afford 6-bromo-5-ethyl-N-(5-(4-ethylpiperazin-1-yl)pyridin-2-yl)imidazo[1,2-a]pyridin-8-amine as a brown solid: $^1$H NMR (400 MHz, CDCl$_3$) δ 8.40 (s, 1H), 8.03 (d, J=2.8 Hz, 1H), 7.76 (s, 1H), 7.54 (s, 2H), 7.28-7.25 (m, 1H), 6.84 (d, J=9.2 Hz, 1H), 3.18-3.13 (m, 4H), 3.10 (q, J=7.6 Hz, 2H), 2.64-2.60 (m, 4H), 2.49 (q, J=7.2 Hz, 2H), 1.28 (t, J=7.6 Hz, 3H), 1.13 (t, J=7.2 Hz, 3H).

Preparation of 5-ethyl-N-(5-(4-ethylpiperazin-1-yl)pyridin-2-yl)-6-(1H-indazol-6-yl)imidazo[1,2-a]pyridin-8-amine A mixture of 6-bromo-5-ethyl-N-(5-(4-ethylpiperazin-1-yl)pyridin-2-yl)imidazo[1,2-a]pyridin-8-amine (600 mg, 1.40 mmol) and 6-(4,4,5,5-tetramethyl-1,3,2-dioxaborolan-2-yl)-1H-indazole (580 mg, 2.38 mmol) in 2 M aqueous sodium carbonate (1.8 mL), propylene glycol (0.2 mL) and 1,4-dioxane (12 mL) was sparged with argon while stirring for 30 min.

Tetrakis(triphenylphosphine)palladium(0) (242 mg, 0.210 mmol) was then added and the reaction heated under microwave irradiation at 145° C. for 20 min. After this time, the reaction was cooled to room temperature and diluted with methanol (15 mL). The organic phase was dry loaded onto silica gel and purified by column chromatography (silica, gradient, methylene chloride to 19:1 methylene chloride/methanol), then trituration with hexanes to afford 5-ethyl-N-(5-(4-ethylpiperazin-1-yl)pyridin-2-yl)-6-(1H-indazol-6-yl)imidazo[1,2-a]pyridin-8-amine as a brown solid: mp 216.6° C.; $^1$H NMR (400 MHz, DMSO-d$_6$) δ 13.12 (s, 1H), 8.81 (s, 1H), 8.23 (s, 1H), 8.13 (s, 1H), 7.98 (s, 1H), 7.85-7.80 (m, 2H), 7.62 (s, 1H), 7.49 (s, 1H), 7.37 (dd, J=8.8, 2.4 Hz, 1H), 7.28 (d, J=9.2 Hz, 1H), 7.12 (d, J=7.6 Hz, 1H), 3.02-3.01 (m, 4H), 2.82 (q, J=7.2 Hz, 2H), 1.18 (t, J=7.2 Hz, 3H), 1.01 (t, J=6.8 Hz, 3H); CH$_2$ (m, 6H, not observed); MM MS m/z 467.2 [M+H]$^+$; HPLC, 11.1 min, 98.4% (AUC).

Example 15

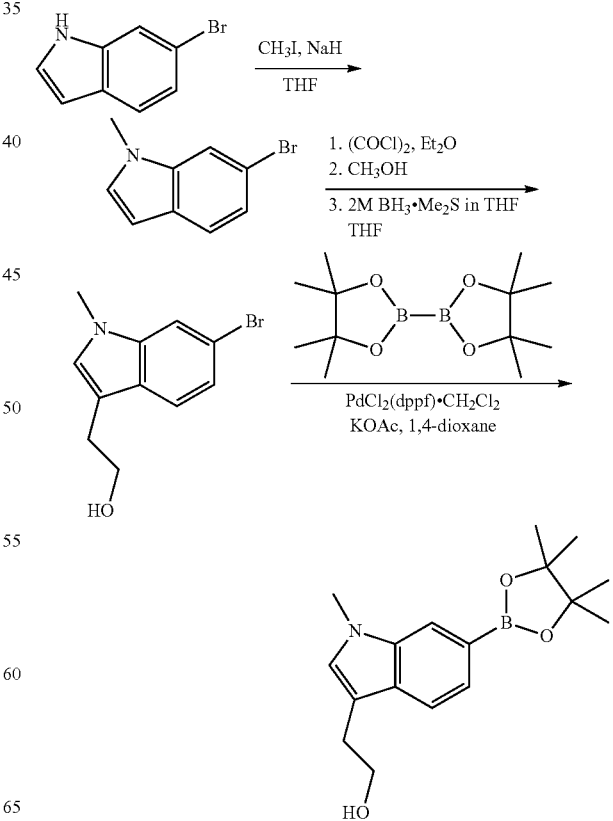

Preparation of 6-bromo-1-methyl-1H-indole

To a stirred suspension of 60% sodium hydride (4.88 g, 122 mmol) in tetrahydrofuran (150 mL) was added 6-bromoindole (15.0 g, 76.5 mmol) portionwise, followed by methyl iodide (11.9 g, 83.8 mmol) dropwise and the mixture stirred at room temperature for 16 h. After this time, the reaction was poured into ice-cold water and extracted with ethyl acetate (2×100 mL). The combined organic layers were washed sequentially with water, then brine and dried over sodium sulfate. The drying agent was removed by filtration and the filtrate concentrated under reduced pressure to afford 6-bromo-1-methyl-1H-indole as a pale red solid: $^1$H NMR (400 MHz, CDCl$_3$) δ 7.49 (m, 2H), 7.22 (dd, J=8.0, 1.6 Hz, 1H), 7.04 (d, J=3.2 Hz, 1H), 6.47 (d, J=3.2 Hz, 1H), 3.77 (s, 3H).

Preparation of 2-(6-bromo-1-methyl-1H-indol-3-yl)ethanol

To a solution of 6-bromo-1-methyl-1H-indole (18.0 g, 85.6 mmol) in diethyl ether (180 mL) at 0° C., was added oxalyl chloride (13.1 g, 103 mmol) dropwise under a nitrogen atmosphere. The resulting mixture was allowed to warm to room temperature and stirred for 1 h. After this time, methanol (15 mL) was added and the reaction stirred at room temperature further for 24 h. After this time, the reaction was filtered and the filter cake washed with water (20 mL), then cold diethyl ether (20 mL). The filter cake was dissolved in methylene chloride (100 mL) and dried over sodium sulfate. The drying agent was removed by filtration and the filtrate concentrated under reduced pressure to afford methyl 2-(6-bromo-1-methyl-1H-indol-3-yl)-2-oxoacetate which was used in the next step without purification.

A suspension of methyl 2-(6-bromo-1-methyl-1H-indol-3-yl)-2-oxoacetate (18.0 g, 60.8 mmol) in tetrahydrofuran (200 mL) was treated with 2 M borane dimethylsulfide complex in tetrahydrofuran (121 mL) and stirred at reflux for 5 h. After this time, the reaction was cooled to room temperature, diluted with water (50 mL) and saturated aqueous sodium bicarbonate (100 mL) and extracted with diethyl ether (3×250 mL). The combined organic layers were washed sequentially with water and brine, dried over sodium sulfate, filtered and the filtrate concentrated under reduced pressure to afford 2-(6-bromo-1-methyl-1H-indol-3-yl)ethanol as a white solid: $^1$H NMR (400 MHz, CDCl$_3$) δ 7.46 (d, J=8.4 Hz, 1H), 7.46 (d, J=1.6 Hz, 2H), 7.22 (dd, J=8.4, 1.6 Hz, 1H), 6.92 (s, 1H), 3.88 (t, J=6.4 Hz, 2H), 3.73 (s, 3H), 2.99 (t, J=6.4 Hz, 3H).

Preparation of 2-(1-methyl-6-(4,4,5,5-tetramethyl-1,3,2-dioxaborolan-2-yl)-1H-indol-3-yl)ethanol A mixture of 2-(6-bromo-1-methyl-1H-indol-3-yl)ethanol (13.0 g, 51.2 mmol), bis(pinacolato)diboron (16.8 g, 66.1 mmol) and potassium acetate (14.9 g, 152 mmol) in 1,4-dioxane (160 mL) was sparged with nitrogen while stirring for 20 min. Dichloro[1,1'-bis(diphenylphosphino)ferrocene]palladium(II) methylene chloride adduct (9.17 g, 12.5 mmol) was then added and the reaction stirred at 90° C. for 16 h. After this time, the mixture was cooled to room temperature, diluted with water (50 mL) and extracted with ethyl acetate (2×100 mL). The combined organic layers were washed with brine (2×50 mL) and dried over sodium sulfate. The drying agent was removed by filtration and the filtrate concentrated under reduced pressure. The resulting residue was purified by column chromatography (silica, gradient, hexanes to 7:13 ethyl acetate/hexanes) to afford 2-(1-methyl-6-(4,4,5,5-tetramethyl-1,3,2-dioxaborolan-2-yl)-1H-indol-3-yl)ethanol as a brown solid: $^1$H NMR (400 MHz, DMSO-d$_6$) δ 7.68 (s, 1H), 7.51 (d, J=8.0 Hz, 1H), 7.32 (d, J=8.0 Hz, 1H), 7.20 (s, 1H), 4.64 (t, J=5.2 Hz, 1H), 3.75 (s, 3H), 3.64-3.59 (m, 2H), 2.83-2.80 (m, 2H), 1.30 (s, 12H).

Example 16

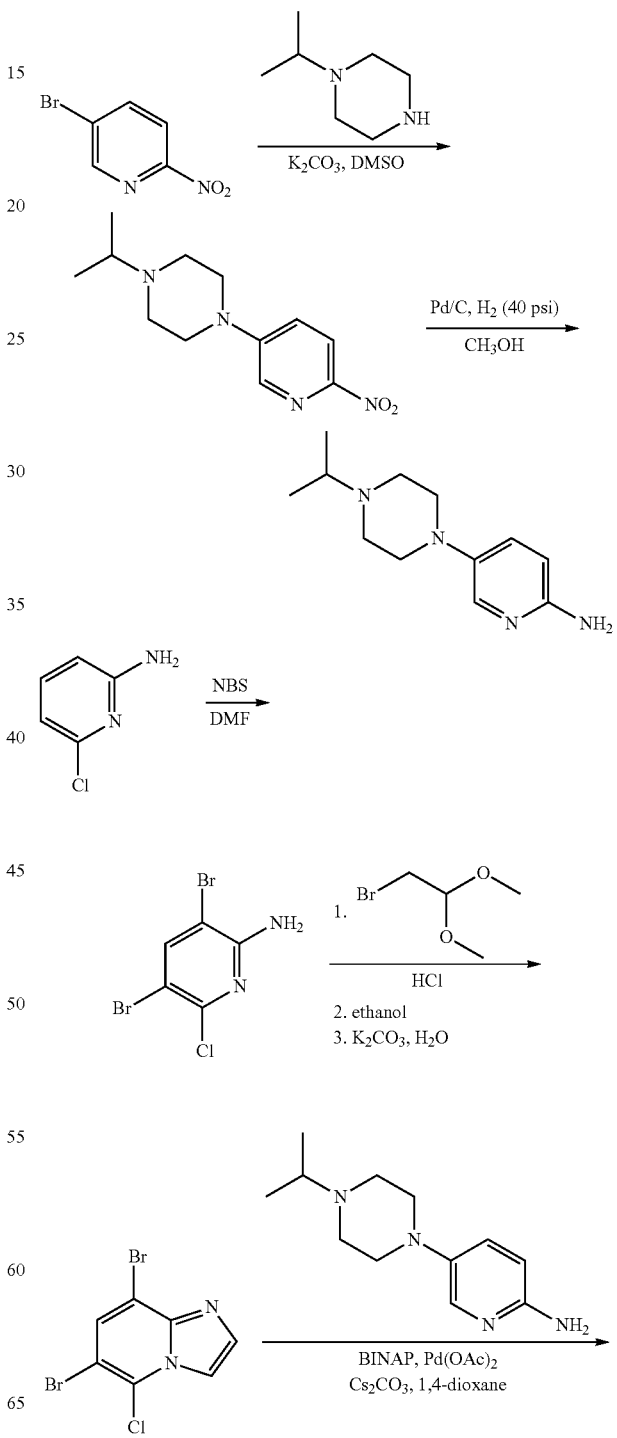

-continued

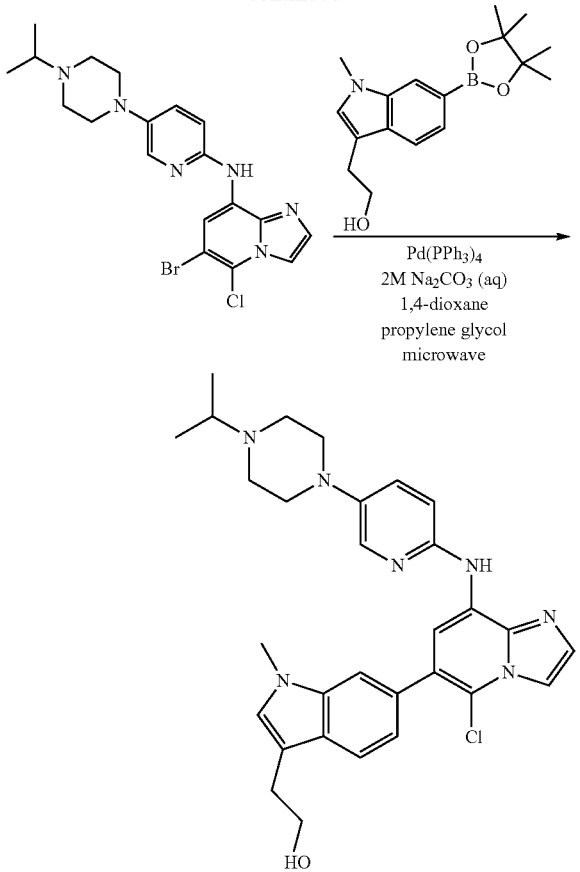

Preparation of 1-isopropyl-4-(6-nitropyridin-3-yl)piperazine

A mixture of 5-bromo-2-nitropyridine (18.0 g, 88.7 mmol), N-isopropylpiperazine (17.1 g, 133 mmol) and potassium carbonate (36.9 g, 267 mol) in dimethylsulfoxide (200 mL) was stirred at 100° C. for 16 h. After this time, the reaction was cooled to room temperature, poured into ice water (500 mL), stirred for 15 min, then extracted with ethyl acetate (2×500 mL). The combined organic layers were dried over sodium sulfate, filtered and the filtrate concentrated under reduced pressure. The resulting residue was dried under vacuum to a constant weight to afford 1-isopropyl-4-(6-nitropyridin-3-yl)piperazine as a yellow solid: $^1$H NMR (400 MHz, CDCl$_3$) δ 8.15 (d, J=9.2 Hz, 1H), 8.12 (d, J=2.8 Hz, 1H), 7.18 (dd, J=9.2, 2.8 Hz, 1H), 3.46 (t, J=4.8 Hz, 4H), 2.78-2.74 (m, 1H), 2.69 (t, J=5.2 Hz, 4H), 1.09 (d, J=10.8 Hz, 6H).

Preparation of 5-(4-isopropylpiperazin-1-yl)pyridin-2-amine

A 500-mL Parr hydrogenation bottle was purged with nitrogen and charged with 1-isopropyl-4-(6-nitropyridin-3-yl)piperazine (14.0 g, 55.9 mmol), methanol (140 mL) and 10% palladium on carbon (50% wet, 4.67 g dry weight). The bottle was evacuated, charged with hydrogen gas to a pressure of 40 psi and shaken for 5 h at room temperature on a Parr hydrogenation apparatus. After this time, the hydrogen gas was evacuated and nitrogen charged into the bottle. The catalyst was removed by filtration through a pad of diatomaceous earth and the filter cake washed with methanol (50 mL). The filtrate was concentrated under reduced pressure to afford 5-(4-isopropylpiperazin-1-yl) pyridin-2-amine as a brown solid which was used in the next step without purification: $^1$H NMR (400 MHz, CDCl$_3$) δ 7.75 (d, J=2.8 Hz, 1H), 7.16 (dd, J=8.4, 2.8 Hz, 1H), 6.46 (d, J=8.4 Hz, 1H), 3.06 (t, J=4.8 Hz, 4H), 2.75 (m, 1H), 2.69 (t, J=4.8 Hz, 4H), 1.09 (d, J=10.4 Hz, 6H), NH$_2$ (m, 2H, not observed).

Preparation of 3,5-dibromo-6-chloropyridine-2-amine

To a stirred solution of 6-chloropyridin-2-amine (50.0 g, 388 mmol) in N,N-dimethylformamide (500 mL) at 0° C., was added N-bromosuccinimide (175 g, 972 mmol) portion wise during which an exotherm was observed. The mixture was allowed to warm to room temperature and stirred for 2 h. After this time, the mixture was poured into ice water (2.0 L) and the resulting suspension was filtered. The filter cake was dissolved in methylene chloride, dried over sodium sulfate, filtered and the filtrate concentrated under reduced pressure. The resulting residue was dried under vacuum to a constant weight to afford 3,5-dibromo-6-chloropyridine-2-amine as a yellow solid: $^1$H NMR (400 MHz, DMSO-d$_6$) δ 8.09 (s, 1H), 6.88 (bs, 2H); MM MS m/z 286.8 [M+2+H]$^+$.

Preparation of 6,8-dibromo-5-chloroimidazo[1,2-a]pyridine

A mixture of 2-bromo-1,1-diethoxyethane (117 mL, 782 mmol) and concentrated hydrochloric acid (71.0 mL) were stirred at reflux for 2 h. After this time, the reaction was cooled to room temperature and treated with sodium bicarbonate (65.7 g, 782 mmol) until gas evolution ceased. The mixture was filtered and the filtrate diluted with ethanol (600 mL). 3,5-Dibromo-6-chloropyridin-2-amine (112 g, 391 mmol) was then added and the mixture stirred at reflux for 16 h. After this time, the reaction was cooled to room temperature and concentrated under reduced pressure. The resulting residue was diluted with water (500 mL) and treated with potassium carbonate (108 g, 782 mmol). The precipitated solids were filtered, dissolved in methylene chloride and dried over sodium sulfate. The drying agent was removed by filtration and the filtrate concentrated under reduced pressure to afford 6,8-dibromo-5-chloroimidazo[1,2-a]pyridine as a brown solid: (400 MHz, DMSO-d$_6$) δ 8.19 (d, J=0.8 Hz, 1H), 8.02 (s, 1H), 7.78 (d, J=0.8 Hz, 1H); MM MS m/z 310.8 [M+2+H]$^+$.

Preparation of 6-bromo-5-chloro-N-(5-(4-isopropylpiperazin-1-yl)pyridin-2-yl)imidazo[1,2-a]pyridin-8-amine A mixture of 5-(4-isopropylpiperazin-1-yl)pyridin-2-amine (1.42 g, 6.44 mmol), 6,8-dibromo-5-chloroimidazo[1,2-a]pyridine (2.00 g, 6.44 mmol), 2,2'-bis(diphenylphosphino)-1,1'-binaphthalene (850 mg, 1.37 mmol) and cesium carbonate (6.50 g, 19.9 mmol) in 1,4-dioxane (100 mL) was purged with nitrogen while stirring for 25 min. Palladium(II) acetate (140 mg, 0.572 mmol) was added and the reaction purged with argon for a further 5 min, then stirred at reflux for 36 h. After this time, the reaction was cooled to room temperature, filtered through a pad of diatomaceous earth and the filter cake washed with a mixture of 1:9 methanol/methylene chloride. The filtrate was concentrated under reduced pressure and the resulting residue purified by column chromatography (silica, gradient, 1:49 methanol/methylene chloride to 1:24 methanol/methylene chloride) to afford 6-bromo-5-chloro-N-(5-(4-isopropylpiperazin-1-yl)pyridin-2-yl)imidazo[1,2-a]pyridin-8-amine as a brown solid: $^1$H NMR (400 MHz, CDCl$_3$) δ 8.56 (s, 1H), 8.06 (d, J=2.8 Hz, 1H), 7.78 (s, 1H), 7.75 (d, J=1.2 Hz, 1H), 7.57 (d, J=1.2 Hz, 1H), 7.31 (dd, J=9.2, 2.8 Hz, 1H), 6.86 (d, J=9.2 Hz, 1H), 3.20-3.18 (m, 4H), 2.79-2.72 (m, 5H), 1.12 (d, J=6.4 Hz, 6H).

Preparation of 2-(6-(5-chloro-8-(5-(4-isopropylpiperazin-1-yl)pyridin-2-ylamino)imidazo[1,2-a]pyridin-6-yl)-1-methyl-1H-indol-3-yl)ethanol A mixture of 2-(1-methyl-6-(4,4,5,5-tetramethyl-1,3,2-dioxaborolan-2-yl)-1H-indol-3-yl)ethanol (570 mg, 1.89 mmol), 6-bromo-5-chloro-N-(5-(4-isopropylpiperazin-1-yl)pyridin-2-yl)imidazo[1,2-a]pyridin-8-amine (500 mg, 1.11 mmol), propylene glycol (0.1 mL) and 2 M aqueous sodium carbonate (1.6 mL) in 1,4-dioxane (15.0 mL) was sparged with nitrogen while stirring for 5 min. Tetrakis (triphenylphosphine)palladium(0) (256 mg, 0.222 mmol) was then added and the reaction heated under microwave irradiation at 145° C. for 30 min. After this time, the reaction was cooled to room temperature and diluted with a mixture of 1:1 methanol/methylene chloride (20 mL). The organic phase was dry loaded onto silica gel and purified by column chromatography (silica, gradient, methylene chloride to 1:24 methanol/methylene chloride) to afford 2-(6-(5-chloro-8-(5-(4-isopropylpiperazin-1-yl)pyridin-2-ylamino)imidazo[1,2-a]pyridin-6-yl)-1-methyl-1H-indol-3-yl)ethanol as an off-white solid: mp 181.1° C.; $^1$H NMR (400 MHz, DMSO-d$_6$) δ 9.09 (s, 1H), 8.49 (s, 1H), 8.05 (s, 1H), 7.89-7.88 (m, 1H), 7.71 (s, 1H), 7.65 (d, J=8.0 Hz, 1H), 7.50 (s, 1H), 7.43-7.35 (m, 1H), 7.35 (d, J=8.4 Hz, 1H), 7.23 (s, 1H), 7.13 (d, J=8.4 Hz, 1H), 4.68 (t, J=5.2 Hz, 1H), 3.77 (s, 3H), 3.70-3.65 (m, 2H), 3.09-3.08 (m, 4H), 2.87 (t, J=7.2 Hz, 2H), 2.72-2.67 (m, 5H), 1.11-1.06 (m, 6H); MM MS m/z 544.2 [M+H]$^+$; HPLC 12.14 min, 97.0% (AUC).

Example 17

The following compounds were prepared using procedures similar to those described above Those of ordinary skill in the art of organic synthesis will recognize when starting materials or reaction conditions should be varied to obtain the desired compound.

MS data reported in this example was obtained as follows: MS conditions: Electrospray MS is performed on a MICROMASS LCT equipped with a LockSpray source for accurate mass measurements. Spectra are acquired in positive ion mode from 100-1000 Da at an acquisition rate of 1 spectrum/0.9 s with a 0.1 s interscan delay. The instrument is tuned for a resolution of 5000 (FWHM). Every 5th scan is taken from the reference position of the Lockspray source. Leucine enkephalin (556.2771 [M+H]$^+$) is used as the reference, or lock mass.

Syk −40 μM data was obtained according to the method disclosed in Example 18 which follows and represents IC$_{50}$ values calculated using a 40 μM ATP solution.

TABLE 1

| Syk IC$_{50}$ and MS Data for Selected Compounds | | | |
|---|---|---|---|
| Structure | Name | IC$_{50}$ @ 40 uM ATP | MH+ m/z |
|  | N-(3,4-dimethoxyphenyl)-6-(1H-indazol-6-yl)imidazo[1,2-a]pyridin-8-amine | 1049.1 | 386.4 |
|  | N-[6-(1H-indazol-6-yl)imidazo[1,2-a]pyridin-8-yl]-5,6-dimethoxypyridin-2-amine | 3.8 | 387.3 |

TABLE 1-continued

Syk IC$_{50}$ and MS Data for Selected Compounds

| Structure | Name | IC$_{50}$ @ 40 uM ATP | MH+ m/z |
|---|---|---|---|
| 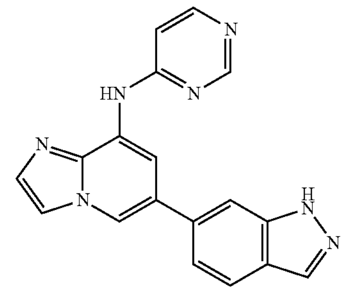 [SMILES: c1cc(Nc2cc(-c3ccc4cn[nH]c4c3)cn3ccnc23)ncn1] | N-[6-(1H-indazol-6-yl)imidazo[1,2-a]pyridin-8-yl]pyrimidin-4-amine | 297.2 | 328.3 |
| 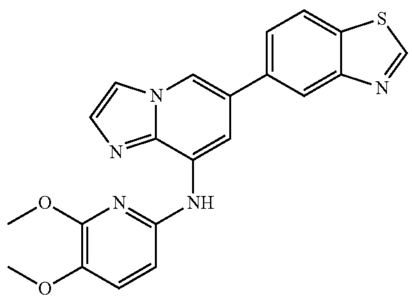 [SMILES: COc1ccc(Nc2cc(-c3ccc4scnc4c3)cn3ccnc23)nc1OC] | N-[6-(1,3-benzothiazol-5-yl)imidazo[1,2-a]pyridin-8-yl]-5,6-dimethoxypyridin-2-amine | 18.2 | 404.6 |
| 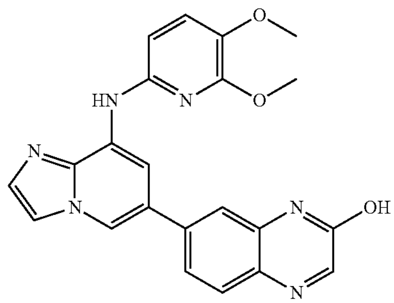 [SMILES: COc1ccc(Nc2cc(-c3ccc4ncc(O)nc4c3)cn3ccnc23)nc1OC] | 7-{8-[(5,6-dimethoxypyridin-2-yl)amino]imidazo[1,2-a]pyridin-6-yl}quinoxalin-2-ol | 22.4 | 415.6 |
| 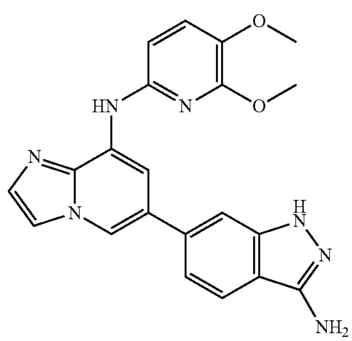 [SMILES: COc1ccc(Nc2cc(-c3ccc4c(N)n[nH]c4c3)cn3ccnc23)nc1OC] | 6-{8-[(5,6-dimethoxypyridin-2-yl)amino]imidazo[1,2-a]pyridin-6-yl}-1H-indazol-3-amine | 13.3 | 402.4 |
| 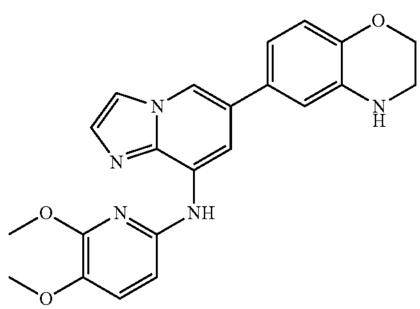 [SMILES: COc1ccc(Nc2cc(-c3ccc4c(c3)NCCO4)cn3ccnc23)nc1OC] | N-[6-(3,4-dihydro-2H-1,4-benzoxazin-6-yl)imidazo[1,2-a]pyridin-8-yl]-5,6-dimethoxypyridin-2-amine | 23.7 | 404.7 |

TABLE 1-continued

Syk IC$_{50}$ and MS Data for Selected Compounds

| Structure | Name | IC$_{50}$ @ 40 uM ATP | MH+ m/z |
|---|---|---|---|
| 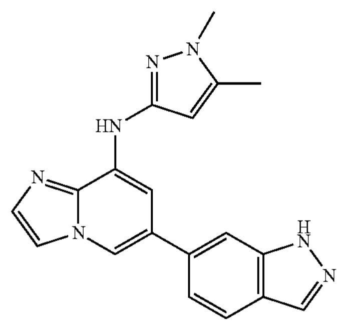 [SMILES: Cc1cc(Nc2cc(-c3ccc4cn[nH]c4c3)cn3ccnc23)nn1C] | N-[6-(1H-indazol-6-yl)imidazo[1,2-a]pyridin-8-yl]-1,5-dimethyl-1H-pyrazol-3-amine | 6.2 | 343.9 |
| 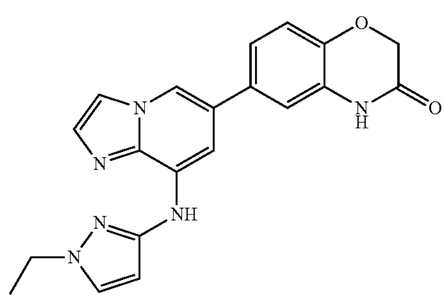 [SMILES: CCn1ccc(Nc2cc(-c3ccc4c(c3)NC(=O)CO4)cn3ccnc23)n1] | 6-{8-[(1-ethyl-1H-pyrazol-3-yl)amino]imidazo[1,2-a]pyridin-6-yl}-3,4-dihydro-2H-1,4-benzoxazin-3-one | 548.1 | 375.2 |
| 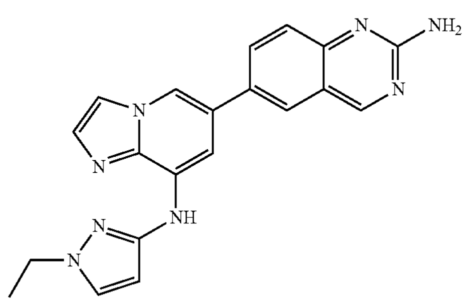 [SMILES: CCn1ccc(Nc2cc(-c3ccc4nc(N)ncc4c3)cn3ccnc23)n1] | 6-{8-[(1-ethyl-1H-pyrazol-3-yl)amino]imidazo[1,2-a]pyridin-6-yl}quinazolin-2-amine | 171.3 | 371.1 |
| 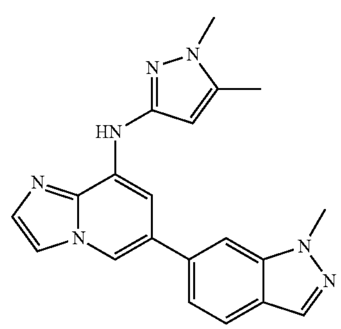 [SMILES: Cc1cc(Nc2cc(-c3ccc4cnn(C)c4c3)cn3ccnc23)nn1C] | 1,5-dimethyl-N-[6-(1-methyl-1H-1,3-benzodiazol-6-yl)imidazo[1,2-a]pyridin-8-yl]-1H-pyrazol-3-amine | 181.9 | 358.5 |

TABLE 1-continued

Syk IC$_{50}$ and MS Data for Selected Compounds

| Structure | Name | IC$_{50}$ @ 40 uM ATP | MH+ m/z |
|---|---|---|---|
| 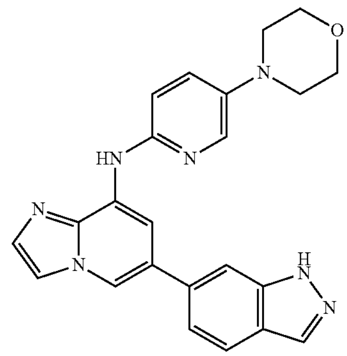 [SMILES: c1cn2cc(-c3ccc4cn[nH]c4c3)cc(Nc3ccc(N4CCOCC4)cn3)c2n1] | N-[6-(1H-indazol-6-yl)imidazo[1,2-a]pyridin-8-yl]-5-(morpholin-4-yl)pyridin-2-amine | 6.6 | 412.4 |
| 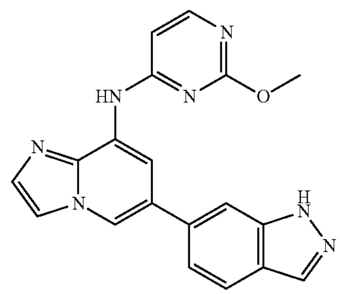 [SMILES: COc1nccc(Nc2cc(-c3ccc4cn[nH]c4c3)cn3ccnc23)n1] | N-[6-(1H-indazol-6-yl)imidazo[1,2-a]pyridin-8-yl]-2-methoxypyrimidin-4-amine | 40.5 | 358.2 |
| 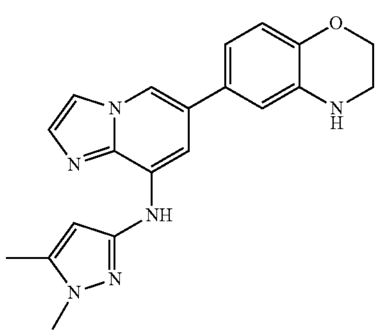 [SMILES: Cc1cc(Nc2cc(-c3ccc4c(c3)NCCO4)cn3ccnc23)nn1C] | N-[6-(3,4-dihydro-2H-1,4-benzoxazin-6-yl)imidazo[1,2-a]pyridin-8-yl]-1,5-dimethyl-1H-pyrazol-3-amine | 153.7 | 361.8 |
| 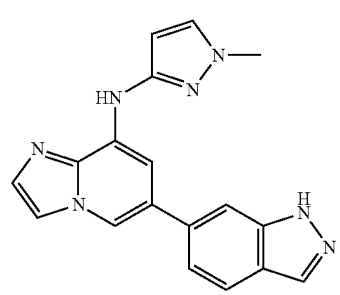 [SMILES: Cn1ccc(Nc2cc(-c3ccc4cn[nH]c4c3)cn3ccnc23)n1] | N-[6-(1H-indazol-6-yl)imidazo[1,2-a]pyridin-8-yl]-1-methyl-1H-pyrazol-3-amine | 35.5 | 330.1 |

TABLE 1-continued

Syk IC$_{50}$ and MS Data for Selected Compounds

| Structure | Name | IC$_{50}$ @ 40 uM ATP | MH+ m/z |
|---|---|---|---|
| 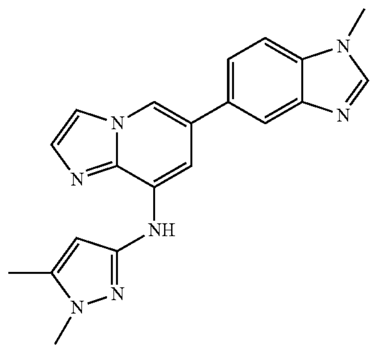 [SMILES: Cc1cc(Nc2cc(-c3ccc4c(c3)ncn4C)cn3ccnc23)nn1C] | 1,5-dimethyl-N-[6-(1-methyl-1H-1,3-benzodiazol-5-yl)imidazo[1,2-a]pyridin-8-yl]-1H-pyrazol-3-amine | 187.6 | 358.4 |
| 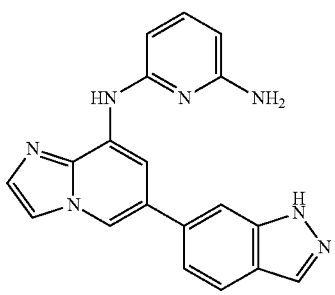 [SMILES: Nc1cccc(Nc2cc(-c3ccc4cn[nH]c4c3)cn3ccnc23)n1] | 2-N-[6-(1H-indazol-6-yl)imidazo[1,2-a]pyridin-8-yl]pyridine-2,6-diamine | 23.1 | 342.3 |
| 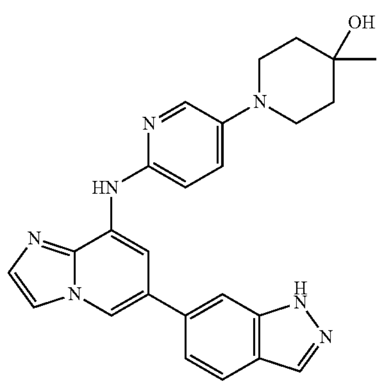 [SMILES: CC1(O)CCN(c2ccc(Nc3cc(-c4ccc5cn[nH]c5c4)cn4ccnc34)nc2)CC1] | 1-(6-{[6-(1H-indazol-6-yl)imidazo[1,2-a]pyridin-8-yl]amino}pyridin-3-yl)-4-methylpiperidin-4-ol | 6 | 440.5 |
| 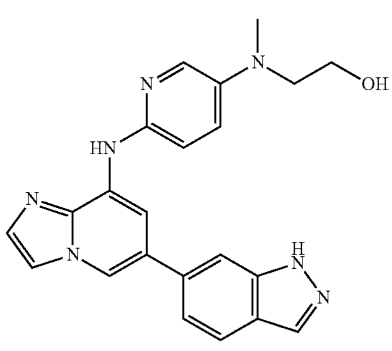 [SMILES: CN(CCO)c1ccc(Nc2cc(-c3ccc4cn[nH]c4c3)cn3ccnc23)nc1] | 2-[(6-{[6-(1H-indazol-6-yl)imidazo[1,2-a]pyridin-8-yl]amino}pyridin-3-yl)(methyl)amino]ethan-1-ol | 9 | 400.2 |

TABLE 1-continued

Syk IC$_{50}$ and MS Data for Selected Compounds

| Structure | Name | IC$_{50}$ @ 40 uM ATP | MH+ m/z |
|---|---|---|---|
| 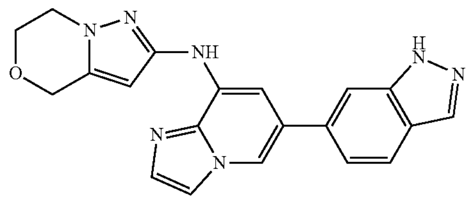 [SMILES: c1cn2cc(-c3ccc4cn[nH]c4c3)cc(Nc3cc4n(n3)CCOC4)c2n1] | 6-(1H-indazol-6-yl)-N-{4H,6H,7H-pyrazolo[3,2-c][1,4]oxazin-2-yl}imidazo[1,2-a]pyridin-8-amine | 2 | 372.3 |
| 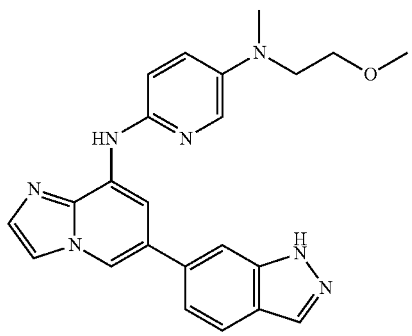 [SMILES: COCCN(C)c1ccc(Nc2cc(-c3ccc4cn[nH]c4c3)cn3ccnc23)nc1] | 2-N-[6-(1H-indazol-6-yl)imidazo[1,2-a]pyridin-8-yl]-5-N-(2-methoxyethyl)-5-N-methylpyridin-2,5-diamine | 13 | 414.2 |
| 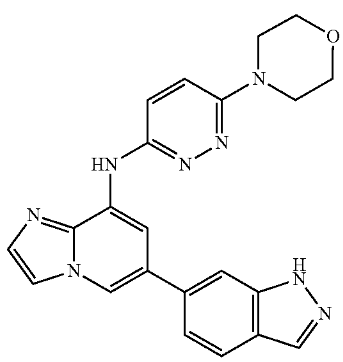 [SMILES: c1cn2cc(-c3ccc4cn[nH]c4c3)cc(Nc3ccc(N4CCOCC4)nn3)c2n1] | N-[6-(1H-indazol-6-yl)imidazo[1,2-a]pyridin-8-yl]-6-(morpholin-4-yl)pyradazin-3-amine | 5 | 413.4 |
| 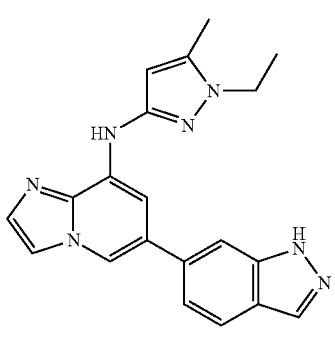 [SMILES: CCn1nc(Nc2cc(-c3ccc4cn[nH]c4c3)cn3ccnc23)cc1C] | 1-ethyl-N-[6-(1H-indazol-6-yl)imidazo[1,2-a]pyridin-8-yl]-5-methyl-1H-pyrazol-3-amine | 39 | 358.2 |

TABLE 1-continued

Syk IC$_{50}$ and MS Data for Selected Compounds

| Structure | Name | IC$_{50}$ @ 40 uM ATP | MH+ m/z |
|---|---|---|---|
| 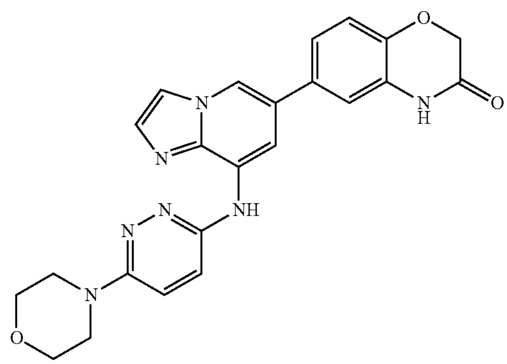 [SMILES: O=C1COc2ccc(-c3cc(Nc4ccc(N5CCOCC5)nn4)c4nccn4c3)cc2N1] | 6-(8-{[6-(morpholin-4-yl)pyridazin-3-yl]amino}imidazo[1,2-a]pyridin-6-yl)-3,4-dihydro-2H-1,4-benzoxazin-3-one | 15 | 444.8 |
| 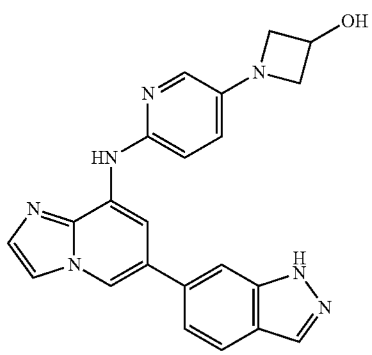 [SMILES: OC1CN(c2ccc(Nc3cc(-c4ccc5cn[nH]c5c4)cn4ccnc34)nc2)C1] | 1-(6-{[6-(1H-indazol-6-yl)imidazo[1,2-a]pyridin-8-yl]amino}pyridin-3-yl)azetidin-3-ol | 5 | 398.1 |
| 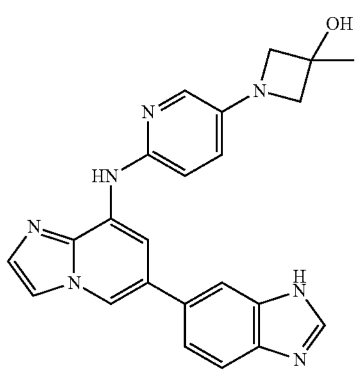 [SMILES: CC1(O)CN(c2ccc(Nc3cc(-c4ccc5nc[nH]c5c4)cn4ccnc34)nc2)C1] | 1-(6-{[6-(1H-indazol-6-yl)imidazo[1,2-a]pyridin-8-yl]amino}pyridin-3-yl)-3-methylazetidin-3-ol | 20 | 412.4 |
| 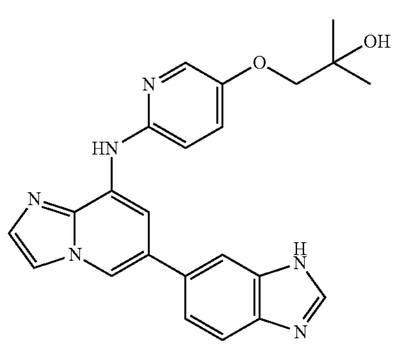 [SMILES: CC(C)(O)COc1ccc(Nc2cc(-c3ccc4nc[nH]c4c3)cn3ccnc23)nc1] | 1-[(6-{[6-(1H-indazol-6-yl)imidazo[1,2-a]pyridin-8-yl]amino}pyridin-3-yl)oxy]-2-methylpropan-2-ol | 8 | 415.6 |

TABLE 1-continued

Syk IC$_{50}$ and MS Data for Selected Compounds

| Structure | Name | IC$_{50}$ @ 40 uM ATP | MH+ m/z |
|---|---|---|---|
| 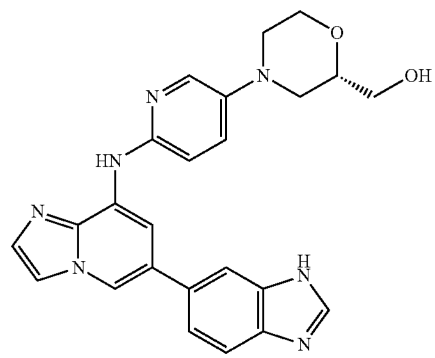 [SMILES: OC[C@@H]1CN(c2ccc(Nc3cc(-c4ccc5nc[nH]c5c4)cn4ccnc34)nc2)CCO1] | [(2S)-4-(6-{[6-(1H-indazol-6-yl)imidazo[1,2-a]pyridin-8-yl]amino}pyridin-3-yl)morpholin-2-yl]methanol | 8 | 442.4 |
| 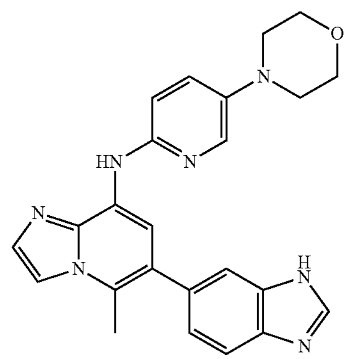 | N-[6-(1H-indazol-6-yl)-5-methylimidazo[1,2-a]pyridin-8-yl]-5-(morpholin-4-yl)pyridin-2-amine | 15 | 426.2 |
| 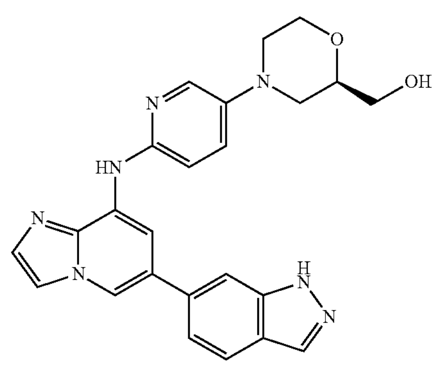 [SMILES: OC[C@H]1CN(c2ccc(Nc3cc(-c4ccc5cn[nH]c5c4)cn4ccnc34)nc2)CCO1] | [(2R)-4-(6-{[6-(1H-indazol-6-yl)imidazo[1,2-a]pyridin-8-yl]amino}pyridin-3-yl)morpholin-2-yl]methanol | 5 | 442.6 |
| 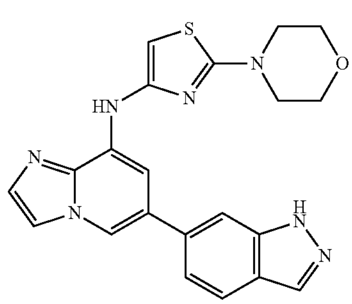 [SMILES: c1cn2cc(-c3ccc4cn[nH]c4c3)cc(Nc3csc(N4CCOCC4)n3)c2n1] | N-[6-(1H-indazol-6-yl)imidazo[1,2-a]pyridin-8-yl]-2-(morpholin-4-yl)-1,3-thiazol-4-amine | 290.9 | 418.2 |

TABLE 1-continued

Syk IC$_{50}$ and MS Data for Selected Compounds

| Structure | Name | IC$_{50}$ @ 40 uM ATP | MH+ m/z |
|---|---|---|---|
| 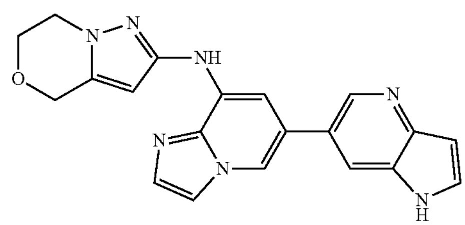 [SMILES: c1cn2cc(-c3cnc4cc[nH]c4c3)cc(Nc3cc4n(n3)CCOC4)c2n1] | N-{4H,6H,7H-pyrazolo[3,2-c][1,4]oxazin-2-yl}-6-{1H-pyrrolo[3,2-b]pyridin-6-yl}imidazo[1,2-a]pyridin-8-amine | 4.5 | 372 |
| 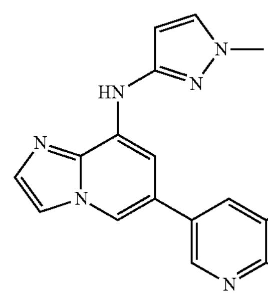 | 1-methyl-N-(6-{1H-pyrrolo[3,2-b]pyridin-6-yl}imidazo[1,2-a]pyridin-8-yl)-1H-pyrazol-3-amine | 23.2 | 330.1 |
| 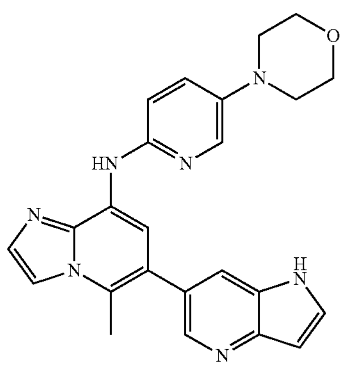 [SMILES: Cc1c(-c2cnc3cc[nH]c3c2)cc(Nc2ccc(N3CCOCC3)cn2)c2nccn12] | N-(5-methyl-6-{1H-pyrrolo[3,2-b]pyridin-6-yl}imidazo[1,2-a]pyridin-8-yl)-5-(morpholin-4-yl)pyridin-2-amine | 38 | 426 |
| 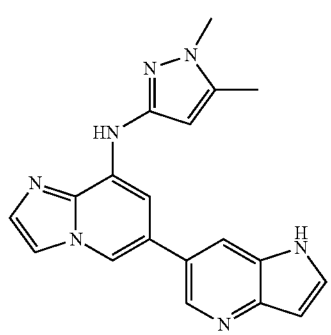 [SMILES: Cc1cc(Nc2cc(-c3cnc4cc[nH]c4c3)cn3ccnc23)nn1C] | 1,5-dimethyl-N-(6-{1H-pyrrolo[3,2-b]pyridin-6-yl}imidazo[1,2-a]pyridin-8-yl)-1H-pyrazol-3-amine | 10.5 | 344.1 |

TABLE 1-continued

Syk IC$_{50}$ and MS Data for Selected Compounds

| Structure | Name | IC$_{50}$ @ 40 uM ATP | MH+ m/z |
|---|---|---|---|
| 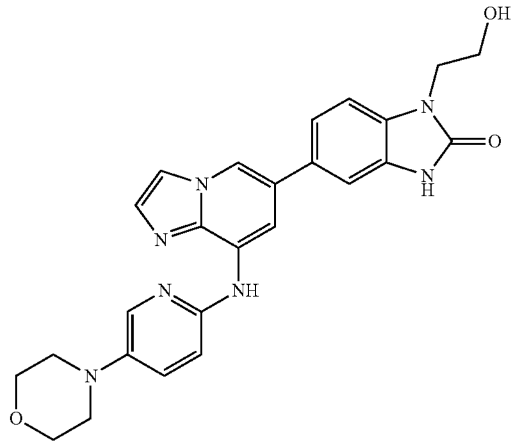 [SMILES: O=c1[nH]c2cc(-c3cc(Nc4ccc(N5CCOCC5)cn4)c4nccn4c3)ccc2n1CCO] | 1-(2-hydroxyethyl)-5-(8-{[5-(morpholin-4-yl)pyridin-2-yl]amino}imidazo[1,2-a]pyridin-6-yl)-2,3-dihydro-1H-1,3-benzodiazol-2-one | 25.2 | 472.1 |
| 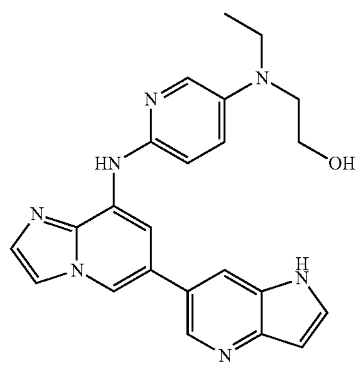 [SMILES: CCN(CCO)c1ccc(Nc2cc(-c3cnc4cc[nH]c4c3)cn3ccnc23)nc1] | 2-[ethyl({6-[(6-{1H-pyrrolo[3,2-b]pyridin-6-yl}imidazo[1,2-a]pyridin-8-yl)amino]pyridin-3-yl})amino]ethan-1-ol | 8.5 | 414.4 |
| 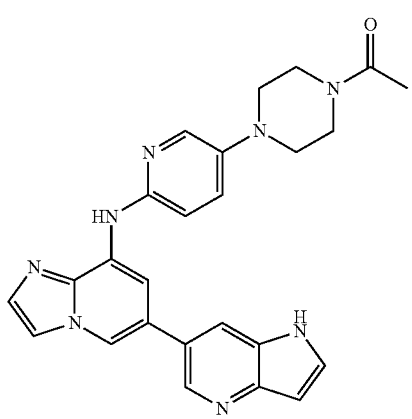 [SMILES: CC(=O)N1CCN(c2ccc(Nc3cc(-c4cnc5cc[nH]c5c4)cn4ccnc34)nc2)CC1] | 1-(4-{6-[(6-{1H-pyrrolo[3,2-b]pyridin-6-yl}imidazo[1,2-a]pyridin-8-yl)amino]pyridin-3-yl}piperazin-1-yl)ethan-1-one | 4.29 | 453.1 |

TABLE 1-continued

Syk IC$_{50}$ and MS Data for Selected Compounds

| Structure | Name | IC$_{50}$ @ 40 uM ATP | MH+ m/z |
|---|---|---|---|
| 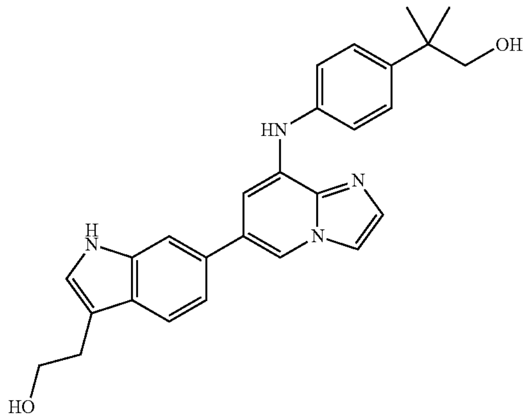 [SMILES: CC(C)(CO)c1ccc(Nc2cc(-c3ccc4c(CCO)c[nH]c4c3)cn3ccnc23)cc1] | 2-[4-({6-[3-(2-hydroxyethyl)-1H-indol-6-yl]imidazo[1,2-a]pyridin-8-yl}amino)phenyl]-2-methylpropan-1-ol | 138 | 441.4 |
| 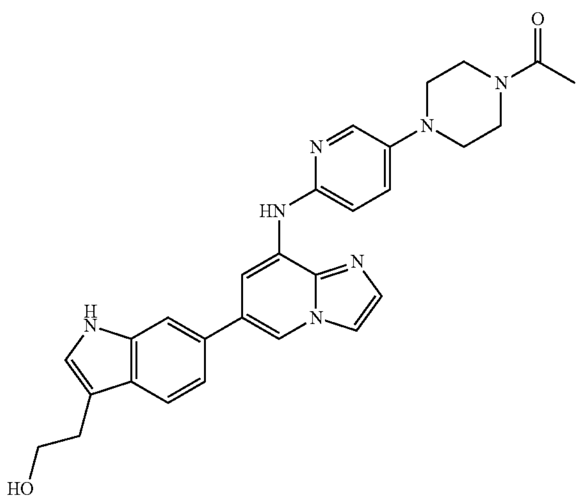 [SMILES: CC(=O)N1CCN(c2ccc(Nc3cc(-c4ccc5c(CCO)c[nH]c5c4)cn4ccnc34)nc2)CC1] | 1-{4-[6-({6-[3-(2-hydroxyethyl)-1H-indol-6-yl]imidazo[1,2-a]pyridin-8-yl}amino)pyridin-3-yl]piperazin-1-yl}ethan-1-one | 25 | 496.8 |
| 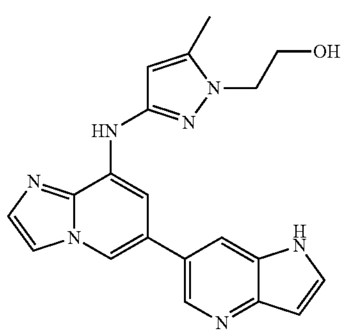 [SMILES: Cc1cc(Nc2cc(-c3cnc4cc[nH]c4c3)cn3ccnc23)nn1CCO] | 2-{5-methyl-3-[(6-{1H-pyrrolo[3,2-b]pyridin-6-yl}imidazo[1,2-a]pyridin-8-yl)amino]-1H-pyrazol-1-yl}ethan-1-one | 54 | 374.2 |
| 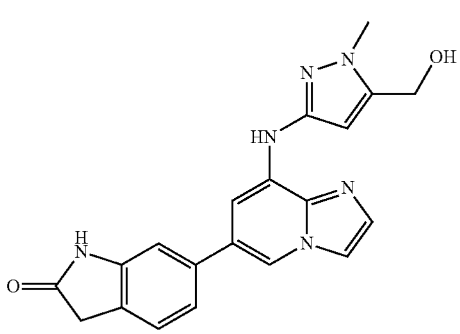 [SMILES: Cn1nc(Nc2cc(-c3ccc4c(c3)NC(=O)C4)cn3ccnc23)cc1CO] | 6-(8-{[5-(hydroxymethyl)-1-methyl-1H-pyrazol-3-yl]amino}imidazo[1,2-a]pyridin-6-yl)-2,3-dihydro-1H-indol-2-one | 13 | 375.1 |

TABLE 1-continued

Syk IC₅₀ and MS Data for Selected Compounds

| Structure | Name | IC$_{50}$ @ 40 uM ATP | MH+ m/z |
|---|---|---|---|
| 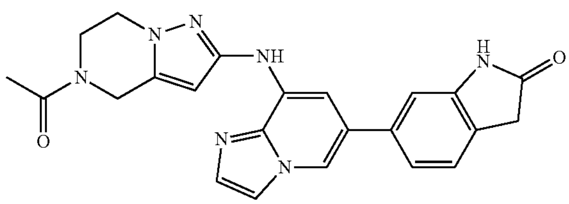 [SMILES: CC(=O)N1CCn2nc(Nc3cc(-c4ccc5c(c4)NC(=O)C5)cn4ccnc34)cc2C1] | 6-[8-({5-acetyl-4H,5H,6H,7H-pyrazolo[1,5-a]pyrazin-2-yl}amino)imidazo[1,2-a]pyridin-6-yl]-2,3-dihydro-1H-indol-2-one | 18 | 428.2 |
| 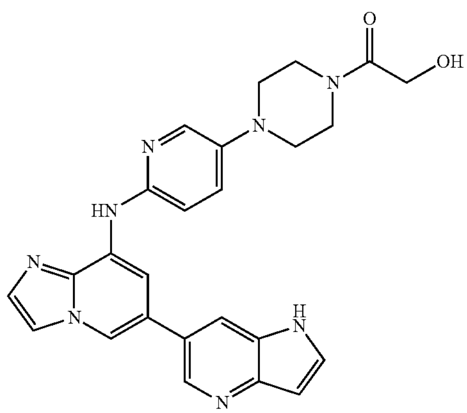 [SMILES: O=C(CO)N1CCN(c2ccc(Nc3cc(-c4cnc5cc[nH]c5c4)cn4ccnc34)nc2)CC1] | 2-hydroxy-1-(4-{6-[(6-{1H-pyrrolo[3,2-b]pyridin-6-yl}imidazo[1,2-a]pyridin-8-yl)amino]pyridin-3-yl}piperazin-1-yl)ethan-1-one | 2.6 | 469.4 |
| 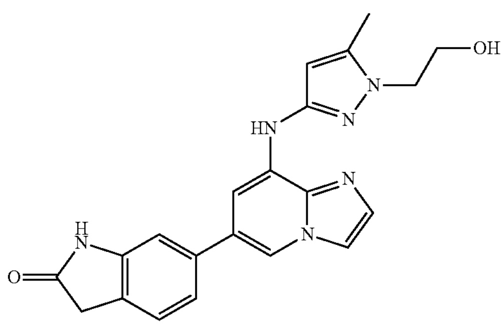 [SMILES: Cc1cc(Nc2cc(-c3ccc4c(c3)NC(=O)C4)cn3ccnc23)nn1CCO] | 6-(8-{[1-(2-hydroxyethyl)-5-methyl-1H-pyrazol-3-yl]amino}imidazo[1,2-a]pyridin-6-yl)-2,3-dihydro-1H-indol-2-one | 43.2 | 389.5 |
| 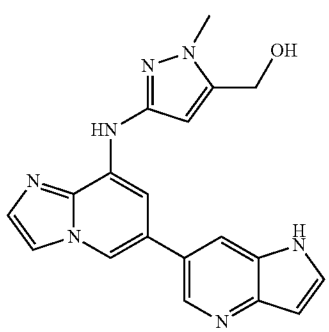 [SMILES: Cn1nc(Nc2cc(-c3cnc4cc[nH]c4c3)cn3ccnc23)cc1CO] | {1-methyl-3-[(6-{1H-pyrrolo[3,2-b]pyridin-6-yl}imidazo[1,2-a]pyridin-8-yl)amino]-1H-pyrazol-5-yl}methanol | 20.8 | 360.1 |
| 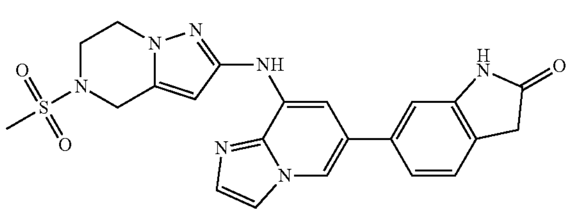 [SMILES: CS(=O)(=O)N1CCn2nc(Nc3cc(-c4ccc5c(c4)NC(=O)C5)cn4ccnc34)cc2C1] | 6-[8-({5-methanesulfonyl-4H,5H,6H,7H-pyrazolo[1,5-a]pyrazin-2-yl}amino)imidazo[1,2-a]pyridin-6-yl]-2,3-dihydro-1H-indol-2-one | 10 | 464.2 |

TABLE 1-continued

Syk IC$_{50}$ and MS Data for Selected Compounds

| Structure | Name | IC$_{50}$ @ 40 uM ATP | MH+ m/z |
|---|---|---|---|
|  | N-{5-methanesulfonyl-4H,5H,6H,7H-pyrazolo[1,5-a]pyrazin-2-yl}-6-{1H-pyrrolo[3,2-b]pyridin-6-yl}imidazo[1,2-a]pyridin-8-amine | 3.7 | 449 |
| 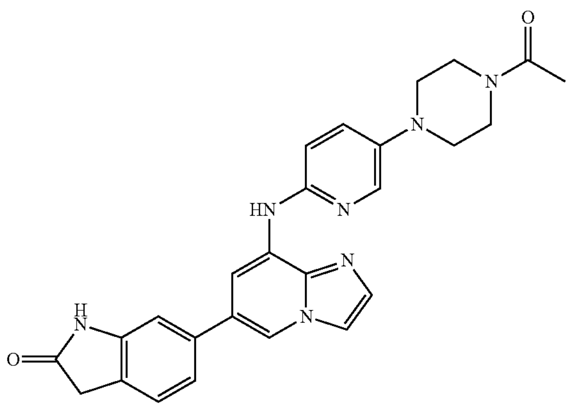 [SMILES: CC(=O)N1CCN(c2ccc(Nc3cc(-c4ccc5c(c4)NC(=O)C5)cn4ccnc34)nc2)CC1] | 6-(8-{[5-(4-acetylpiperazin-1-yl)pyridin-2-yl]amino}imidazo[1,2-a]pyridin-6-yl)-2,3-dihydro-1H-indol-2-one | 15.5 | 468.3 |
| 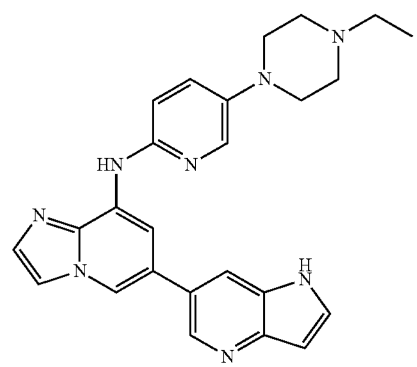 [SMILES: CCN1CCN(c2ccc(Nc3cc(-c4cnc5cc[nH]c5c4)cn4ccnc34)nc2)CC1] | 5-(4-ethylpiperazin-1-yl)-N-(6-{1H-pyrrolo[3,2-b]pyridin-6-yl}imidazo[1,2-a]pyridin-8-yl)pyridin-2-amine | 11.3 | 439.6 |
| 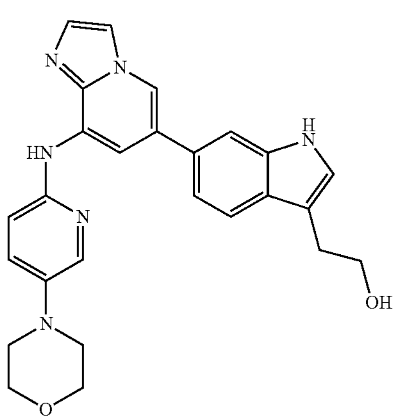 [SMILES: OCCc1c[nH]c2cc(-c3cc(Nc4ccc(N5CCOCC5)cn4)c4nccn4c3)ccc12] | 2-(6-(8-(5-morpholinopyridin-2-ylamino)imidazo[1,2-a]pyridin-6-yl)-1H-indol-3-yl)ethanol | 23.9 | 455.3 |

TABLE 1-continued

Syk IC$_{50}$ and MS Data for Selected Compounds

| Structure | Name | IC$_{50}$ @ 40 uM ATP | MH+ m/z |
|---|---|---|---|
| 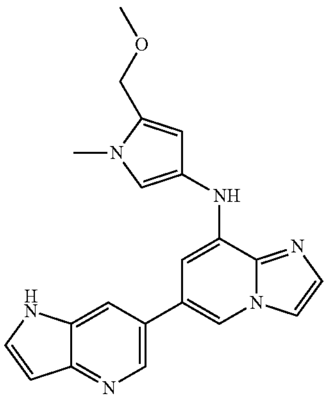 [SMILES: COCc1cc(Nc2cc(-c3cnc4cc[nH]c4c3)cn3ccnc23)cn1C] | N-(5-(methoxymethyl)-1-methyl-1H-pyrazol-3-yl)-6-(1H-pyrrolo[3,2-b]pyridin-6-yl)imidazo[1,2-a]pyridin-8-amine | 10.9 | 374.1 |
| 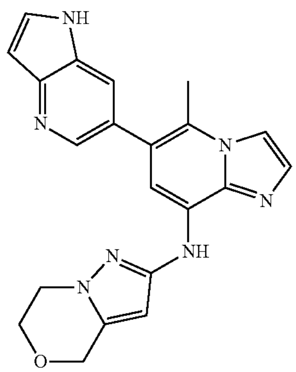 [SMILES: Cc1c(-c2cnc3cc[nH]c3c2)cc(Nc2cc3n(n2)CCOC3)c2nccn12] | N-(5-methyl-6-(1H-pyrrolo[3,2-b]pyridin-6-yl)imidazo[1,2-a]pyridin-8-yl)-6,7-dihydro-4H-pyrazolo[5,1-c][1,4]oxazin-2-amine | 7.7 | 386.2 |
| 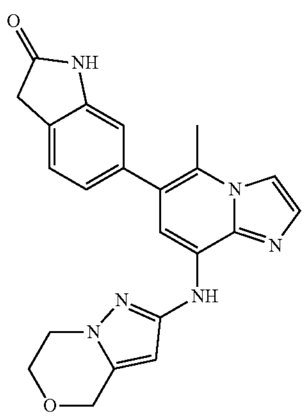 [SMILES: Cc1c(-c2ccc3c(c2)NC(=O)C3)cc(Nc2cc3n(n2)CCOC3)c2nccn12] | 6-(8-(6,7-dihydro-4H-pyrazolo[5,1-c][1,4]oxazin-2-ylamino)-5-methylimidazo[1,2-a]pyridin-6-yl)indolin-2-one | 10.8 | 455.3 |
| 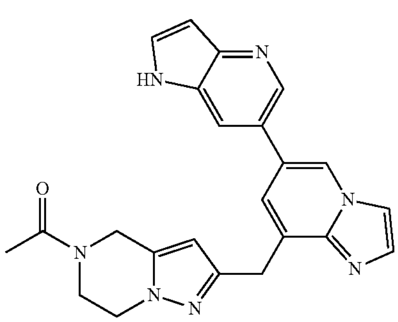 [SMILES: CC(=O)N1CCn2nc(Cc3cc(-c4cnc5cc[nH]c5c4)cn4ccnc34)cc2C1] | 1-(2-(6-(1H-pyrrolo[3,2-b]pyridin-6-yl)imidazo[1,2-a]pyridin-8-ylamino)-6,7-dihydropyrazolo[1,5-a]pyrazin-5(4H)-yl)ethanone | 2.8 | 374.1 |

TABLE 1-continued

Syk IC$_{50}$ and MS Data for Selected Compounds

| Structure | Name | IC$_{50}$ @ 40 uM ATP | MH+ m/z |
|---|---|---|---|
| 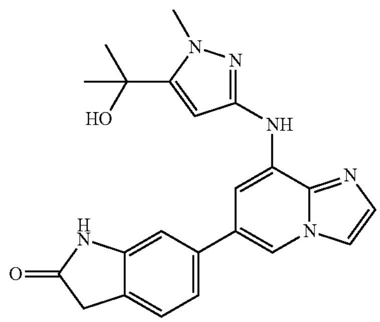 [SMILES: Cn1nc(Nc2cc(-c3ccc4c(c3)NC(=O)C4)cn3ccnc23)cc1C(C)(C)O] | 6-(8-(5-(2-hydroxypropan-2-yl)-1-methyl-1H-pyrazol-3-ylamino)imidazo[1,2-a]pyridin-6-yl)indolin-2-one | 41.5 | 386.2 |
| 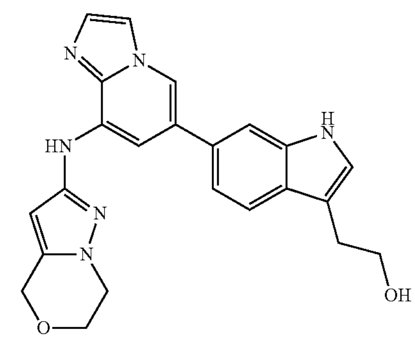 [SMILES: OCCc1c[nH]c2cc(-c3cc(Nc4cc5n(n4)CCOC5)c4nccn4c3)ccc12] | 2-(6-(8-(6,7-dihydro-4H-pyrazolo[5,1-c][1,4]oxazin-2-ylamino)imidazo[1,2-a]pyridin-6-yl)-1H-indol-3-yl)ethanol | 7.1 | 401.2 |
| 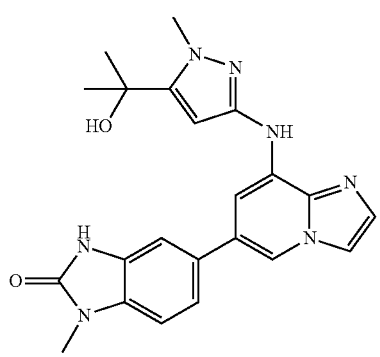 [SMILES: Cn1nc(Nc2cc(-c3ccc4c(c3)[nH]c(=O)n4C)cn3ccnc23)cc1C(C)(C)O] | 5-(8-(5-(2-hydroxypropan-2-yl)-1-methyl-1H-pyrazol-3-ylamino)imidazo[1,2-a]pyridin-6-yl)-1-methyl-1H-benzo[d]imidazol-2(3H)-one | 19.7 | 413.5 |
| 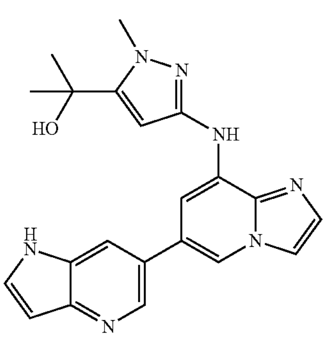 [SMILES: Cn1nc(Nc2cc(-c3cnc4cc[nH]c4c3)cn3ccnc23)cc1C(C)(C)O] | 2-(3-(6-(1H-pyrrolo[3,2-b]pyridin-6-yl)imidazo[1,2-a]pyridin-8-ylamino)-1-methyl-1H-pyrazol-5-yl)propan-2-ol | 44.8 | 403.1 |

TABLE 1-continued

Syk IC$_{50}$ and MS Data for Selected Compounds

| Structure | Name | IC$_{50}$ @ 40 uM ATP | MH+ m/z |
|---|---|---|---|
| 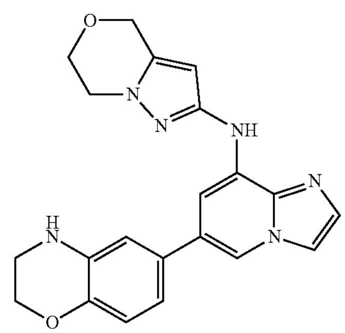 [SMILES: c1cn2cc(-c3ccc4c(c3)NCCO4)cc(Nc3cc4n(n3)CCOC4)c2n1] | N-(6-(3,4-dihydro-2H-benzo[b][1,4]oxazin-6-yl)imidazo[1,2-a]pyridin-8-yl)-6,7-dihydro-4H-pyrazolo[5,1-c][1,4]oxazin-2-amine | 49.3 | 415.6 |
| 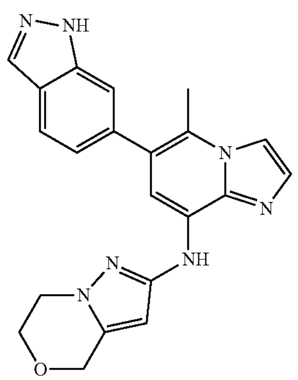 [SMILES: Cc1c(-c2ccc3cn[nH]c3c2)cc(Nc2cc3n(n2)CCOC3)c2nccn12] | N-(6-(1H-indazol-6-yl)-5-methylimidazol[1,2-a]pyridin-8-yl)-6,7-dihydro-4H-pyrazolo[5,1-c][1,4]oxazin-2-amine | 12.8 | 418.1 |
| 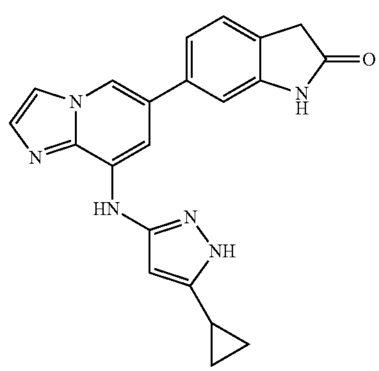 [SMILES: O=C1Cc2ccc(-c3cc(Nc4cc(C5CC5)[nH]n4)c4nccn4c3)cc2N1] | 6-(8-(5-cyclopropyl-1H-pyrazol-3-ylamino)imidazo[1,2-a]pyridin-6-yl)indolin-2-one | 26 | 388.1 |
| 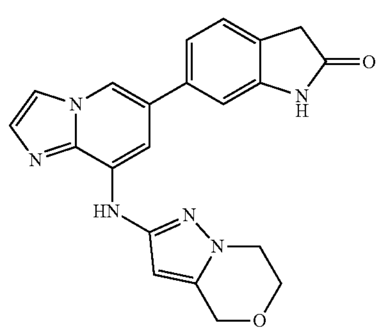 [SMILES: O=C1Cc2ccc(-c3cc(Nc4cc5n(n4)CCOC5)c4nccn4c3)cc2N1] | 6-(8-(6,7-dihydro-4H-pyrazolo[5,1-c][1,4]oxazin-2-ylamino)imidazo[1,2-a]pyridin-6-yl)indolin-2-one | 34 | 389.7 |

TABLE 1-continued

Syk IC$_{50}$ and MS Data for Selected Compounds

| Structure | Name | IC$_{50}$ @ 40 uM ATP | MH+ m/z |
|---|---|---|---|
| 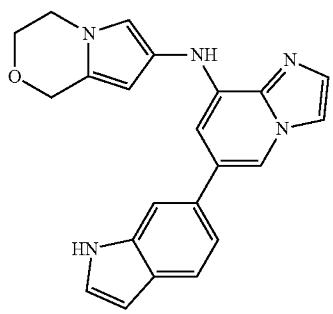 [SMILES: c1cn2cc(-c3ccc4cc[nH]c4c3)cc(Nc3cc4n(c3)CCOC4)c2n1] | N-(6-(1H-indol-6-yl)imidazo[1,2-a]pyridin-8-yl)-6,7-dihydro-4H-pyrazolo[5,1-c][1,4]oxazin-2-amine | 13 | 386.1 |
| 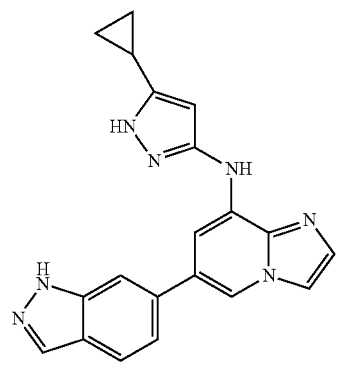 [SMILES: c1cn2cc(-c3ccc4cn[nH]c4c3)cc(Nc3cc(C4CC4)[nH]n3)c2n1] | N-(5-cyclopropyl-1H-pyrazol-3-yl)-6-(1H-indazol-6-yl)imidazo[1,2-a]pyridin-8-amine | 22 | 371 |
| 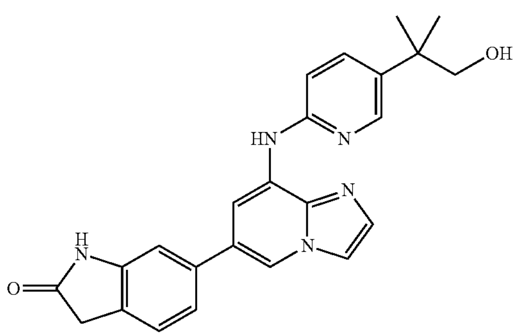 [SMILES: CC(C)(CO)c1ccc(Nc2cc(-c3ccc4c(c3)NC(=O)C4)cn3ccnc23)nc1] | 6-(8-(5-(1-hydroxy-2-methylpropan-2-yl)pyridin-2-ylamino)imidazo[1,2-a]pyridin-6-yl)indolin-2-one | 19 | 387.4 |
| 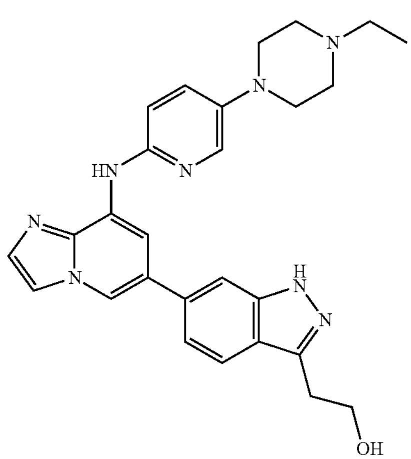 [SMILES: CCN1CCN(c2ccc(Nc3cc(-c4ccc5c(CCO)n[nH]c5c4)cn4ccnc34)nc2)CC1] | 2-(6-(8-(5-(4-ethylpiperazin-1-yl)pyridin-2-ylamino)imidazo[1,2-a]pyridin-6-yl)-1H-indazol-3-yl)ethanol | 92 | 371.2 |

TABLE 1-continued

Syk IC$_{50}$ and MS Data for Selected Compounds

| Structure | Name | IC$_{50}$ @ 40 uM ATP | MH+ m/z |
|---|---|---|---|
| 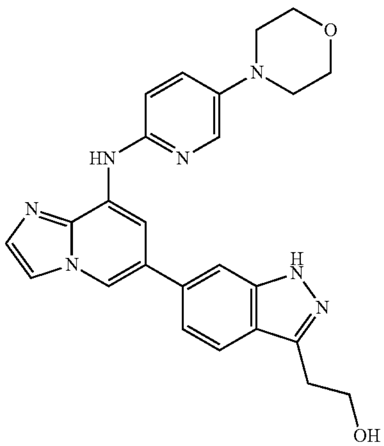 [SMILES: OCCc1n[nH]c2cc(-c3cc(Nc4ccc(N5CCOCC5)cn4)c4nccn4c3)ccc12] | 2-(6-(8-(5-morpholinopyridin-2-ylamino)imidazo[1,2-a]pyridin-6-yl)-1H-indazol-3-yl)ethanol | 17 | 356.3 |
| 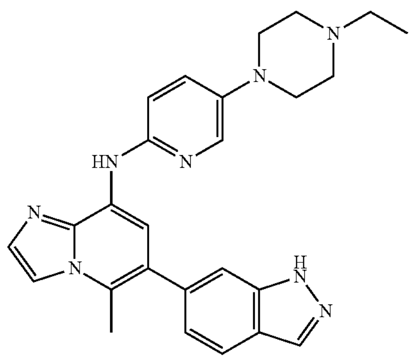 [SMILES: CCN1CCN(c2ccc(Nc3cc(-c4ccc5cn[nH]c5c4)c(C)n4ccnc34)nc2)CC1] | N-(5-(4-ethylpiperazin-1-yl)pyridin-2-yl)-6-(1H-indazol-6-yl)-5-methylimidazo[1,2-a]pyridin-8-amine | 17 | 414.4 |
| 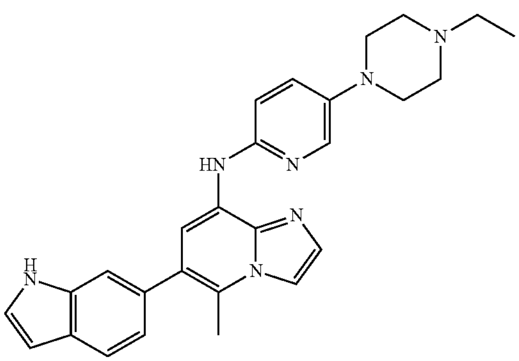 [SMILES: CCN1CCN(c2ccc(Nc3cc(-c4ccc5cc[nH]c5c4)c(C)n4ccnc34)nc2)CC1] | N-(5-(4-ethylpiperazin-1-yl)pyridin-2-yl)-6-(1H-indol-6-yl)-5-methylimidazo[1,2-a]pyridin-8-amine | 42 | 483.6 |
| 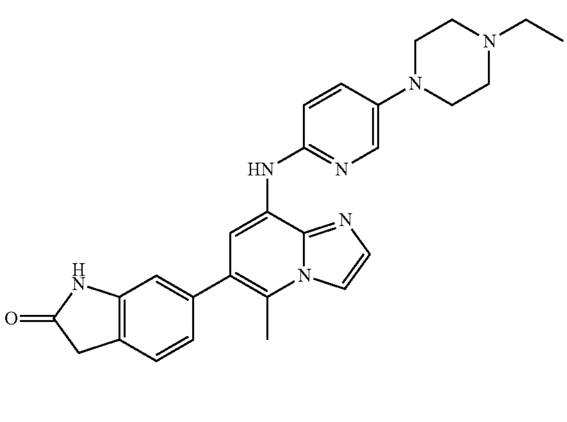 [SMILES: CCN1CCN(c2ccc(Nc3cc(-c4ccc5c(c4)NC(=O)C5)c(C)n4ccnc34)nc2)CC1] | 6-(8-(5-(4-ethylpiperazin-1-yl)pyridin-2-ylamino)-5-methylimidazo[1,2-a]pyridin-6-yl)indolin-2-one | 71 | 456.2 |

TABLE 1-continued

Syk IC$_{50}$ and MS Data for Selected Compounds

| Structure | Name | IC$_{50}$ @ 40 uM ATP | MH+ m/z |
|---|---|---|---|
| 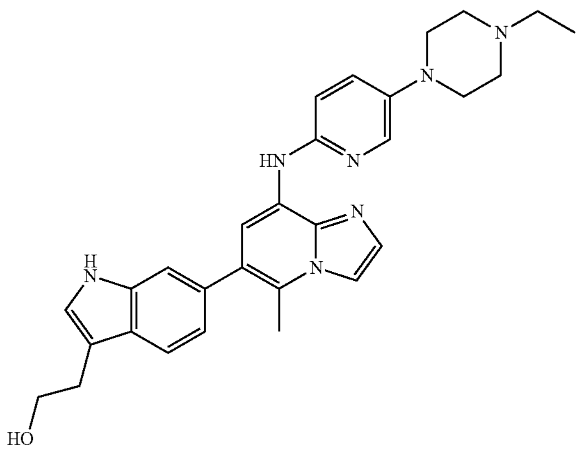 [SMILES: CCN1CCN(c2ccc(Nc3cc(-c4ccc5c(CCO)c[nH]c5c4)c(C)n4ccnc34)nc2)CC1] | 2-(6-(8-(5-(4-ethylpiperazin-1-yl)pyridin-2-ylamino)-5-methylimidazo[1,2-a]pyridin-6-yl)-1H-indol-3-yl)ethanol | 301 | 453.2 |
| 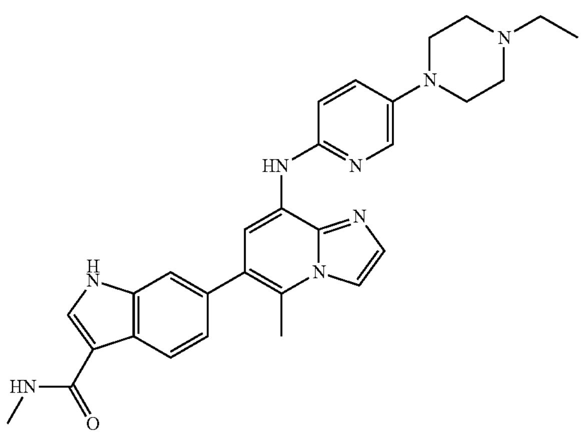 [SMILES: CCN1CCN(c2ccc(Nc3cc(-c4ccc5c(C(=O)NC)c[nH]c5c4)c(C)n4ccnc34)nc2)CC1] | 6-(8-(5-(4-ethylpiperazin-1-yl)pyridin-2-ylamino)-5-methylimidazo[1,2-a]pyridin-6-yl)-N-methyl-1H-indole-3-carboxamide | 883 | 452.3 |
| 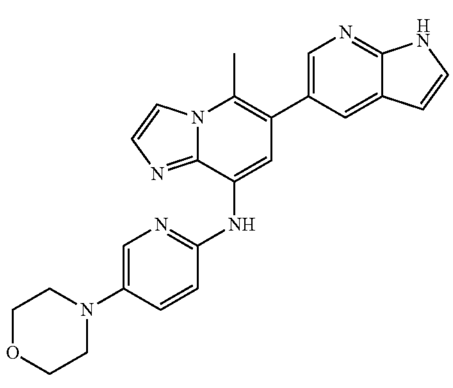 [SMILES: Cc1c(-c2cnc3[nH]ccc3c2)cc(Nc2ccc(N3CCOCC3)cn2)c2nccn12] | 5-methyl-N-(5-morpholinopyridin-2-yl)-6-(1H-pyrrolo[2,3-b]pyridin-5-yl)imidazo[1,2-a]pyridin-8-amine | 166 | 468.3 |

TABLE 1-continued

Syk IC$_{50}$ and MS Data for Selected Compounds

| Structure | Name | IC$_{50}$ @ 40 uM ATP | MH+ m/z |
|---|---|---|---|
| 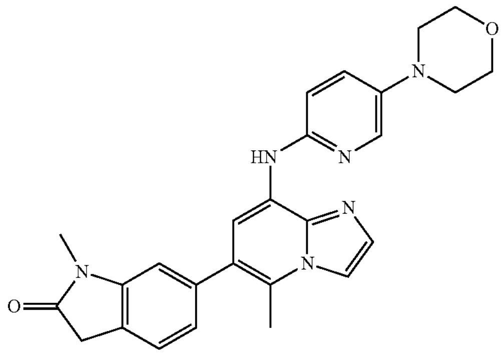 [SMILES: Cc1c(-c2ccc3c(c2)N(C)C(=O)C3)cc(Nc2ccc(N3CCOCC3)cn2)c2nccn12] | 1-methyl-6-(5-methyl-8-(5-morpholinopyridin-2-ylamino)imidazo[1,2-a]pyridin-6-yl)indolin-2-one | 1029 | 496.2 |
| 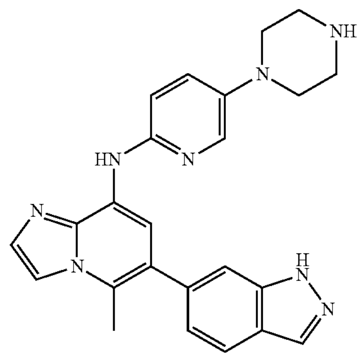 [SMILES: Cc1c(-c2ccc3cn[nH]c3c2)cc(Nc2ccc(N3CCNCC3)cn2)c2nccn12] | 6-(1H-indazol-6-yl)-5-methyl-N-(5-(piperazin-1-yl)pyridin-2-yl)imidazo[1,2-a]pyridin-8-amine | 128 | 509.2 |
| 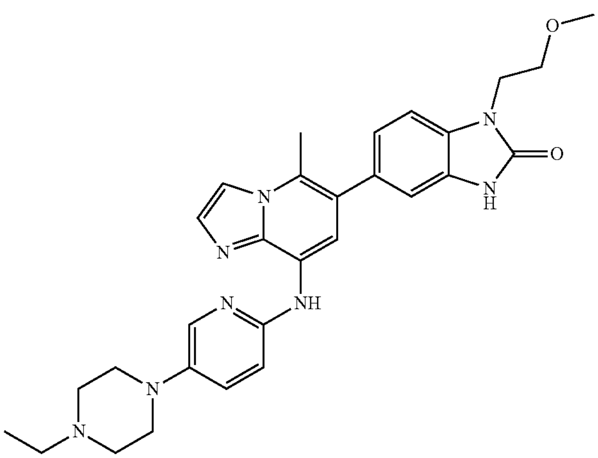 [SMILES: CCN1CCN(c2ccc(Nc3cc(-c4ccc5c(c4)[nH]c(=O)n5CCOC)c(C)n4ccnc34)nc2)CC1] | 5-(8-(5-(4-ethylpiperazin-1-yl)pyridin-2-ylamino)-5-methylimidazo[1,2-a]pyridin-6-yl)-1-(2-methoxyethyl)-1H-benzo[d]imidazol-2(3H)-one | 55 | 426.1 |
| 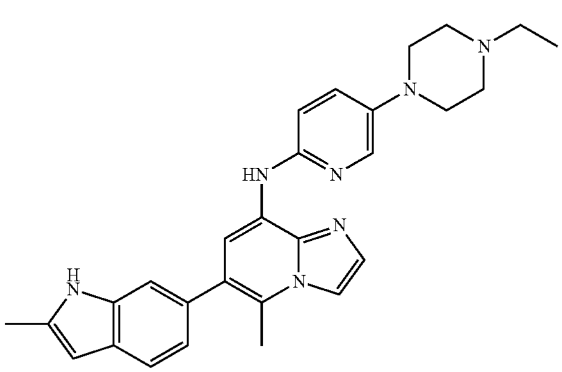 [SMILES: CCN1CCN(c2ccc(Nc3cc(-c4ccc5cc(C)[nH]c5c4)c(C)n4ccnc34)nc2)CC1] | N-(5-(4-ethylpiperazin-1-yl)pyridin-2-yl)-5-methyl-6-(2-methyl-1H-indol-6-yl)imidazo[1,2-a]pyridin-8-amine | 423 | 455.1 |

TABLE 1-continued

Syk IC$_{50}$ and MS Data for Selected Compounds

| Structure | Name | IC$_{50}$ @ 40 uM ATP | MH+ m/z |
|---|---|---|---|
| 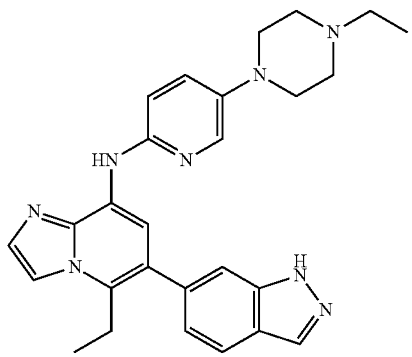 [SMILES: CCc1c(-c2ccc3cn[nH]c3c2)cc(Nc2ccc(N3CCN(CC)CC3)cn2)c2nccn12] | 5-ethyl-N-(5-(4-ethylpiperazin-1-yl)pyridin-2-yl)-6-(1H-indazol-6-yl)imidazo[1,2-a]pyridin-8-amine | 252 | 425.2 |
| 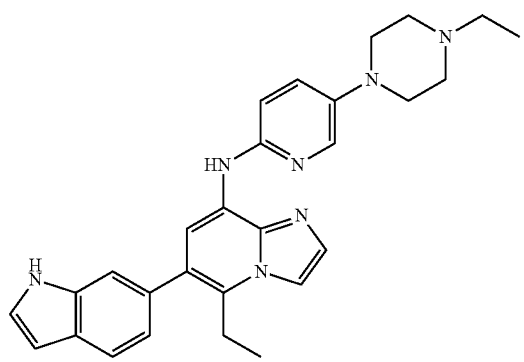 [SMILES: CCc1c(-c2ccc3cc[nH]c3c2)cc(Nc2ccc(N3CCN(CC)CC3)cn2)c2nccn12] | 5-ethyl-N-(5-(4-ethylpiperazin-1-yl)pyridin-2-yl)-6-(1H-indol-6-yl)imidazo[1,2-a]pyridin-8-amine | 272 | 527.2 |
| 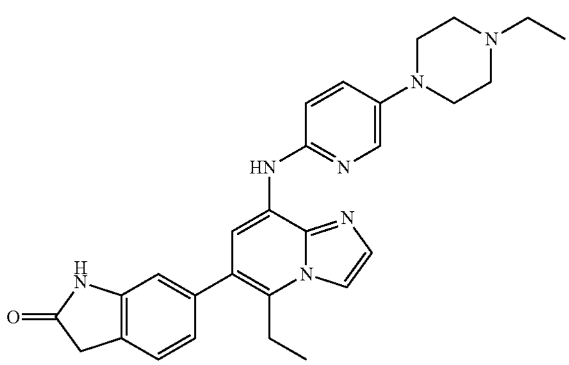 [SMILES: CCc1c(-c2ccc3c(c2)NC(=O)C3)cc(Nc2ccc(N3CCN(CC)CC3)cn2)c2nccn12] | 6-(5-ethyl-8-(5-(4-ethylpiperazin-1-yl)pyridin-2-ylamino)imidazo[1,2-a]pyridin-6-yl)indolin-2-one | 532 | 466.2 |
| 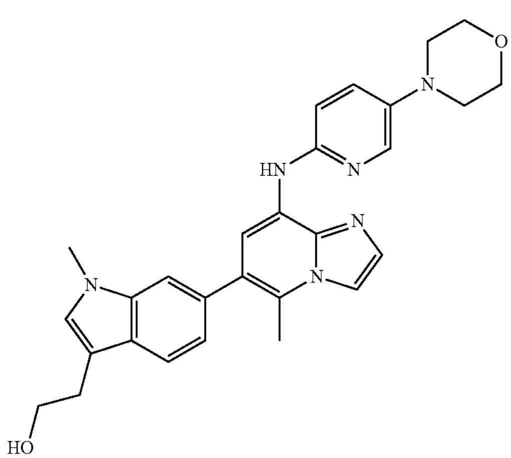 [SMILES: Cc1c(-c2ccc3c(CCO)cn(C)c3c2)cc(Nc2ccc(N3CCOCC3)cn2)c2nccn12] | 2-(1-methyl-6-(5-methyl-8-(5-morpholinopyridin-2-ylamino)imidazo[1,2-a]pyridin-6-yl)-1H-indol-3-yl)ethanol | 320 | 467.2 |

TABLE 1-continued

Syk IC$_{50}$ and MS Data for Selected Compounds

| Structure | Name | IC$_{50}$ @ 40 uM ATP | MH+ m/z |
|---|---|---|---|
| 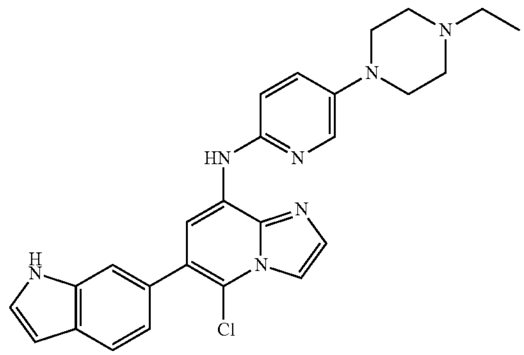 [SMILES: CCN1CCN(c2ccc(Nc3cc(-c4ccc5cc[nH]c5c4)c(Cl)n4ccnc34)nc2)CC1] | 5-chloro-N-(5-(4-ethylpiperazin-1-yl)pyridin-2-yl)-6-(1H-indol-6-yl)imidazo[1,2-a]pyridin-8-amine | 271 | 466.2 |
| 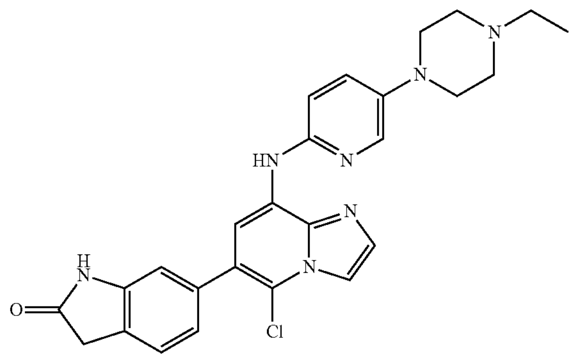 [SMILES: CCN1CCN(c2ccc(Nc3cc(-c4ccc5c(c4)NC(=O)C5)c(Cl)n4ccnc34)nc2)CC1] | 6-(5-chloro-8-(5-(4-ethylpiperazin-1-yl)pyridin-2-ylamino)imidazo[1,2-a]pyridin-6-yl)indolin-2-one | 80 | 482.2 |
| 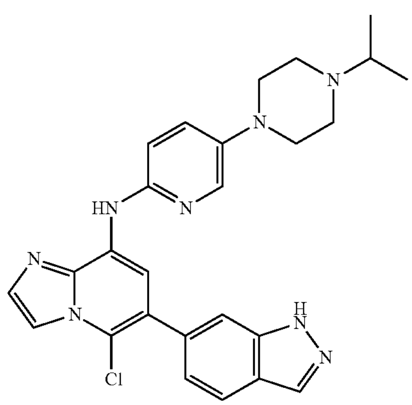 [SMILES: CC(C)N1CCN(c2ccc(Nc3cc(-c4ccc5cn[nH]c5c4)c(Cl)n4ccnc34)nc2)CC1] | 5-chloro-6-(1H-indazol-6-yl)-N-(5-(4-isopropylpiperazin-1-yl)pyridin-2-yl)imidazo[1,2-a]pyridin-8-amine | 32 | 483.2 |
| 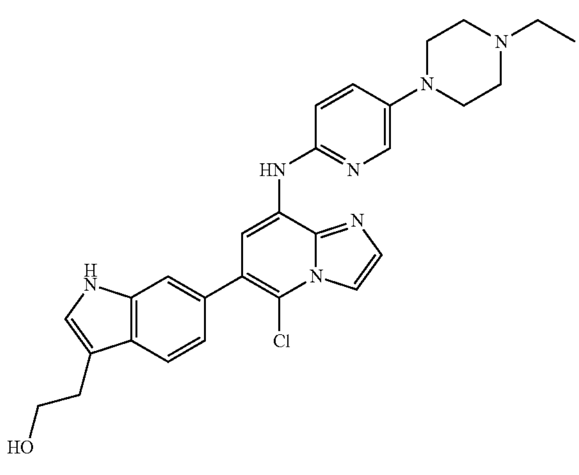 [SMILES: CCN1CCN(c2ccc(Nc3cc(-c4ccc5c(CCO)c[nH]c5c4)c(Cl)n4ccnc34)nc2)CC1] | 2-(6-(5-chloro-8-(5-(4-ethylpiperazin-1-yl)pyridin-2-ylamino)imidazo[1,2-a]pyridin-6-yl)-1H-indol-3-yl)ethanol | 215 | 472.1 |

TABLE 1-continued

Syk IC$_{50}$ and MS Data for Selected Compounds

| Structure | Name | IC$_{50}$ @ 40 uM ATP | MH+ m/z |
|---|---|---|---|
| 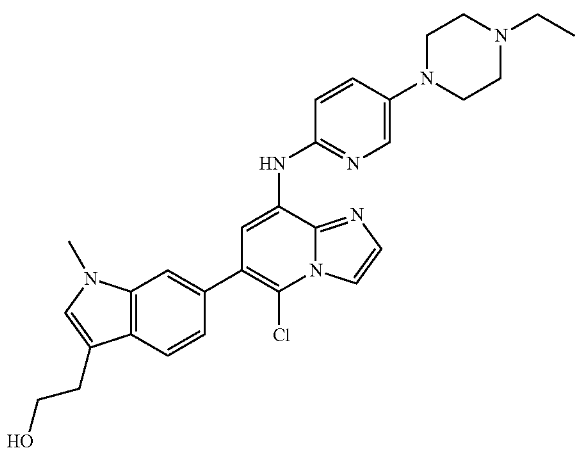 [SMILES: CCN1CCN(c2ccc(Nc3cc(-c4ccc5c(CCO)cn(C)c5c4)c(Cl)n4ccnc34)nc2)CC1] | 2-(6-(5-chloro-8-(5-(4-ethylpiperazin-1-yl)pyridin-2-ylamino)imidazo[1,2-a]pyridin-6-yl)-1-methyl-1H-indol-3-yl)ethanol | 278 | 488.1 |
| 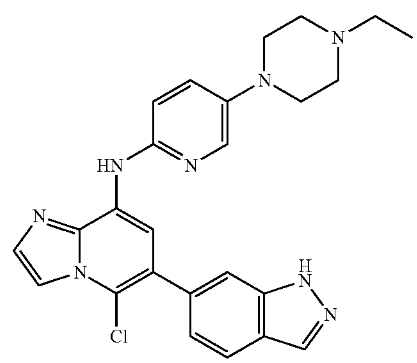 [SMILES: CCN1CCN(c2ccc(Nc3cc(-c4ccc5cn[nH]c5c4)c(Cl)n4ccnc34)nc2)CC1] | 5-chloro-N-(5-(4-ethylpiperazin-1-yl)pyridin-2-yl)-6-(1H-indazol-6-yl)imidazo[1,2-a]pyridin-8-amine | 14 | 487.1 |
| 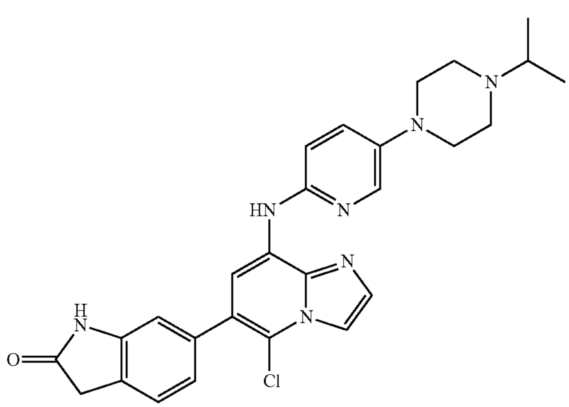 [SMILES: CC(C)N1CCN(c2ccc(Nc3cc(-c4ccc5c(c4)NC(=O)C5)c(Cl)n4ccnc34)nc2)CC1] | 6-(5-chloro-8-(5-(4-isopropylpiperazin-1-yl)pyridin-2-ylamino)imidazo[1,2-a]pyridin-6-yl)indolin-2-one | 17 | 516.2 |

TABLE 1-continued

Syk IC$_{50}$ and MS Data for Selected Compounds

| Structure | Name | IC$_{50}$ @ 40 uM ATP | MH+ m/z |
|---|---|---|---|
| 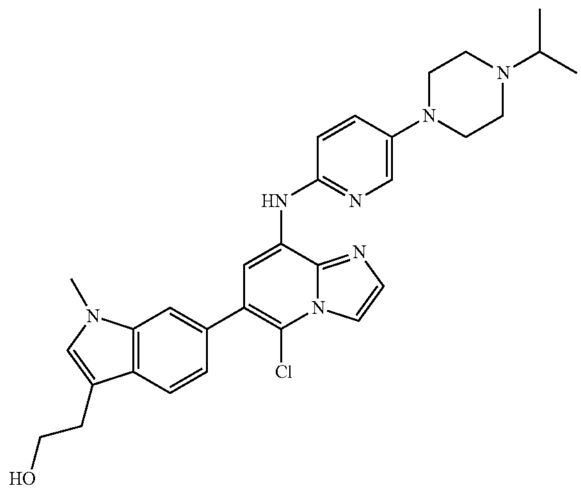 [SMILES: CC(C)N1CCN(c2ccc(Nc3cc(-c4ccc5c(CCO)cn(C)c5c4)c(Cl)n4ccnc34)nc2)CC1] | 2-(6-(5-chloro-8-(5-(4-isopropylpiperazin-1-yl)pyridin-2-ylamino)imidazo[1,2-a]pyridin-6-yl)-1-methyl-1H-indol-3-yl)ethanol | 218 | 530.2 |
| 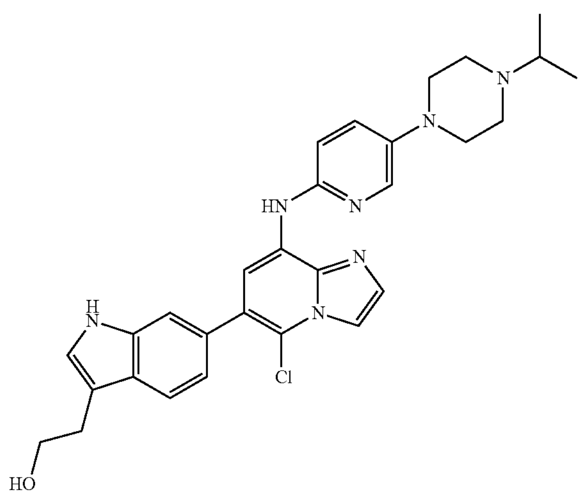 [SMILES: CC(C)N1CCN(c2ccc(Nc3cc(-c4ccc5c(CCO)c[nH]c5c4)c(Cl)n4ccnc34)nc2)CC1] | 2-(6-(5-chloro-8-(5-(4-isopropylpiperazin-1-yl)pyridin-2-ylamino)imidazo[1,2-a]pyridin-6-yl)-1H-indol-3-yl)ethanol | 15 | 473.1 |
| 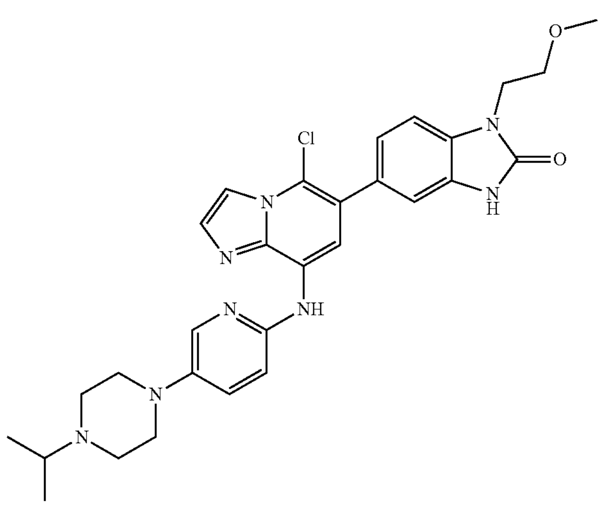 [SMILES: COCCn1c(=O)[nH]c2cc(-c3cc(Nc4ccc(N5CCN(C(C)C)CC5)cn4)c4nccn4c3Cl)ccc21] | 5-(5-chloro-8-(5-(4-isopropylpiperazin-1-yl)pyridin-2-ylamino)imidazo[1,2-a]pyridin-6-yl)-1-(2-methoxyethyl)-1H-benzo[d]imidazol-2(3H)-one | 12 | 502.1 |

TABLE 1-continued

Syk IC$_{50}$ and MS Data for Selected Compounds

| Structure | Name | IC$_{50}$ @ 40 uM ATP | MH+ m/z |
|---|---|---|---|
| 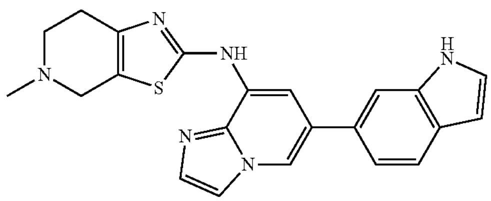 [SMILES: CN1CCc2nc(Nc3cc(-c4ccc5cc[nH]c5c4)cn4ccnc34)sc2C1] | N-(6-(1H-indol-6-yl)imidazo[1,2-a]pyridin-8-yl)-5-methyl-4,5,6,7-tetrahydrothiazolo[5,4-c]pyridin-2-amine | 72 | 544.2 |
| 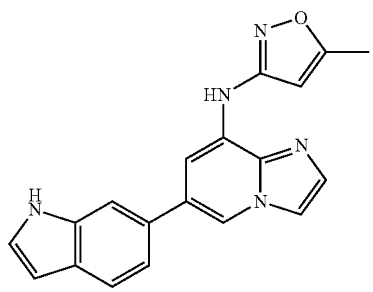 [SMILES: Cc1cc(Nc2cc(-c3ccc4cc[nH]c4c3)cn3ccnc23)no1] | N-(6-(1H-indol-6-yl)imidazo[1,2-a]pyridin-8-yl)-5-methylisoxazol-3-amine | 49 | 530.2 |
| 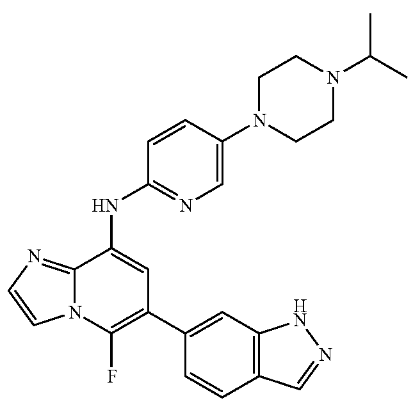 [SMILES: CC(C)N1CCN(c2ccc(Nc3cc(-c4ccc5cn[nH]c5c4)c(F)n4ccnc34)nc2)CC1] | 5-fluoro-6-(1H-indazol-6-yl)-N-(5-(4-isopropylpiperazin-1-yl)pyridin-2-yl)imidazo[1,2-a]pyridin-8-amine | 68 | 561.2 |
| 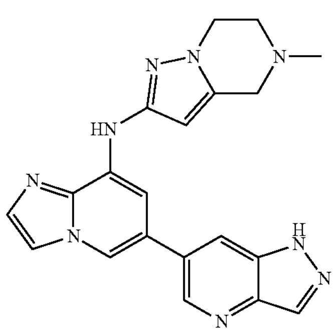 [SMILES: CN1CCn2nc(Nc3cc(-c4cnc5cn[nH]c5c4)cn4ccnc34)cc2C1] | N-(6-(1H-pyrazolo[4,3-b]pyridin-6-yl)imidazo[1,2-a]pyridin-8-yl)-5-methyl-4,5,6,7-tetrahydropyrazolo[1,5-a]pyrazin-2-amine | 26.38 | 401.1 |

TABLE 1-continued

Syk IC$_{50}$ and MS Data for Selected Compounds

| Structure | Name | IC$_{50}$ @ 40 uM ATP | MH+ m/z |
|---|---|---|---|
| 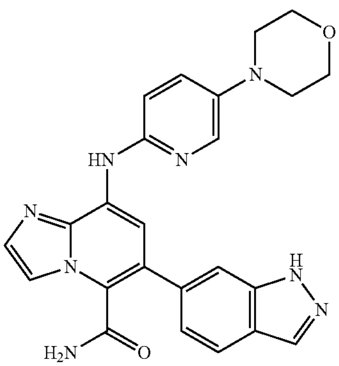 [SMILES: NC(=O)c1c(-c2ccc3cn[nH]c3c2)cc(Nc2ccc(N3CCOCC3)cn2)c2nccn12] | 6-(1H-indazol-6-yl)-8-(5-morpholinopyridin-2-ylamino)imidazo[1,2-a]pyridine-5-carboxamide | 569.46 | 330.1 |
| 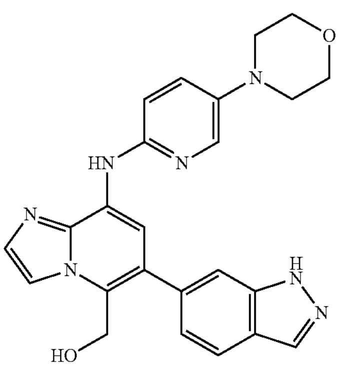 [SMILES: OCc1c(-c2ccc3cn[nH]c3c2)cc(Nc2ccc(N3CCOCC3)cn2)c2nccn12] | (6-(1H-indazol-6-yl)-8-(5-morpholinopyridin-2-ylamino)imidazo[1,2-a]pyridin-5-yl)methanol | 75.48 | 471.2 |
| 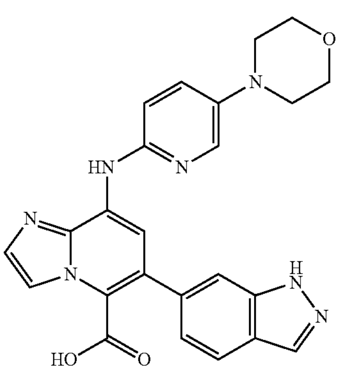 [SMILES: O=C(O)c1c(-c2ccc3cn[nH]c3c2)cc(Nc2ccc(N3CCOCC3)cn2)c2nccn12] | 6-(1H-indazol-6-yl)-8-(5-morpholinopyridin-2-ylamino)imidazo[1,2-a]pyridine-5-carboxylic acid | 4227.2 | 386.2 |
| 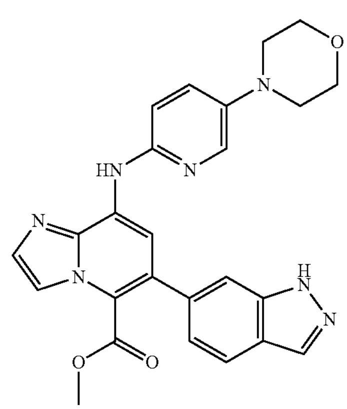 [SMILES: COC(=O)c1c(-c2ccc3cn[nH]c3c2)cc(Nc2ccc(N3CCOCC3)cn2)c2nccn12] | methyl 6-(1H-indazol-6-yl)-8-(5-morpholinopyridin-2-ylamino)imidazo[1,2-a]pyridine-5-carboxylate | 43.29 | 455.2 |

Example 18

Biochemical Syk Assay

A generalized procedure for one standard biochemical Syk Kinase Assay that can be used to test compounds disclosed in this application is as follows:

A master mix minus Syk enzyme is prepared containing 1× Cell Signaling kinase buffer (25 mM Tris-HCl, pH 7.5, 5 mM beta-glycerophosphate, 2 mM dithiothreitol, 0.1 mM $Na_3VO_4$, 10 mM $MgCl_2$), 0.5 µM Promega PTK Biotinylated peptide substrate 1, 0.01% casein, 0.01% Triton-X100, and 0.25% glycerol. A master mix plus Syk enzyme is prepared containing 1× Cell Signaling kinase buffer, 0.5 µM PTK Biotinylated peptide substrate 1, 0.01% casein, 0.01% Triton-X100, 0.25% glycerol and 0.4 ng/well Syk enzyme. Syk enzyme is purchased from Cell Signaling Technologies, expressed in baculovirus and is an N-terminally GST-tagged full length human wildtype Syk (accession number NM-00377).

The Syk protein is purified in one step using glutathione-agarose. The purity of the final protein preparation is assessed by SDS-PAGE and Coomassie staining. A solution of 200 µM ATP is prepared in water and adjusted to pH 7.4 with 1N NaOH. A quantity of 1.25 µL of compounds in 5% DMSO is transferred to a 96-well ½ area Costar polystyrene plate.

Compounds are tested singly and with an 11-point dose-responsive curve (starting concentration is 10-1 µM; 1:2 dilution). A quantity of 18.75 µL of master mix minus enzyme (as a negative control) and master mix plus enzyme is transferred to appropriate wells in 96-well ½ area Costar polystyrene plate. 5 µL of 200 µM ATP is added to that mixture in the 96-well ½ area Costar polystyrene plate for final ATP concentration of 40 µM.

The reaction is allowed to incubate for 1 hour at room temperature. The reaction is stopped with Perkin Elmer 1× detection buffer containing 30 mM EDTA, 80 nM SA-APC, and 4 nM PT66 Ab. The plate is read using time-resolved fluorescence with a Perkin Elmer Envision using excitation filter 330 nm, emission filter 665 nm, and $2^{nd}$ emission filter 615 nm. $IC_{50}$ values are subsequently calculated using a linear regression algorithm.

Example 19

Ramos Cell pBLNK(Y96) Assay

Another generalized procedure for a standard cellular Syk Kinase Assay that can be used to test compounds disclosed in this application is as follows:

Ramos cells are serum starved at $2 \times 10^6$ cells/ml in serum-free RPMI for 1 hour in an upright T175 Falcon TC flask. Cells are centrifuged (1100 rpm×5 min) and incubated at a density of $0.5 \times 10^7$ cells/ml in the presence of test compound or DMSO controls for 1 hr at 37° C. Cells are then stimulated by incubating with 10 µg/ml anti-human IgM $F(ab)_2$ for 5 minutes at 37° C. Cells are pelleted, lysed in 40 µl cell lysis buffer, and mixed with Invitrogen SDS-PAGE loading buffer. 20 µl of cell lysate for each sample are subject to SDS-PAGE and western blotting with anti-phosphoBLNK(Tyr96) antibody (Cell Signaling Technology #3601) to assess Syk activity and anti-Syk antibody (BD Transduction Labs #611116) to control for total protein load in each lysate. The images are detected using fluorescent secondary detection systems and the LiCor Odyssey software.

Example 20

B-Cell Proliferation Assay

A generalized procedure for a standard cellular B-cell proliferation assay that can be used to test compounds disclosed in this application is as follows:

B-cells are purified from spleens of 8-16 week old Balb/c mice using a B-cell isolation kit (Miltenyi Biotech, Cat #130-090-862). Test compounds are diluted in 0.25% DMSO and incubated with $2.5 \times 10^5$ purified mouse splenic B-cells for 30 min prior to addition of 10 µg/ml of an anti-mouse IgM antibody (Southern Biotechnology Associates Cat #1022-01) in a final volume of 100 µl. Following 24 hr incubation, 1 µCi $^3$H-thymidine is added and plates are incubated an additional 36 hr prior to harvest using the manufacturer's protocol for SPA[$^3$H] thymidine uptake assay system (Amersham Biosciences # RPNQ 0130). SPA-bead based fluorescence is counted in a microbeta counter (Wallace Triplex 1450, Perkin Elmer).

Example 21

T Cell Proliferation Assay

A generalized procedure for a standard T cell proliferation assay that can be used to test compounds disclosed in this application is as follows:

T cells are purified from spleens of 8-16 week old Balb/c mice using a Pan T cell isolation kit (Miltenyi Biotech, Cat #130-090-861). Test compounds are diluted in 0.25% DMSO and incubated with $2.5 \times 10^5$ purified mouse splenic T cells in a final volume of 100 µl in flat clear bottom plates precoated for 90 min at 37° C. with 10 µg/ml each of anti-CD3 (BD #553057) and anti-CD28 (BD #553294) antibodies. Following 24 hr incubation, 1 µCi $^3$H-thymidine is added and plates incubated an additional 36 hr prior to harvest using the manufacturer's protocol for SPA[$^3$H]thymidine uptake assay system (Amersham Biosciences # RPNQ 0130). SPA-bead based fluorescence was counted in a microbeta counter (Wallace Triplex 1450, Perkin Elmer).

Example 22

CD69 Inhibition Assay

A generalized procedure for a standard assay for the inhibition of B-cell activity that can be used to test compounds disclosed in this application is as follows:

Total mouse splenocytes are purified from spleens of 8-16 week old Balb/c mice by red blood cell lysis (BD Pharmingen #555899). Testing compounds are diluted to 0.5% DMSO and incubated with $1.25 \times 10^6$ splenocytes in a final volume of 200 µl in flat clear bottom plates (Falcon 353072) for 60 min at 37° C. Cells are then stimulated with the addition of 15 µg/ml IgM (Jackson ImmunoResearch 115-006-020), and incubated for 16 hr at 37° C. under an atmosphere containing 5% $CO_2$. Following the 16 hr incubation, cells are transferred to conical bottom clear 96-well plates and pelleted by centrifugation at 1200×g×5 min. Cells are preblocked by CD16/CD32 (BD Pharmingen #553142), followed by triple staining with CD19-FITC (BD Pharmingen #553785), CD69-PE (BD Pharmingen #553237), and 7AAD (BD Pharmingen #51-68981E). Cells are sorted on a BD FACSCalibur and gated on the CD19$^+$/7AAD$^-$ population. The levels of CD69 surface expression on the gated population is measured versus test compound concentration.

Example 23

BMMC Degranulation

A generalized procedure for a standard assay for bone-marrow derived mouse mast cell (BMMC) degranulation that can be used to test compounds disclosed in this application is as follows:

Bone-marrow derived mast cells are cultured for >4 weeks with IL-3 (10 ng/ml) and SCF (10 ng/ml). The cells are determined to be >90% cKi$^+$/FceRI$^+$ by FACS analysis at the time of use. Cells ($6 \times 10^7$ cells/50 ml) are serum-starved in a T150 tissue culture flask for 16 h in the absence of IL-3 and SCF containing IgEα-DNP at 1 ug/ml. Overnight sensitized cells are washed twice in Tyrodes buffer and resuspended to $5 \times 10^6$ cells/ml. $5 \times 10^5$ cells (100 μl) are plated in a 96 well microtiter plate (Falcon 353072) and test compounds are serially diluted to a final concentration 0.25% DMSO in the plate for 1 hr at 37° C. under an atmosphere containing 5% $CO_2$. Wells are treated with a DNP-BSA antigen challenge (50 ng/ml) and incubated for and additional 30 min at 37° C. Supernatants are assayed for hexosamimidase release versus control wells. Cell pellets are simultaneously lysed and assed for total hexosamimidase release to calculate specific release. Dose-response curves are generated using 4-parameter logistical fit and $IC_{50}$s calculated.

Example 24

Passive Cutaneous Anaphylaxis (PCA)

The following is a procedure for a standard PCA model used for measuring in vivo IgE anti-DNP Ab sensitization and DNP-BSA antigen for triggering mast cell degranulation and release of immune regulators that cause acute vessel permeability monitored by Evan's blue dye into the inflamed area in the mouse ear.

Reagents: Anti-DNP IgE: is supplied as 1.2 mg/ml in a phosphate buffered solution with BSA for additional protein and azide for sterility. This is diluted 1:100 in sterile PBS as a 12 μg/ml working stock that can be further diluted in PBS to the appropriate concentration for injection. A further 1:5 dilution gives a final 1:500 solution at 2.4 ng/μL. (10 μL/ear=24 ng). Sterile PBS alone is used as a negative control.

Evan's blue dye: A 2% stock in saline is sterile filtered and diluted 1:1 with DNP-BSA saline solution for a final concentration of 1% for injection.

DNP-BSA: is made up at 4 mg/mL in sterile ddH$_2$O. It is further diluted 1:1 with sterile saline prior to use. This solution or a further dilution in saline is diluted 1:1 with 2% Evan's Blue in sterile saline that has been filtered through a 0.02 μm filter and refiltered prior to injection. For these experiments a final solution of 0.5 mg/ml of DNP-BSA in 1% Evans blue is used, and aliquots of 200 μL are injected into the tail vein.

General PCA Protocol Using Intradermal Ear Sensitization

1) On day 0, animals anesthetized with isofluorine are passively sensitized by intradermal injections of IgE anti-DNP using a 29-gauge insulin syringe. By convention, the right ear receives 10 μL intradermal injection of anti-DNP IgE, while the left ear receives PBS. 2) 20 hr post sensitization, antigen challenge is administered by tail i.v. injection of DNP-BSA in 200 μl of 1% Evan's blue dye solution in saline. Tails are immersed in warm water prior to iv injection. 3) 30 minutes to 2 hr prior to this antigen challenge, drug is delivered sc or po in 10% EtOH/20% cremaphor/70% saline. 4) Animals are sacrifice by $CO_2$ inhalation 30-60 min post antigen challenge and ears are removed for extraction of Evan's blue dye in 500 μL of formamide overnight at 65° C. 5) Blood is obtained by cardiac puncture just prior to final cervical dislocation and processed for plasma to provide PK analysis. 6) Evan's blue dye is quantified by reading absorbency of 200 μL of extracted solution in microtiter plates at 620 nm.

Study Design of Experiment

Each animal has one anti-DNP IgE sensitized ear (right ear by convention) and one PBS control ear (left ear by convention). Groups 1-8: represent the vehicle and compound testing arms; Group 9: represents the non-antigen negative control; Group 10: represents the non-sensitized challenged negative control; Group 11: represents the non-antigen challenged, non-sensitized negative control group (Groups 9-11 represent negative controls for background levels only and require only minimal number of animals per group.)

The compounds disclosed in the examples above were tested in the Syk biochemical assay described herein (Example 18) and certain of those compounds exhibited an $IC_{50}$ value less than or equal to 1 micromolar. Certain of those compounds exhibited an $IC_{50}$ value less than or equal to 100 nM. Certain of those compounds exhibited an $IC_{50}$ value less than or equal to 10 nM. Certain of those compounds exhibited an $IC_{50}$ value less than or equal to 1 nM.

Some of the compounds disclosed in Example 16 were tested in the B-cell proliferation assay (as described in Example 20) and exhibited an $IC_{50}$ value less than or equal to 10 micromolar. Certain of those compounds exhibited an $IC_{50}$ value less than or equal to 1 micromolar.

Certain of those compounds did not inhibit T-cell proliferation and had IC50 values greater than or equal to 5 micromolar when assayed under conditions described herein (as described in Example 20).

Certain compounds described herein exhibited IC50 values for inhibition of T-cell proliferation that were at least 3-fold, and in some instances 5-fold, greater than the IC50 values of those compounds for inhibition of B-cell proliferation.

Some of the compounds described herein were tested in an assay for inhibition of B-cell activity (under the conditions described in Example 22), and exhibited an IC50 value less than or equal to 10 micromolar. Certain of those compounds exhibited an IC50 value less than or equal to 1 micromolar.

Some of the compounds disclosed in described herein exhibited both biochemical and cell-based activity. For example, some of the compounds described herein exhibited an IC50 value less than or equal to 10 micromolar in the Syk biochemical assay described herein (Example 18) and an IC50 value less than or equal to 10 micromolar in at least one of the cell-based assays (other than the T-cell assay) described herein (Examples 19, 20, 22 or 23). Certain of those compounds exhibited an IC50 value less than or equal to 1 micromolar in the Syk biochemical assay described herein (Example 19) and an IC50 value less than or equal to 10 micromolar in at least one of the cell-based assays (other than the T-cell assay) described herein (Examples 19, 20, 22 or 23). Certain of those compounds exhibited an IC50 value less than or equal to 0.1 micromolar and an IC50 value less than or equal to 10 micromolar in at least one of the cell-based assays (other than the T-cell assay) described herein (Examples 19, 20, 22 or 23).

While some embodiments have been shown and described, various modifications and substitutions may be made thereto without departing from the spirit and scope of the invention. For example, for claim construction purposes, it is not intended that the claims set forth hereinafter be construed in any way narrower than the literal language thereof, and it is thus not intended that exemplary embodiments from the specification be read into the claims. Accordingly, it is to be understood that the present invention has been described by way of illustration and not limitations on the scope of the claims.

What is claimed:

1. A method for inhibiting Syk activity in a patient having a disease responsive to the inhibition of Syk activity, comprising administering to the patient an effective amount of at least one chemical entity chosen from compounds of Formula I:

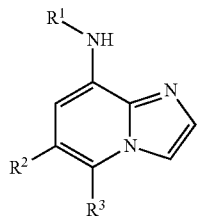

or a pharmaceutically acceptable salt thereof, wherein
$R^1$ is optionally substituted phenyl;
$R^2$ is 2,3-dimethyl-2H-indazol-6-yl, 1H-indazolyl-6-yl, 1-methyl-1H-indazol-5-yl, 1-methyl-1H-indazol-6-yl, 3,4-dihydro-2H-1,4-benzoxazin-3-one-6-yl, 1-(2-hydroxyethyl)-1H-benzo[d]imidazol-2(3H)-one-5-yl, 3-amino-1H-indazol-6-yl, 1H-pyrrolo[3,2-b]pyridine-6-yl, 1,3-benzoxazol-6-yl, 3,4-dihydro-2H-1,4-benzoxazin-6-yl, 2-hydroxyquinoxalin-7-yl, 3-aminoquinolin-6-yl, 2,3-dihydro-1H-indol-6-yl, 1H,2H,3H-pyrido[2,3-b][1,4]oxazin-2-one, (3-hydroxyethyl)-1H-indol-6-yl, benzothiazolyl, 2-aminoquinazolin-6-yl, 3,3-dimethylindolin-2-one, 2,3-dihydro-1H-indol-2-one, 4-fluoro-1H-indazol-6-yl, 5-fluoro-1H-indazol-6-yl, or 3-amino-1H-indazol-6-yl; and
$R^3$ is hydrogen, lower alkyl, halogen, carboxamido, or $CO_2H$,
wherein the disease responsive to the inhibition of Syk activity is an inflammatory disorder, an allergic disorder, an autoimmune disease, or cancer.

2. The method according to claim 1, wherein $R^1$ is phenyl optionally substituted with one or more groups independently chosen from
hydroxy;
—$NR^bR^c$, wherein $R^b$ is chosen from hydrogen and $C_1$-$C_6$ alkyl optionally substituted with one or two groups independently chosen from hydroxy and —$OC_1$-$C_4$ alkyl, and $R^c$ is independently chosen from hydrogen and $C_1$-$C_4$ alkyl optionally substituted with one or two groups independently chosen from hydroxy and —$OC_1$-$C_4$ alkyl;
heterocycloalkyl optionally substituted with one or two groups independently chosen from hydroxy, $C_3$-$C_6$ cycloalkyl, $C_1$-$C_4$ alkyl, —$C_1$-$C_4$ alkyl-OH, —$C_1$-$C_4$ alkyl-O—$C_1$-$C_4$ alkyl, —$C_1$-$C_4$ alkyl-$NH_2$, —$N(C_1$-$C_4$ alkyl)($C_1$-$C_4$ alkyl), —$NH(C_1$-$C_4$ alkyl), —$C(O)(C_1$-$C_4$ alkyl), —$C(O)(C_1$-$C_4$ alkyl-OH), and —$OC_1$-$C_4$ alkyl;
—$OC_1$-$C_6$ alkyl optionally substituted with one or two groups independently chosen from hydroxy, $C_3$-$C_6$ cycloalkyl, $C_1$-$C_4$ alkyl, —$C_1$-$C_4$ alkyl-OH, —$C_1$-$C_4$ alkyl-O—$C_1$-$C_4$ alkyl, —$C_1$-$C_4$ alkyl-$NH_2$, —$N(C_1$-$C_4$ alkyl)($C_1$-$C_4$ alkyl), —$NH(C_1$-$C_4$ alkyl), and —$OC_1$-$C_4$ alkyl; and
$C_1$-$C_6$ alkyl optionally substituted with one or two groups independently chosen from hydroxy, $C_3$-$C_6$ cycloalkyl, $C_1$-$C_4$ alkyl, —$C_1$-$C_4$ alkyl-OH, —$C_1$-$C_4$ alkyl-O—$C_1$-$C_4$ alkyl, —$C_1$-$C_4$ alkyl-$NH_2$, —$N(C_1$-$C_4$ alkyl)($C_1$-$C_4$ alkyl), —$NH(C_1$-$C_4$ alkyl), and —$OC_1$-$C_4$ alkyl.

3. A method for inhibiting Syk activity in a patient having a disease responsive to the inhibition of Syk activity, comprising administering to the patient an effective amount of at least one chemical entity chosen from compounds of Formula I:

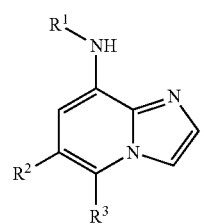

or a pharmaceutically acceptable salt thereof, wherein
$R^1$ is optionally substituted phenyl;
$R^2$ is 1H-indazolyl-6-yl, 1-methyl-1H-indazol-5-yl, 1-methyl-1H-indazol-6-yl, 3,4-dihydro-2H-1,4-benzoxazin-3-one-6-yl, 1,3-benzoxazol-6-yl, 3-aminoquinolin-6-yl, 1H-pyrrolo[3,2-b]pyridin-6-yl, or 2,3-dihydro-1H-indol-2-one-6-yl; and
$R^3$ is hydrogen, lower alkyl, halogen, carboxamido, or $CO_2H$,
wherein the disease responsive to the inhibition of Syk activity is an inflammatory disorder, an allergic disorder, an autoimmune disease, or cancer.

4. A method for inhibiting Syk activity in a patient having a disease responsive to the inhibition of Syk activity, comprising administering to the patient an effective amount of at least one chemical entity chosen from compounds of Formula I:

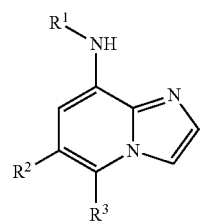

or a pharmaceutically acceptable salt thereof, wherein
$R^1$ is optionally substituted phenyl;
$R^2$ is 2,3-dimethyl-2H-indazol-6-yl, 1H-indazolyl-6-yl, 1-methyl-1H-indazol-5-yl, 1-methyl-1H-indazol-6-yl, 3,4-dihydro-2H-1,4-benzoxazin-3-one-6-yl, 1-(2-hydroxyethyl)-1H-benzo[d]imidazol-2(3H)-one-5-yl, 3-amino-1H-indazol-6-yl, 1H-pyrrolo[3,2-b]pyridine-6-yl, 1,3-benzoxazol-6-yl, 3,4-dihydro-2H-1,4-benzoxazin-6-yl, 2-hydroxyquinoxalin-7-yl, 3-aminoquinolin-6-yl, 2,3-dihydro-1H-indol-6-yl, 1H,2H,3H-pyrido[2,3-b][1,4]oxazin-2-one, (3-hydroxyethyl)-1H-indol-6-yl, benzothiazolyl, 2-aminoquinazolin-6-yl, 3,3-dimethylindolin-2-one, 2,3-dihydro-1H-indol-2-one, 4-fluoro-1H-indazol-6-yl, 5-fluoro-1H-indazol-6-yl, or 3-amino-1H-indazol-6-yl; and $R^3$ is chosen from hydrogen and methyl, wherein the disease responsive to the inhibition of Syk activity is an inflammatory disorder, an allergic disorder, an autoimmune disease, or cancer.

5. A method for inhibiting Syk activity in a patient having a disease responsive to the inhibition of Syk activity, comprising administering to the patient an effective amount of at least one chemical entity chosen from compounds of Formula I:

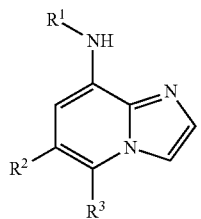

or a pharmaceutically acceptable salt thereof, wherein
$R^1$ is optionally substituted phenyl;
$R^2$ is 2,3-dimethyl-2H-indazol-6-yl, 1H-indazolyl-6-yl, 1-methyl-1H-indazol-5-yl, 1-methyl-1H-indazol-6-yl, 3,4-dihydro-2H-1,4-benzoxazin-3-one-6-yl, 1-(2-hydroxyethyl)-1H-benzo[d]imidazol-2(3H)-one-5-yl, 3-amino-1H-indazol-6-yl, 1H-pyrrolo[3,2-b]pyridine-6-yl, 1,3-benzoxazol-6-yl, 3,4-dihydro-2H-1,4-benzoxazin-6-yl, 2-hydroxyquinoxalin-7-yl, 3-aminoquinolin-6-yl, 2,3-dihydro-1H-indol-6-yl, 1H,2H,3H-pyrido[2,3-b][1,4]oxazin-2-one, (3-hydroxyethyl)-1H-indol-6-yl, benzothiazolyl, 2-aminoquinazolin-6-yl, 3,3-dimethylindolin-2-one, 2,3-dihydro-1H-indol-2-one, 4-fluoro-1H-indazol-6-yl, 5-fluoro-1H-indazol-6-yl, or 3-amino-1H-indazol-6-yl; and $R^3$ is hydrogen, wherein the disease responsive to the inhibition of Syk activity is an inflammatory disorder, an allergic disorder, an autoimmune disease, or cancer.

6. A method for inhibiting Syk activity in a patient having a disease responsive to the inhibition of Syk activity, comprising administering to the patient an effective amount of a compound having the structure:

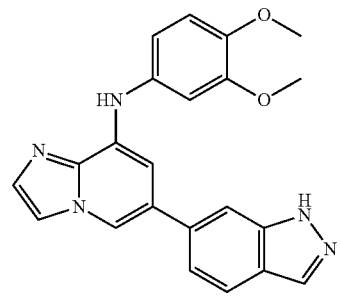 [SMILES: COc1ccc(Nc2cc(-c3ccc4cn[nH]c4c3)cn3ccnc23)cc1OC]

or a pharmaceutically acceptable salt thereof, wherein the disease responsive to the inhibition of Syk activity is an inflammatory disorder, an allergic disorder, an autoimmune disease, or cancer.

7. The method according to claim 1, wherein the patient is a human.

8. The method according to claim 1, wherein the disease responsive to inhibition of Syk activity is cancer.

9. The method according to claim 1, wherein the disease responsive to inhibition of Syk activity is B-cell lymphoma or leukemia.

10. The method according to claim 1, wherein the disease responsive to inhibition of Syk activity is rheumatoid arthritis.

11. The method according to claim 1, wherein the disease responsive to inhibition of Syk activity is allergic rhinitis.

12. The method according to claim 1, wherein the disease responsive to inhibition of Syk activity is adult respiratory distress syndrome (ARDs).

13. The method according to claim 1, wherein the disease responsive to inhibition of Syk activity is an allergy-induced inflammatory disease.

14. The method according to claim 1, wherein the disease responsive to inhibition of Syk activity is multiple sclerosis.

15. The method according to claim 1, wherein the disease responsive to inhibition of Syk activity is an autoimmune disease.

16. The method according to claim 1, wherein the disease responsive to inhibition of Syk activity is an inflammatory disease.

17. The method according to claim 1, wherein the disease responsive to inhibition of Syk activity is acute inflammatory reaction.

18. The method according to claim 1, wherein the disease responsive to inhibition of Syk activity is an allergic disorder.

19. The method according to claim 1, wherein the disease responsive to inhibition of Syk activity is polycystic kidney disease.

* * * * *